(12) United States Patent
Chang et al.

(10) Patent No.: US 12,064,545 B2
(45) Date of Patent: Aug. 20, 2024

(54) FLUID COLLECTION SYSTEMS

(71) Applicant: Allegiance Corporation, Waukegan, IL (US)

(72) Inventors: Stephany Chang, Chicago, IL (US); Douglas Alan Cundieff, Jacksonville, TX (US); Kok Hern Law, Singapore (SG); Wei Chen Lie, Singapore (SG); Sara Karle Wegener, Libertyville, IL (US); Robert John Weinberg, Spring Grove, IL (US); Yi Lin Ang, Singapore (SG); Varsha Kalyankar, Kenosha, WI (US)

(73) Assignee: ALLEGIANCE CORPORATION, Waukegan, IL (US)

(*) Notice: Subject to any disclaimer, the term of this patent is extended or adjusted under 35 U.S.C. 154(b) by 376 days.

(21) Appl. No.: 17/141,101

(22) Filed: Jan. 4, 2021

(65) Prior Publication Data
US 2021/0196866 A1 Jul. 1, 2021

Related U.S. Application Data

(63) Continuation of application No. 15/295,924, filed on Oct. 17, 2016, now abandoned.

(60) Provisional application No. 62/242,869, filed on Oct. 16, 2015.

(51) Int. Cl.
*A61M 1/00* (2006.01)
(52) U.S. Cl.
CPC .................................. *A61M 1/604* (2021.05)

(58) Field of Classification Search
CPC ............ A61M 1/60; A61M 1/604; A61M 1/63
See application file for complete search history.

(56) References Cited

U.S. PATENT DOCUMENTS

| | | | |
|---|---|---|---|
| 3,719,197 A | 3/1973 | Pannier et al. | |
| 3,745,999 A | 7/1973 | Deaton | |
| 4,465,485 A | 8/1984 | Kashmer et al. | |
| 4,681,571 A * | 7/1987 | Nehring | A61M 1/604 604/320 |
| 5,203,470 A | 4/1993 | Brown | |
| 5,470,324 A | 11/1995 | Cook et al. | |

(Continued)

FOREIGN PATENT DOCUMENTS

| | | |
|---|---|---|
| EP | 0525493 A1 | 2/1993 |
| EP | 1225930 B1 | 11/2006 |

(Continued)

OTHER PUBLICATIONS

Coopdech, QinPot, retrieved on Dec. 15, 2014, 10 pages.

(Continued)

*Primary Examiner* — Jessica Arble
(74) *Attorney, Agent, or Firm* — ArentFox Schiff LLP

(57) ABSTRACT

Fluid collection systems having a canister, a lid, and a liner assembly are described. The liner assembly may include a liner and a fitment assembly. The fitment assembly may be connected to the liner by a gland. The fitment assembly may be held in place by at least one of any number of features, including a bracket or other fitment support connected to the canister and/or the lid, supports integrated into the fitment itself, a snapping mechanism, or a notch in one or more of the canister and the lid that supports the fitment.

16 Claims, 64 Drawing Sheets

(56) References Cited

U.S. PATENT DOCUMENTS

| | | | |
|---|---|---|---|
| 5,725,516 A | 3/1998 | Cook et al. | |
| 6,056,730 A * | 5/2000 | Greter | A61M 1/784 604/319 |
| 6,093,230 A | 7/2000 | Johnson, III et al. | |
| 6,152,902 A | 11/2000 | Christian et al. | |
| 6,183,453 B1 * | 2/2001 | Swisher | A61M 5/1626 604/319 |
| 6,270,488 B1 | 8/2001 | Johnson et al. | |
| 6,409,220 B1 | 6/2002 | Wing et al. | |
| 6,499,495 B2 | 12/2002 | Jeng | |
| 6,780,309 B2 * | 8/2004 | Haldopoulos | B01D 46/0036 604/405 |
| 7,481,243 B2 | 1/2009 | Michaels et al. | |
| 7,635,359 B2 | 12/2009 | Nakazawa et al. | |
| 8,025,173 B2 | 9/2011 | Michaels | |
| 8,100,874 B1 | 1/2012 | Jordan et al. | |
| 8,118,796 B2 | 2/2012 | Rajamaki et al. | |
| 8,172,817 B2 | 5/2012 | Michaels et al. | |
| 8,460,256 B2 | 6/2013 | Michaels et al. | |
| 8,500,706 B2 | 8/2013 | Michaels et al. | |
| 2006/0079853 A1 * | 4/2006 | Christensen | A61M 1/68 604/317 |
| 2009/0005747 A1 * | 1/2009 | Michaels | A61M 1/604 604/319 |
| 2009/0287190 A1 | 11/2009 | Shippert | |
| 2010/0270222 A1 | 10/2010 | Lauer | |
| 2011/0178482 A1 | 7/2011 | Michaels et al. | |
| 2011/0180566 A1 | 7/2011 | Kobashi et al. | |
| 2015/0291352 A1 | 10/2015 | Morgan et al. | |

FOREIGN PATENT DOCUMENTS

| | | |
|---|---|---|
| WO | WO 0124846 A1 | 4/2001 |
| WO | WO 2015055893 A1 | 4/2001 |

OTHER PUBLICATIONS

Coopdech, QinPot, Retrieved on Dec. 15, 2014, Retrieved from the Internet URL: http://www.brandcom.ro/data/_editor/QIN%20POT%20romana%20andreesa(1).pdf, 21 pages.

Daiken Medical Co. Ltd., Coopdech, QinPot, Infection Control, Retrieved on Dec. 15, 2014, Retrieved from Internet URL: http://www.daiken-iki.co.jp/en/pi/in_qp.html. 2 pages.

Daiken Medical Co. Ltd., Coopdech, QinPot, The Wall Mount Type Closed 1000mL Suction System, Apr. 2011. 2 pages.

International Preliminary Report on Patentability and Written Opinion for PCT/US2016/057413 mailed Apr. 17, 2018, 7 pages.

International Search Report and Written Opinion for Application No. PCT/US2016/057413, mailed Jan. 30, 2017, 12 pages.

International Search Report and Written Opinion for Application No. PCT/US2017/029494, mailed Sep. 7, 2017, 14 pages.

* cited by examiner

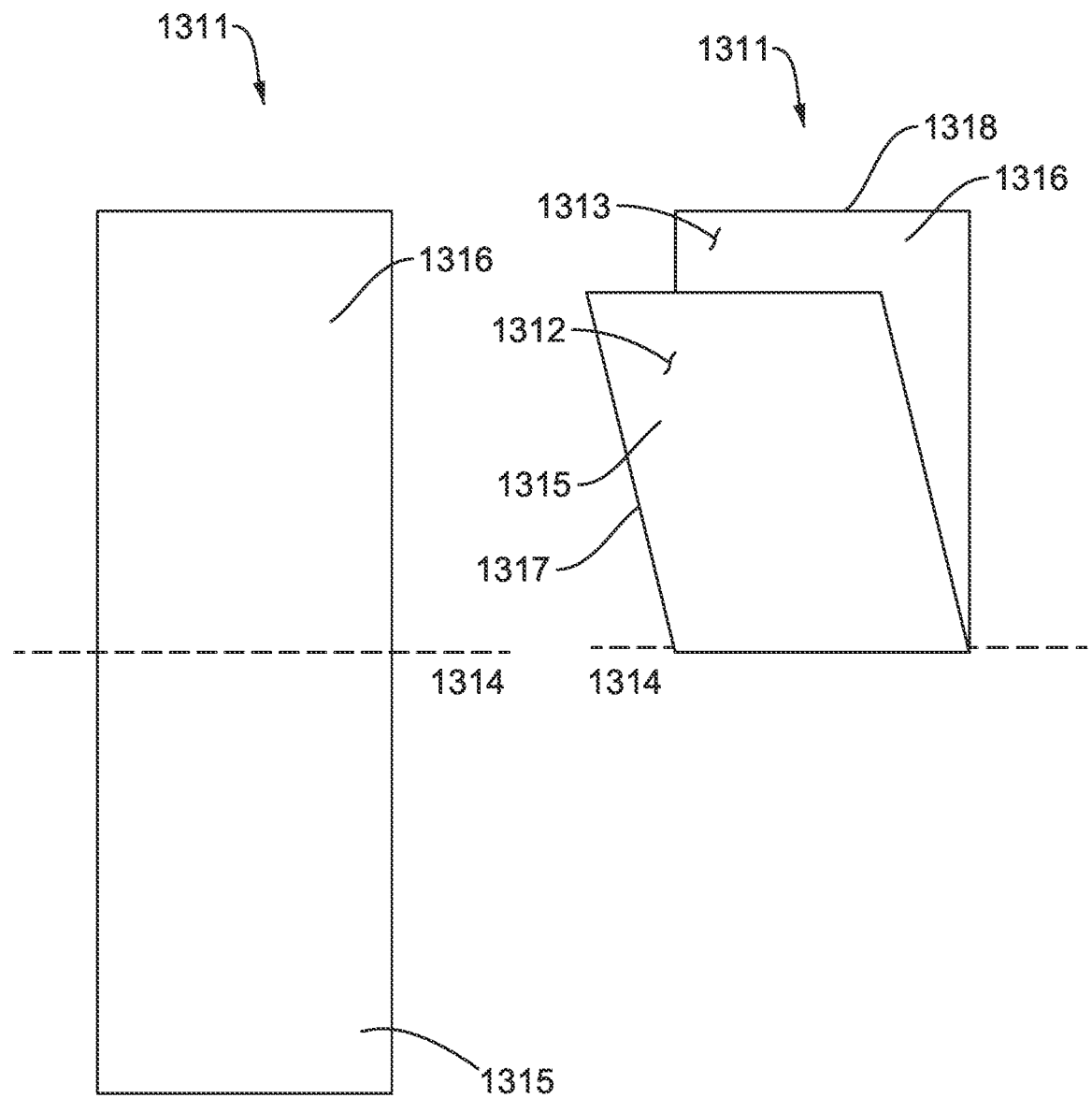

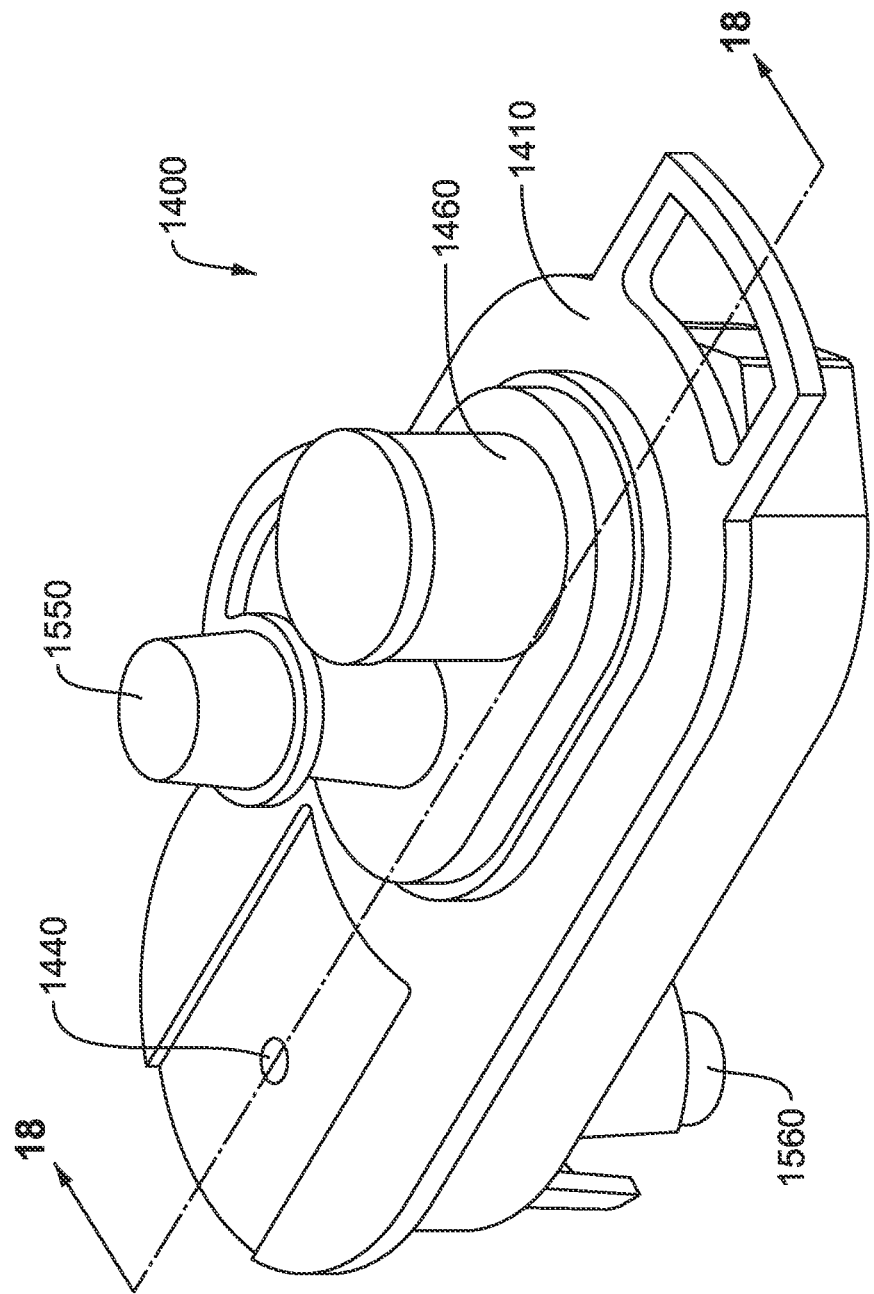

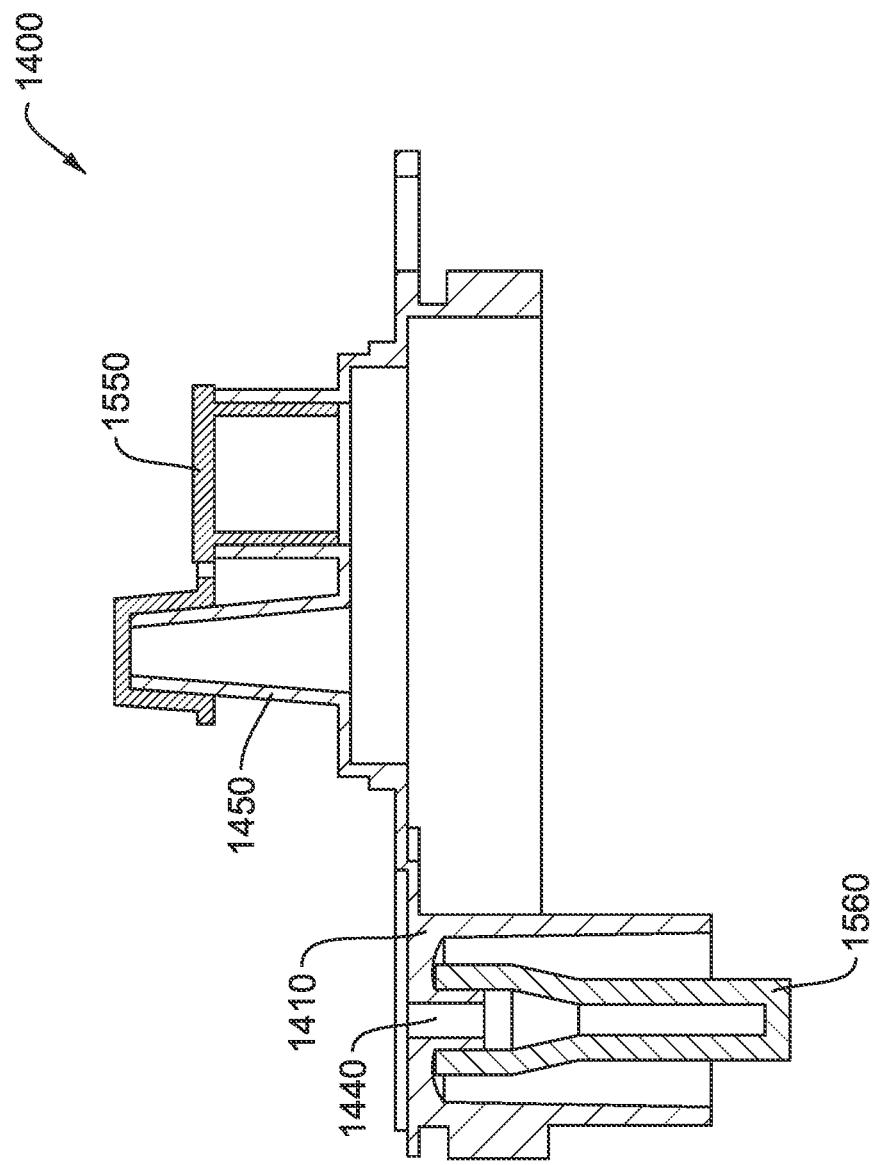

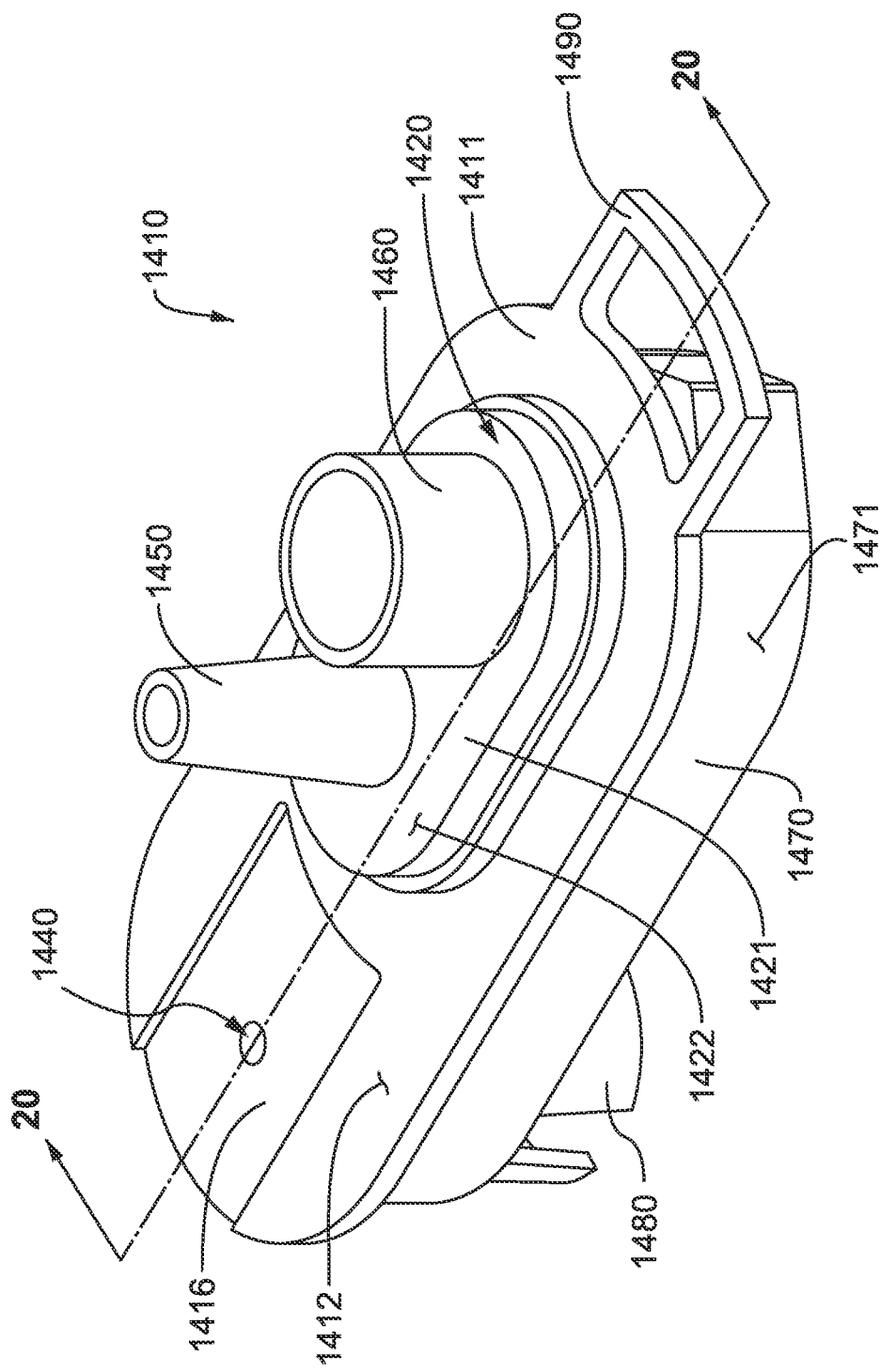

FIG. 40
FIG. 41
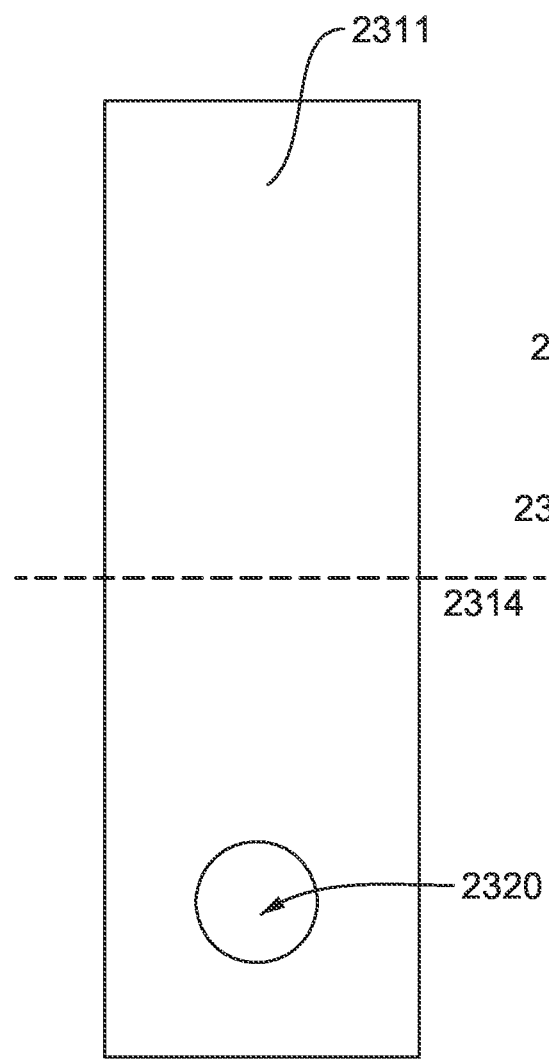
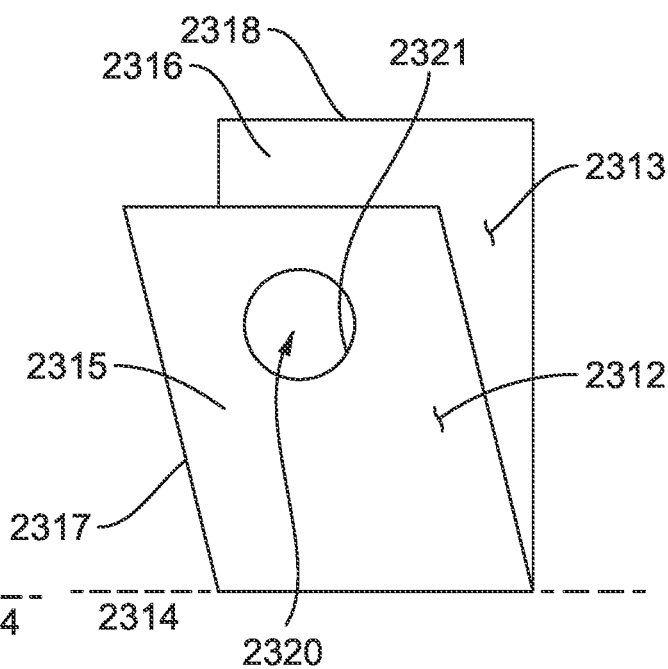

FIG. 63
FIG. 64
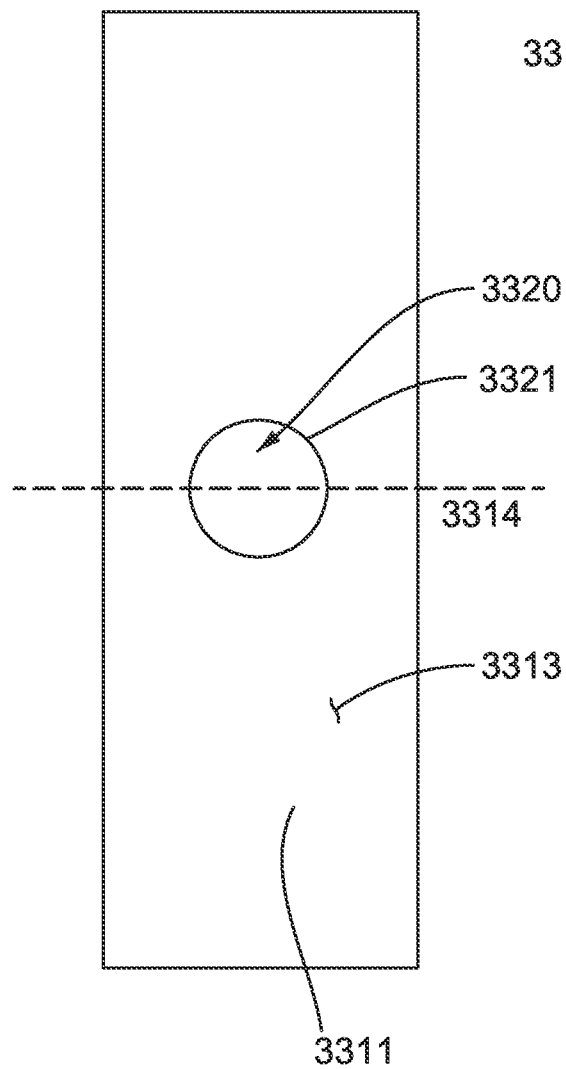
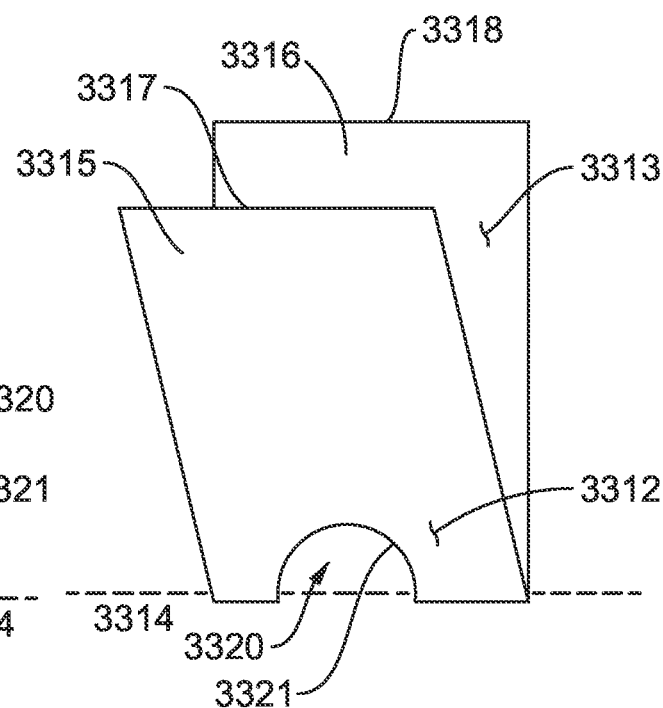

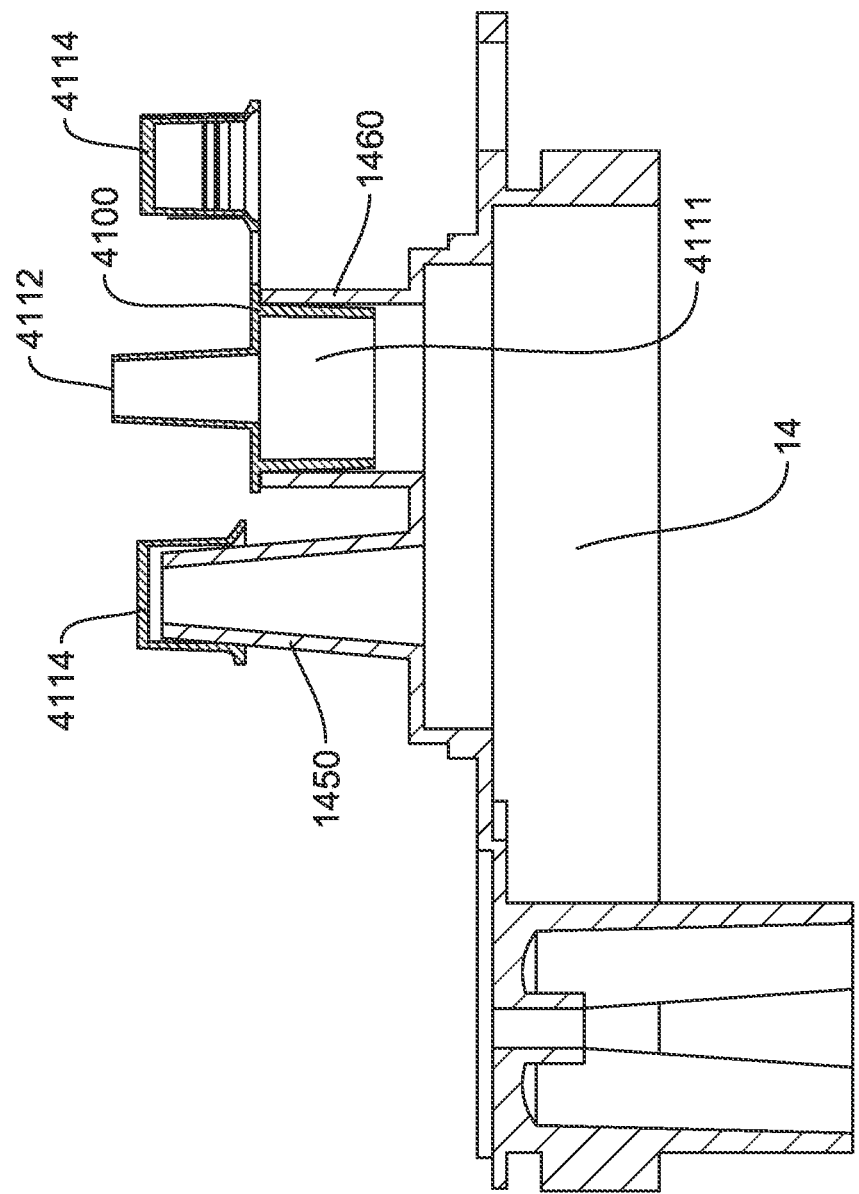

FLUID COLLECTION SYSTEMS

CROSS-REFERENCE TO RELATED APPLICATIONS

This application is a continuation of U.S. patent application Ser. No. 15/295,924, filed on Oct. 17, 2016, now abandoned, which claims priority to U.S. Provisional Patent Application No. 62/242,869, entitled "Fluid Collection Systems", filed on Oct. 16, 2015, the disclosures of which are incorporated by reference in their entireties.

BACKGROUND

Hospital operating rooms, emergency rooms, and other healthcare facilities generate a large volume of liquid waste, which may include irrigation liquids and secretions removed from a patient's body (e.g., blood and other bodily liquids). To collect and dispose of such liquid waste, suction canisters are typically used. A typical suction canister is a temporary storage container that uses suction to create a negative pressure inside the canister to drain liquids or secretions from the patient's body. After each medical procedure (e.g., surgery), the canister containing the liquid waste is transported to a utility area to be disposed of as red-bag waste or to be emptied, cleaned, and disinfected for reuse. A new or cleaned canister is then brought into the operating room for a next medical procedure.

Most conventional fluid collection systems with a liner include two components: a canister and a liner assembly. The canister is closed by a lid. The lid is attached to the liner, such that the liner assembly includes both the liner and the lid. The canister is typically cleaned after a procedure and used again, while the liner assembly is a single-use component. The liner and the lid are both discarded after a procedure. Hospitals pay for red-bag waste disposal by weight, so it is desirable to limit the material usage in the disposable components.

SUMMARY

Disclosed herein is a fluid collection system comprising a canister having a cavity and an open end; a lid, the lid sealed with the open end of the canister when the fluid collection system is in a closed position; and a fluid receptacle comprising a liner and a fitment assembly, the liner and the fitment assembly together defining a fluid chamber, wherein the fitment assembly is sealed with the lid around an opening in the lid when the fluid collection system is in the closed position.

Also disclosed herein is a fluid receptacle for use in a fluid collection system including a canister having a lid, the fluid receptacle comprising a liner having an opening; and a fitment assembly comprising a fluid port; a fluid chamber vacuum port; and a sealing surface, wherein the fitment assembly is sealed to the liner around the opening; wherein the liner and the fitment assembly together define a fluid chamber, wherein the fluid port and the fluid chamber vacuum port allow communication into and out of the fluid chamber, and wherein at least a portion of the sealing surface seals to the lid.

Also disclosed herein is a fluid collection system comprising a canister having a cavity and an open end; a lid, the lid forming a seal with a portion of the open end of the canister when the fluid collection system is in a closed position; and a fluid receptacle comprising a liner and a fitment assembly, the liner and fitment assembly together defining a fluid chamber, wherein the lid and the open end of the canister define an aperture between them when the fluid collection system is in the closed position, and wherein the fitment assembly seals around the aperture when the fluid collection system is in the closed position.

Also disclosed herein is a method of collecting fluid in a fluid collection system, the method comprising providing a fluid collection system comprising: a canister; a lid having an opening; and a fluid receptacle comprising a liner and a fitment assembly, wherein the liner and fitment assembly define a fluid chamber, and wherein the fitment assembly includes a fluid port and a fluid chamber vacuum port; forming a seal between the fitment and the lid and a seal between the canister and the lid to define an interstitial chamber; applying a vacuum to the interstitial chamber; and transmitting the vacuum from the interstitial chamber to the fluid chamber through the fluid chamber vacuum port; and drawing a fluid into the fluid chamber through the fluid port.

BRIEF DESCRIPTION OF FIGURES

FIG. 15 is a side view of the liner body used to make the liner of FIG. 14.

FIG. 16 is a side view showing how the liner body is folded to make the liner of FIG. 14.

FIG. 17 is an isometric view of a fitment assembly of the fluid collection system of FIG. 1, shown from above.

FIG. 18 is a cross-sectional view of the fitment assembly of FIG. 17 taken along line 18, shown from the side.

FIG. 19 is an isometric view of a fitment of the fitment assembly of FIG. 17, shown from above.

FIG. 40 is a side view of the liner body used to make the liner of FIG. 39.

FIG. 41 is a side view of the liner body showing how the liner body is folded to make the liner of FIG. 39.

FIG. 63 is a side view of the liner body used to make the liner of FIG. 62.

FIG. 64 is a side view showing how the liner body is folded to make the liner of FIG. 62.

FIG. 75 is a cross-sectional view of the pour spout adapter of FIG. 73 inserted into the pour spout of the fitment of FIG. 20, shown from the side.

It should be understood that the figures are diagrammatic and schematic representations of exemplary embodiments of the invention of the present disclosure, and are neither limiting nor necessarily drawn to scale.

DETAILED DESCRIPTION

Throughout this disclosure, the words "upstream" and "downstream" are used. As used herein, a first component is said to be upstream from a second component if gases or liquids flow from the first component toward the second component. Likewise, in the same scenario, the second component is considered to be downstream from the first component. For example, a vacuum source (e.g., vacuum pump) is said to be downstream from a container to which it provides the vacuum because air moves from the container toward the vacuum source.

The fluid collection systems of the present disclosure may include at least three components: a canister, a lid, and a liner assembly. The canister and the lid may be reusable components that are cleaned after a procedure and used again. The liner assembly is typically a single-use component that is disposed and replaced after each procedure. Therefore, it is desirable to minimize the material usage in the liner assembly. The liner assembly may include a liner and a fitment assembly. The fitment assembly may be smaller compared to the lid, which minimizes the material usage in the liner assembly.

During use, the fluid collection systems of the present disclosure may include two chambers: a fluid chamber and an interstitial chamber. The interstitial chamber may be substantially enclosed by the canister, the lid, the liner and the fitment assembly. Applying a vacuum to the interstitial chamber may cause the liner to be drawn toward the interior walls of the canister. The fluid chamber may be substantially enclosed by the liner and the fitment assembly, which optionally includes a gland that couples the liner to the fitment. Applying a vacuum to the fluid chamber may draw fluid into the fluid chamber.

Figure 1:
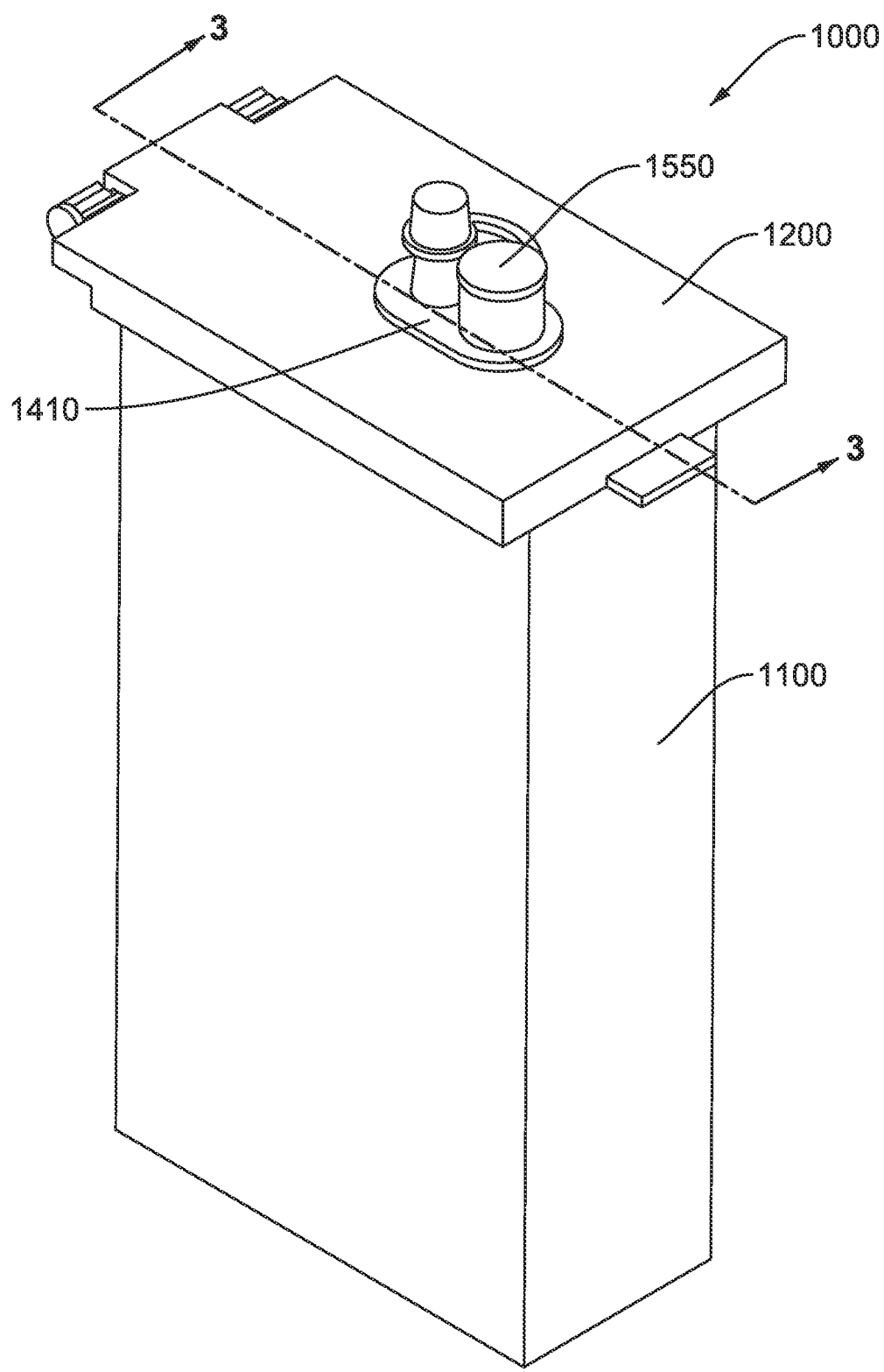
FIG. 1 is an isometric view of a first embodiment of the fluid collection system, shown from above in a closed position, according to certain aspects of the present application.
Figure 2:
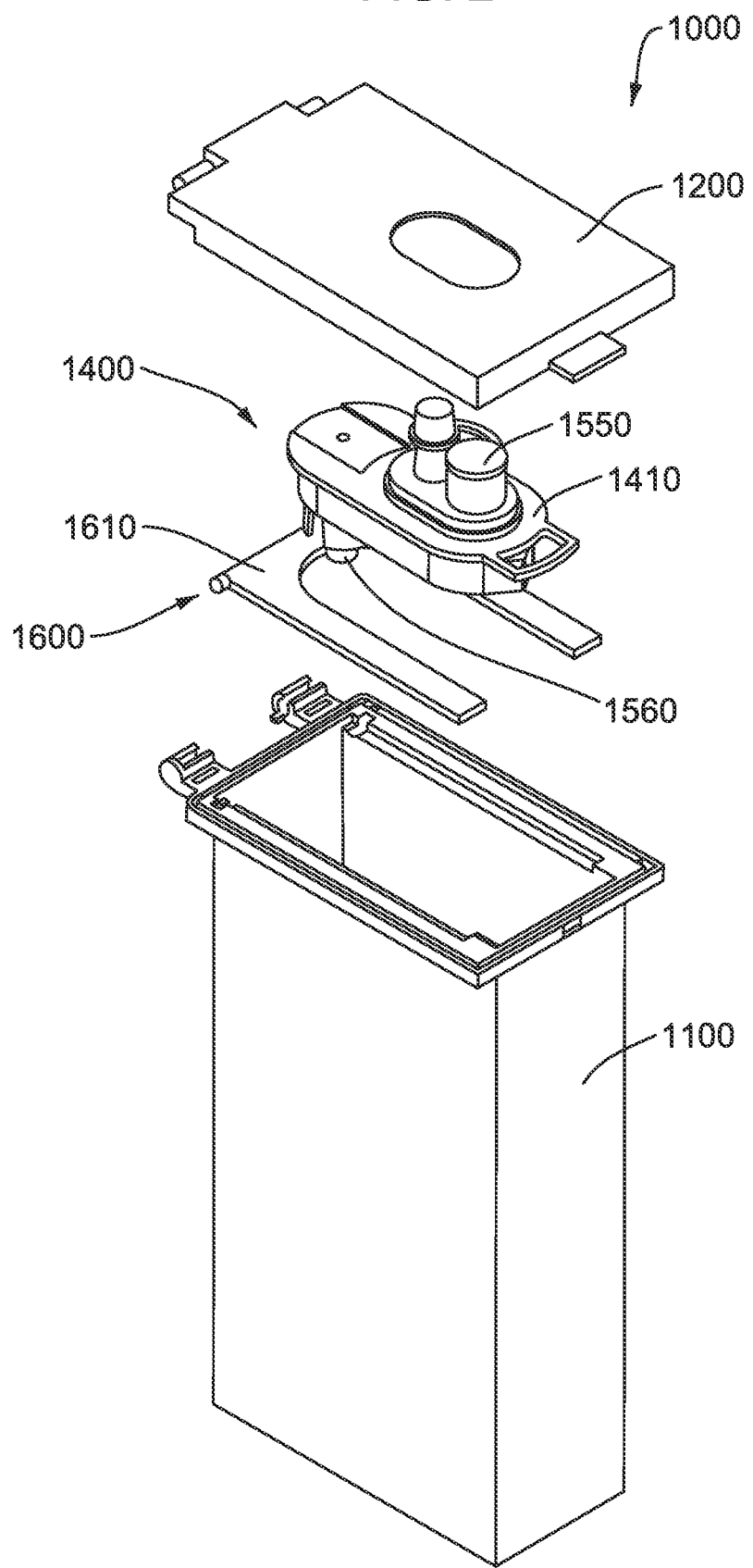
FIG. 2 is an exploded isometric view of the fluid collection system of FIG. 1, shown from above. The liner is not shown in this figure.
Figure 3:
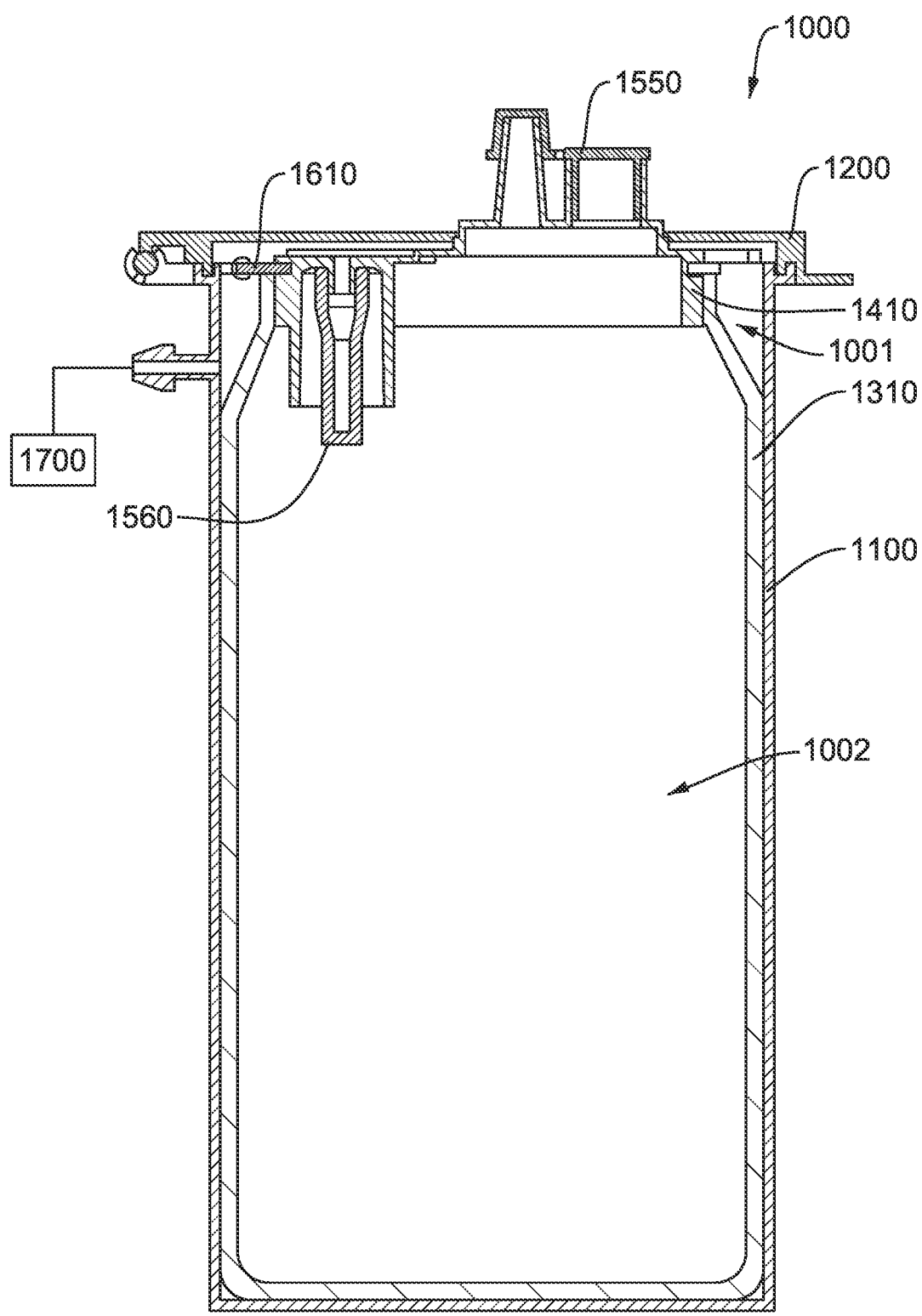
FIG. 3 is a cross-sectional view of the fluid collection system of FIG. 1 taken along line 3, shown from the side in a closed position.
Figure 11:
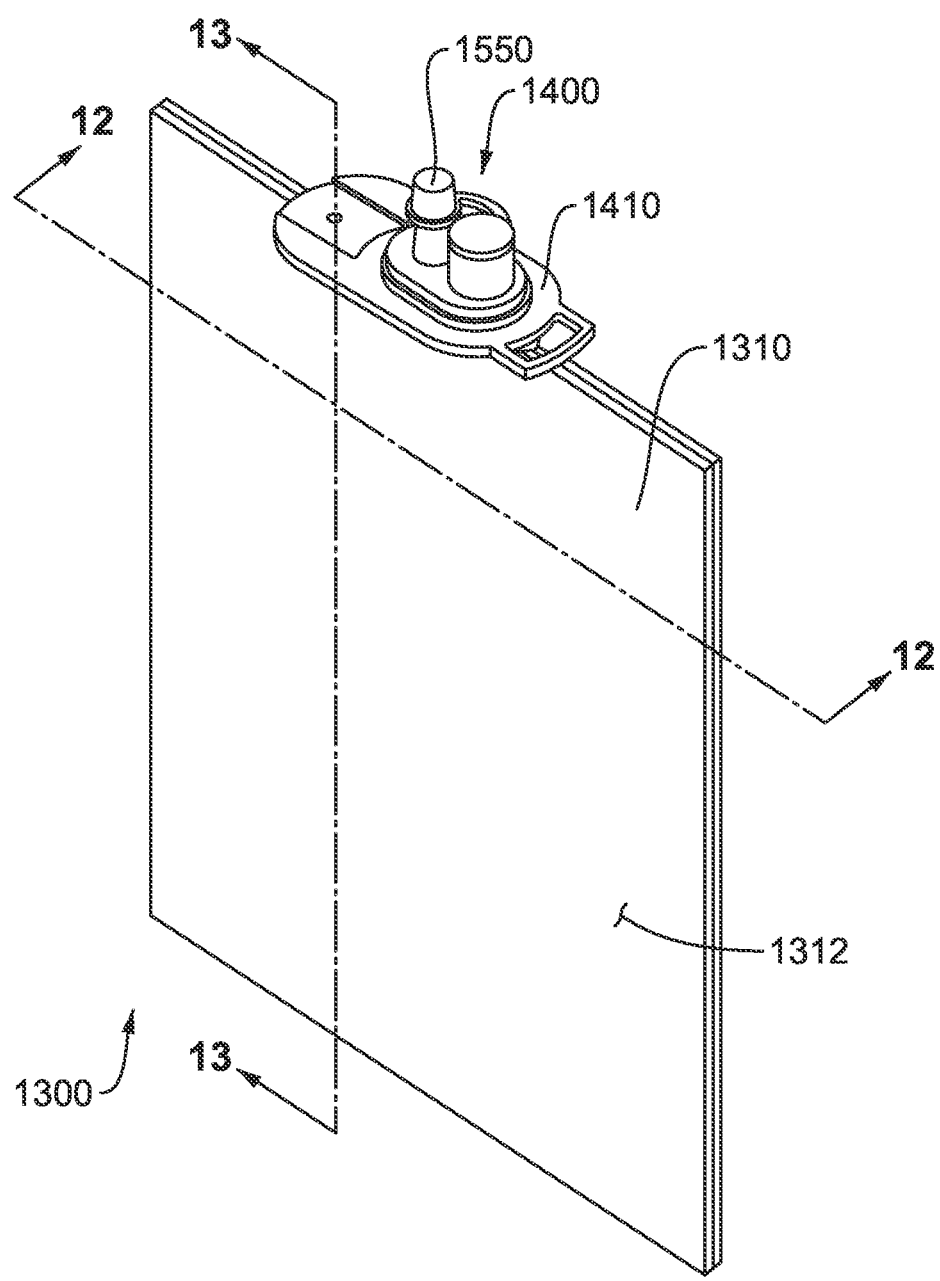
FIG. 11 is an isometric view of a liner assembly of the fluid collection system of FIG. 1, shown from above.
Figure 12:
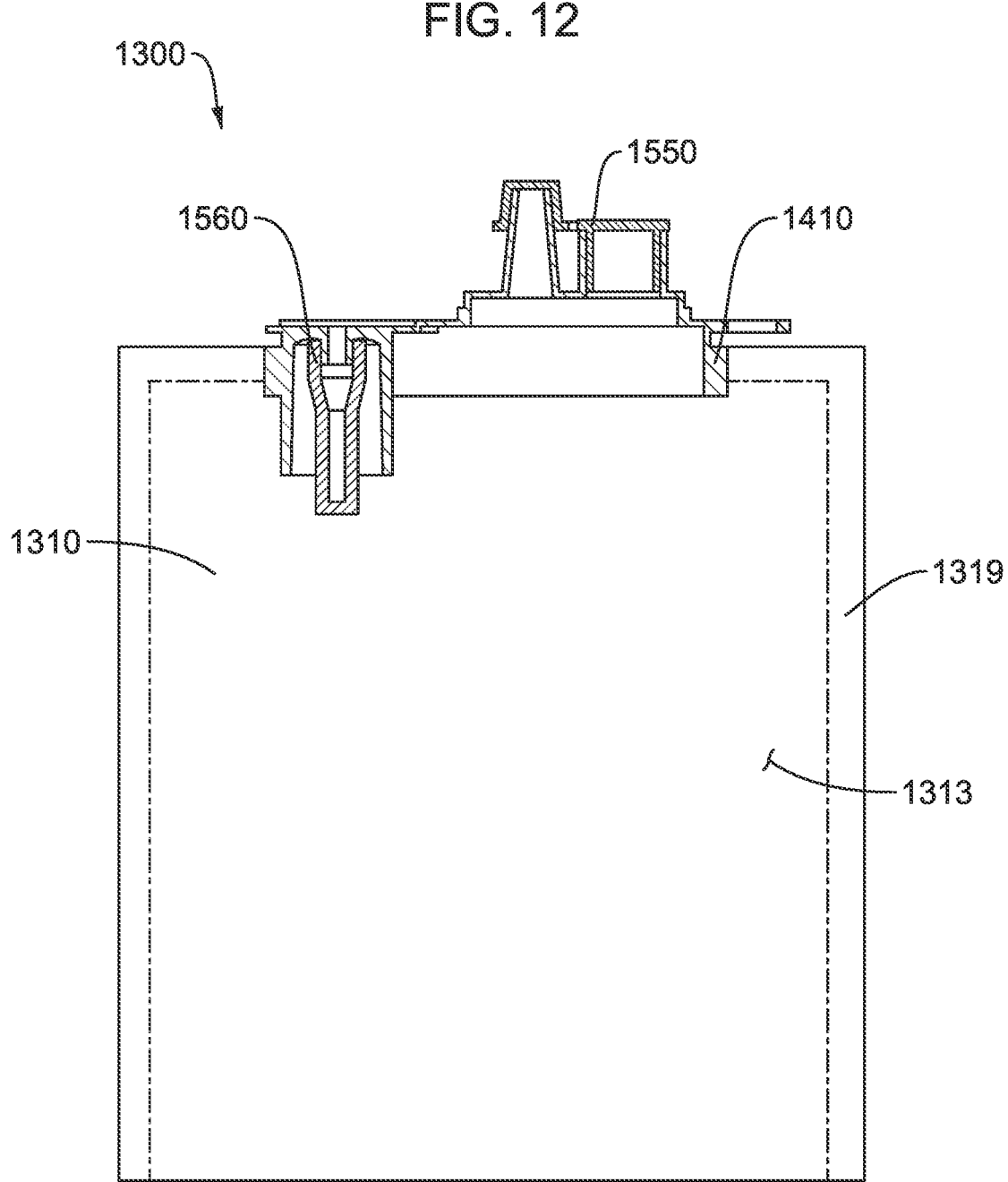
FIG. 12 is a cross-sectional view of the liner assembly of FIG. 11 taken along line 12, shown from the side.
Figure 13:
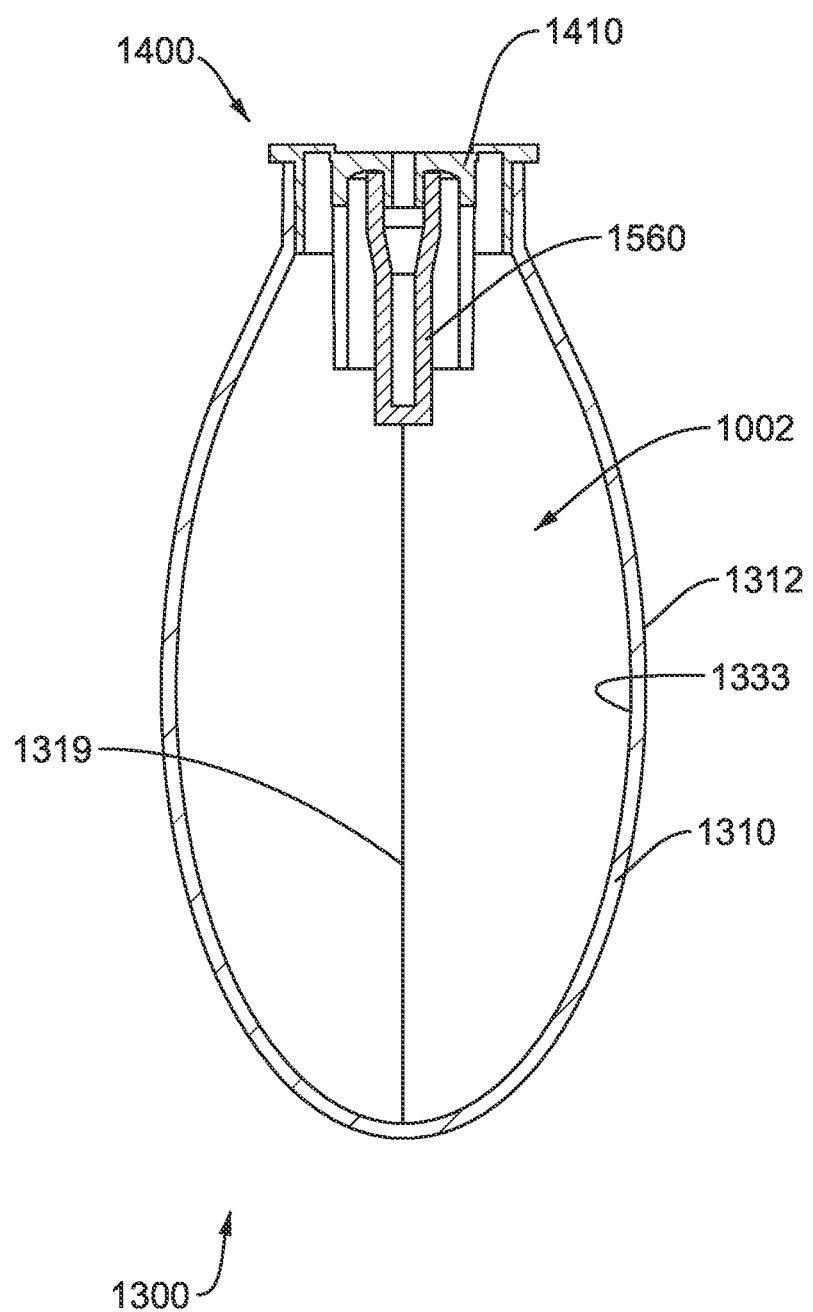
FIG. 13 is a cross-sectional view of the liner assembly of FIG. 11 taken along line 13, shown from the front.

A first embodiment of the fluid collection system 1000 is shown in FIGS. 1-3 and may include a canister 1100, a lid 1200, a liner 1310 (not shown in FIG. 2), a fitment 1410, a cap assembly 1550, a filter 1560, and an optional fitment support 1600. Together, the fitment 1410, the filter 1560, and the cap assembly 1550 form a fitment assembly 1400, as shown in FIGS. 17-18. Together, the fitment assembly 1400 and the liner 1310 form a liner assembly 1300, as shown in FIGS. 11-13. With respect to this embodiment, the terms "upper," "lower," "top," "bottom," "above," and "below" are discussed as shown in FIG. 3.

When the fluid collection system 1000 is in the closed position as shown in FIGS. 1 and 3, two chambers are formed: a fluid chamber 1002 and an interstitial chamber 1001. The fluid chamber 1002 is substantially enclosed by the liner 1310 and the fitment assembly 1400. The interstitial chamber 1001 is substantially enclosed by the canister 1100, the lid 1200, the liner 1310, and the fitment assembly 1400. A filter 1560 in the fitment assembly 1400 may separate the fluid chamber 1002 from the interstitial chamber 1001.

Figure 4:
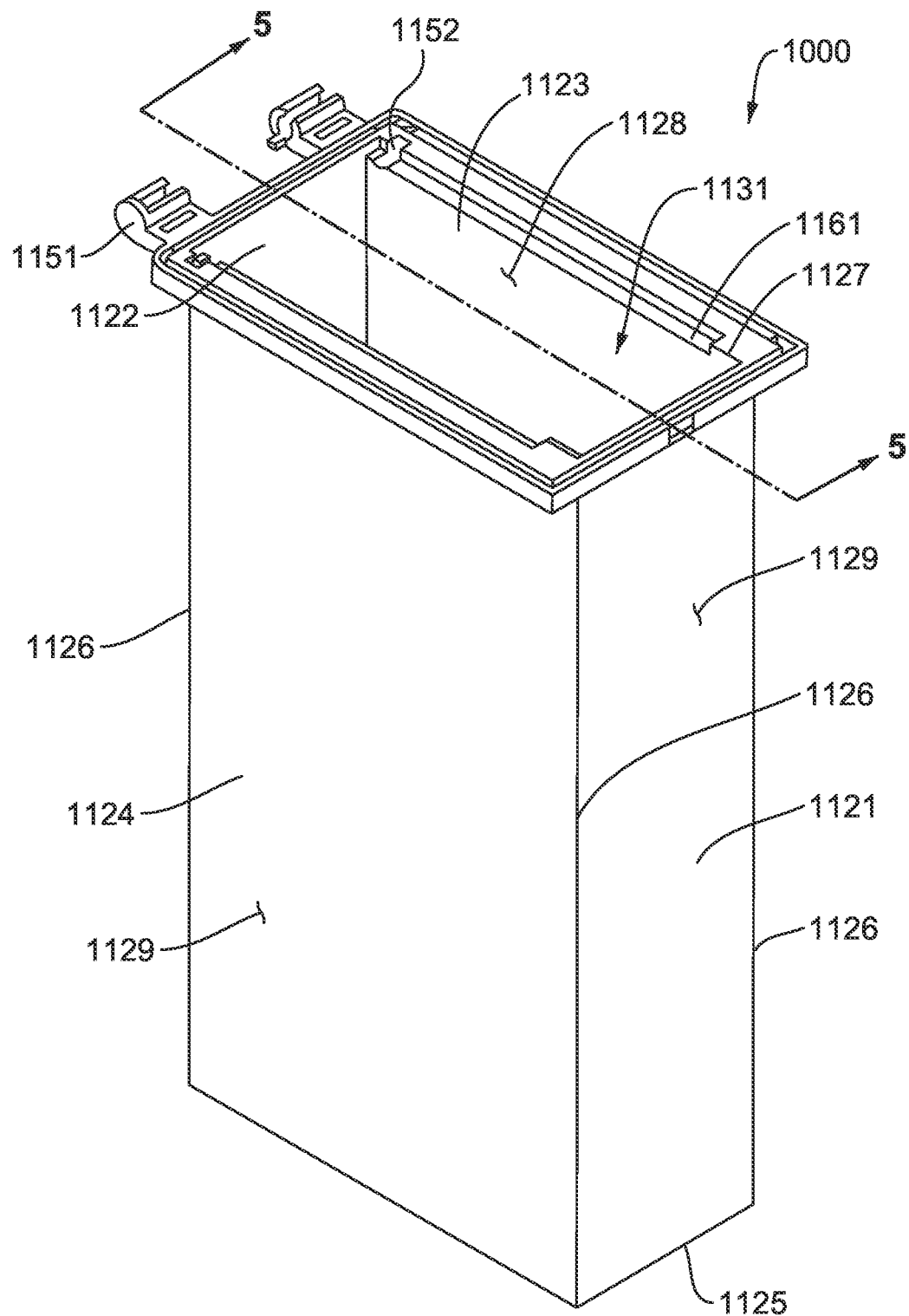
FIG. 4 is an isometric view of a canister of the fluid collection system of FIG. 1, shown from above.
Figure 5:
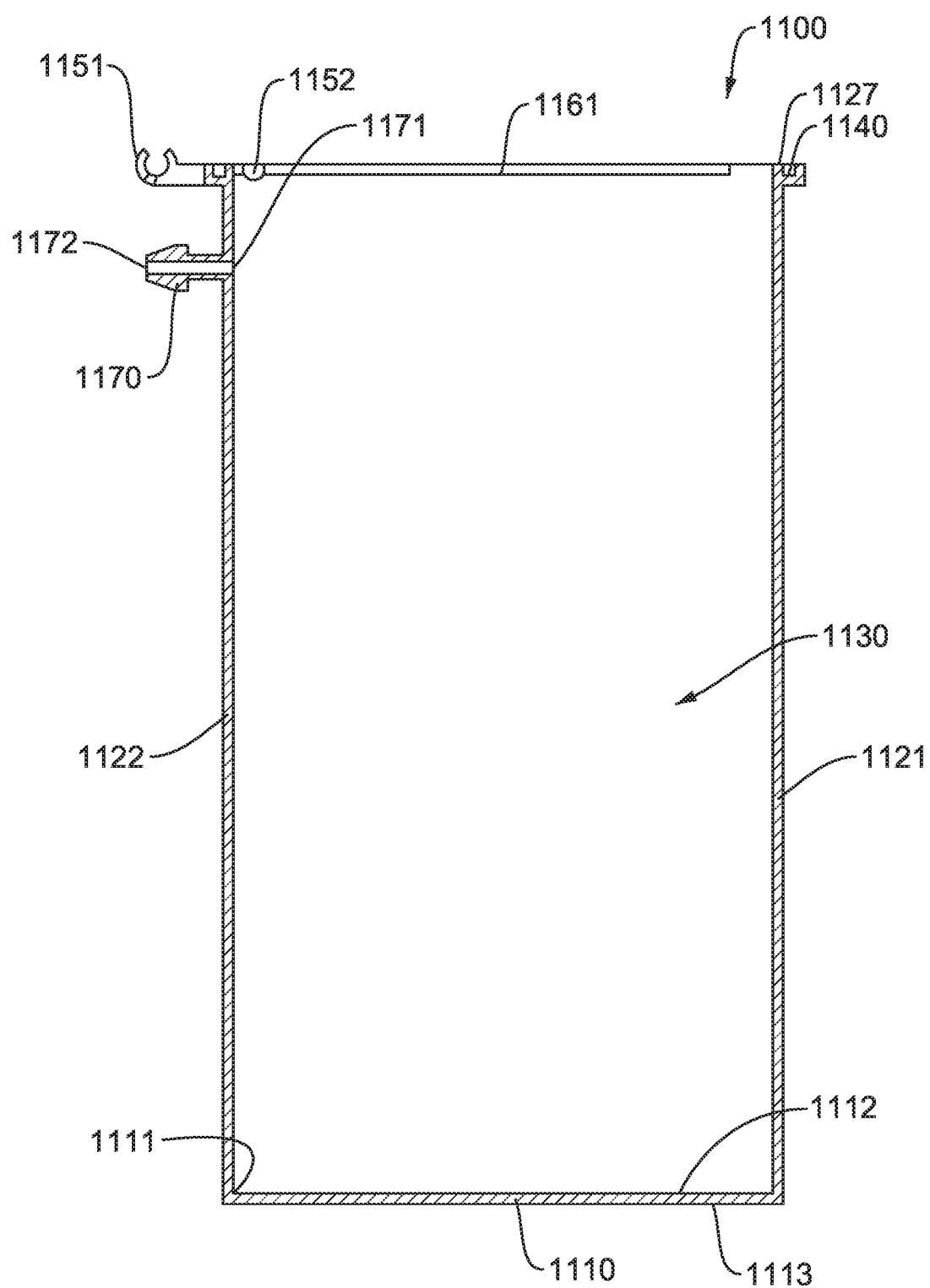
FIG. 5 is a cross-sectional view of the canister of FIG. 4 taken along line 5, shown from the side.

FIGS. 4-5 show the canister 1100 of the first embodiment, the canister 1100 having a bottom wall 1110, a first side wall 1121, a second side wall 1122, a third side wall 1123, and a fourth side wall 1124. The bottom wall 1110 has an interior surface 1112, an exterior surface 1113, and four ends 1111. The side walls 1121, 1122, 1123, 1124 of the canister 1100 each have a bottom end 1125, two side ends 1126, a top end 1127, an interior surface 1128, and an exterior surface 1129. The bottom end 1125 of each side wall is connected to an end 1111 of the bottom wall 1110. Each side end 1126 of each side wall is connected to a side end 1126 of an adjacent side wall.

In embodiments of canisters 1100 with four side walls, such as those shown in FIGS. 4-5, the first side wall 1121 may be opposite the second side wall 1122 and adjacent to the third side wall 1123 and the fourth side wall 1124, and the second side wall 1122 may also be adjacent to the third side wall 1123 and the fourth side wall 1124. However, the canister 1100 may be configured to have any number of side walls.

During use, the exterior surface 1113 of the bottom wall 1110 and the exterior surface 1129 of the side walls of the canister 1100 are exposed to the environment. Together, the interior surface 1112 of the bottom wall 1110 and the interior surface 1128 of the side walls form a cavity 1130 in the canister 1100. The cavity 1130 may have an open end such that the canister 1100 has an opening 1131 opposite the bottom wall 1110. Together, the top ends 1127 of the side walls of the canister 1100 may surround the opening 1131 of the cavity 1130, and may form the open end of the canister 1100. The opening 1131 may lie in the same plane as the top ends 1127 of the side walls. A groove 1140 may be included at the top end 1127 of each side wall. The groove 1140 surrounds the opening 1131.

The canister 1100 may include an interstitial vacuum port 1170 having a vacuum source end 1172 that opens on the exterior of the canister 1100 and a cavity end 1171 that opens into the cavity 1130 of the canister 1100. In FIG. 5, the interstitial vacuum port 1170 is positioned on the second side wall 1122 of the canister 1100. However, the interstitial vacuum port 1170 could be positioned on any of the side walls 1121, 1122, 1123, 1124 of the canister 1100, or on the lid 1200.

Figure 6:
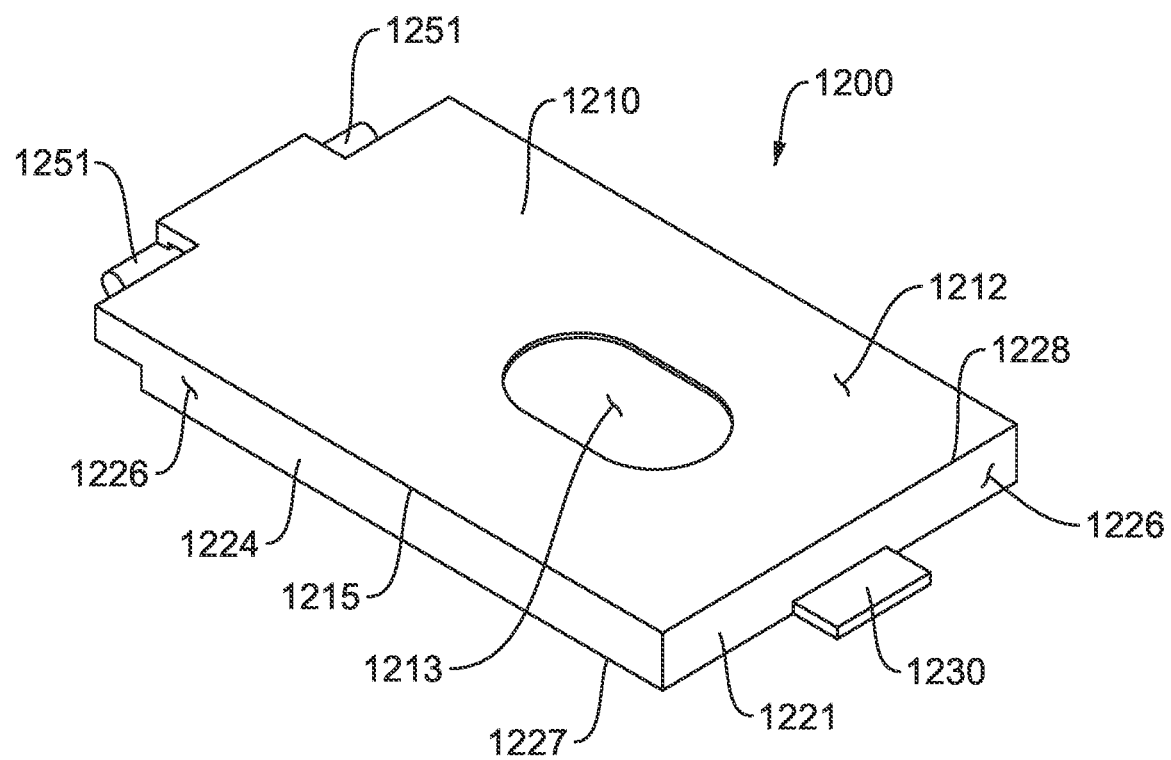
FIG. 6 is an isometric view of a lid of the fluid collection system of FIG. 1, shown from above.
Figure 7:
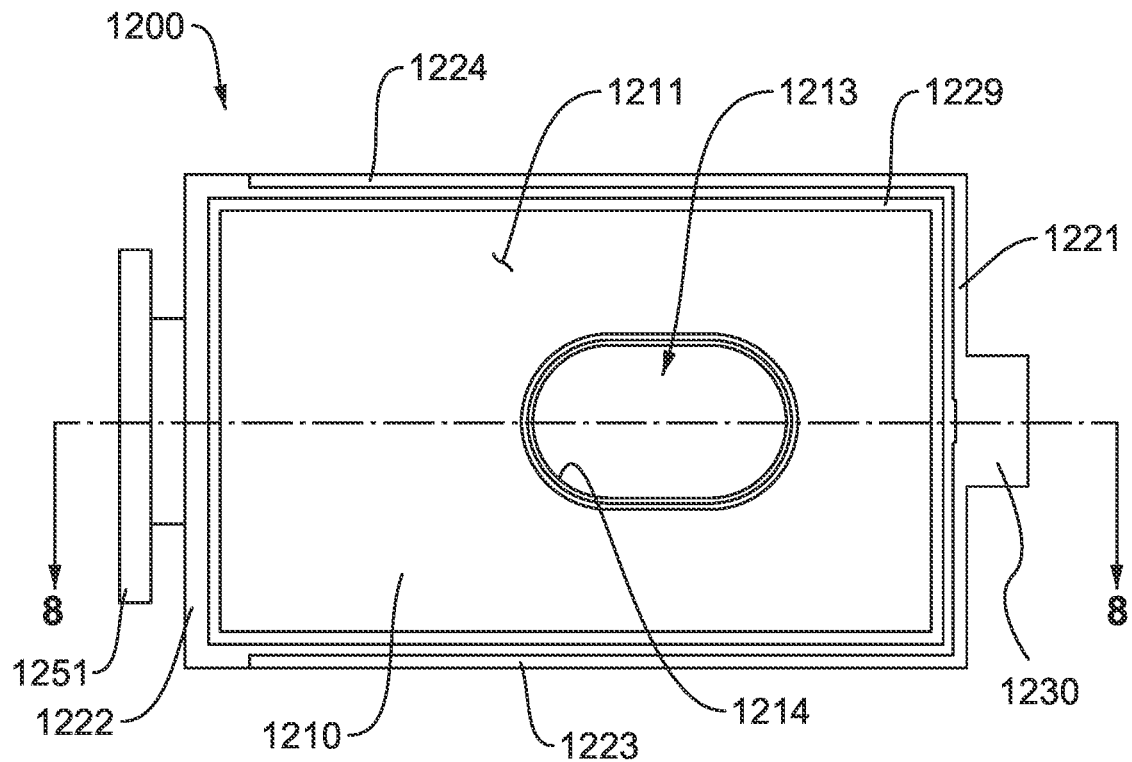
FIG. 7 is a bottom view of the lid of FIG. 6.
Figure 8:
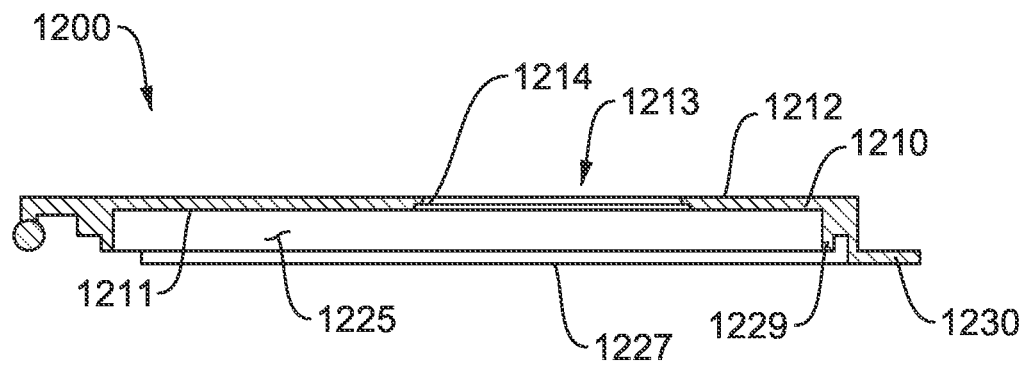
FIG. 8 is a cross-sectional view of the lid of FIG. 7, taken along line 8, shown from the side.

The fluid collection system 1000 also includes a lid 1200 as shown in FIGS. 6-8. The lid 1200 has an upper wall 1210, a first side wall 1221, a second side wall 1222, a third side wall 1223, and a fourth side wall 1224. The upper wall 1210 of the lid 1200 has an interior surface 1211, an exterior surface 1212, and four ends 1215. The side walls 1221, 1222, 1223, 1224 each have a bottom end 1227, a top end 1228, an interior surface 1225 and an exterior surface 1226. The top end 1228 of each side wall is connected to an end 1215 of the upper wall 1210. A rib 1229 may protrude from the bottom end 1227 of the side walls of the lid 1200. The lid 1200 may also have one or more tabs 1230 extending from the exterior surface 1226 of one or more of the side walls 1221, 1222, 1223, 1224 to facilitate the opening and/or closing of the lid 1200.

In embodiments of lids 1200 with four side walls, such as those shown in FIGS. 6-8, the first side wall 1221 may be opposite the second side wall 1222 and adjacent to the third side wall 1223 and the fourth side wall 1223, and the second side wall 1222 may also be adjacent to the third side wall 1223 and the fourth side wall 1224. However, the lid 1200 may be configured to have any number of side walls.

When the lid 1200 is in a closed position, the exterior surface 1212 of the upper wall 1210 is exposed to the environment and the interior surface 1211 of the upper wall 1210 faces the cavity 1130 of the canister 1100, as shown in FIGS. 1 and 3.

An opening 1213 may be included in the upper wall 1210 of the lid 1200. The opening 1213 has an inner surface 1214. The lid 1200 may be placed over the opening 1131 of the cavity 1130 of the canister 1100 to partially close the opening 1131 of the cavity 1130. The opening 1213 in the upper wall 1210 of the lid 1200 enables communication into and out of the cavity 1130 of the canister 1100. The rib 1229 on the bottom end 1227 of the side walls 1221, 1222, 1223, 1224 surrounds the opening 1213 in the upper wall 1210 of the lid 1200.

When the lid 1200 is in a closed position, the canister 1100 and the lid 1200 are in sealing engagement with one another. The first side wall 1121 of the canister 1100 mates with the first side wall 1221 of the lid 1200. Likewise, the second, third, and fourth side walls 1122, 1123, 1124 of the canister 1100 mate with the second, third, and fourth side walls 1222, 1223, 1224 of the lid 1200, respectively. The rib 1229 on the lid 1200 may be inserted into the groove 1140 on the canister 1100 to create an interference fit. Together, the groove 1140 on the canister 1100 and the rib 1229 on the lid 1200 cooperate to enable sealing engagement between the canister 1100 and the lid 1200.

The canister 1100 and the lid 1200 may be coupled via a first hinge. The lid 1200 may have a first hinge element 1251 and the canister 1100 may have a first hinge element 1151.

When assembled, the first hinge element 1251 on the lid 1200 and the first hinge element 1151 on the canister 1100 cooperate to form the first hinge. The first hinge element 1151 on the canister 1100 may be located proximate to the top end 1127 of the exterior surface 1129 of the second side wall 1122. The first hinge element 1251 on the lid 1200 may be located proximate to the second side wall 1222 of the lid 1200.

Figure 25:
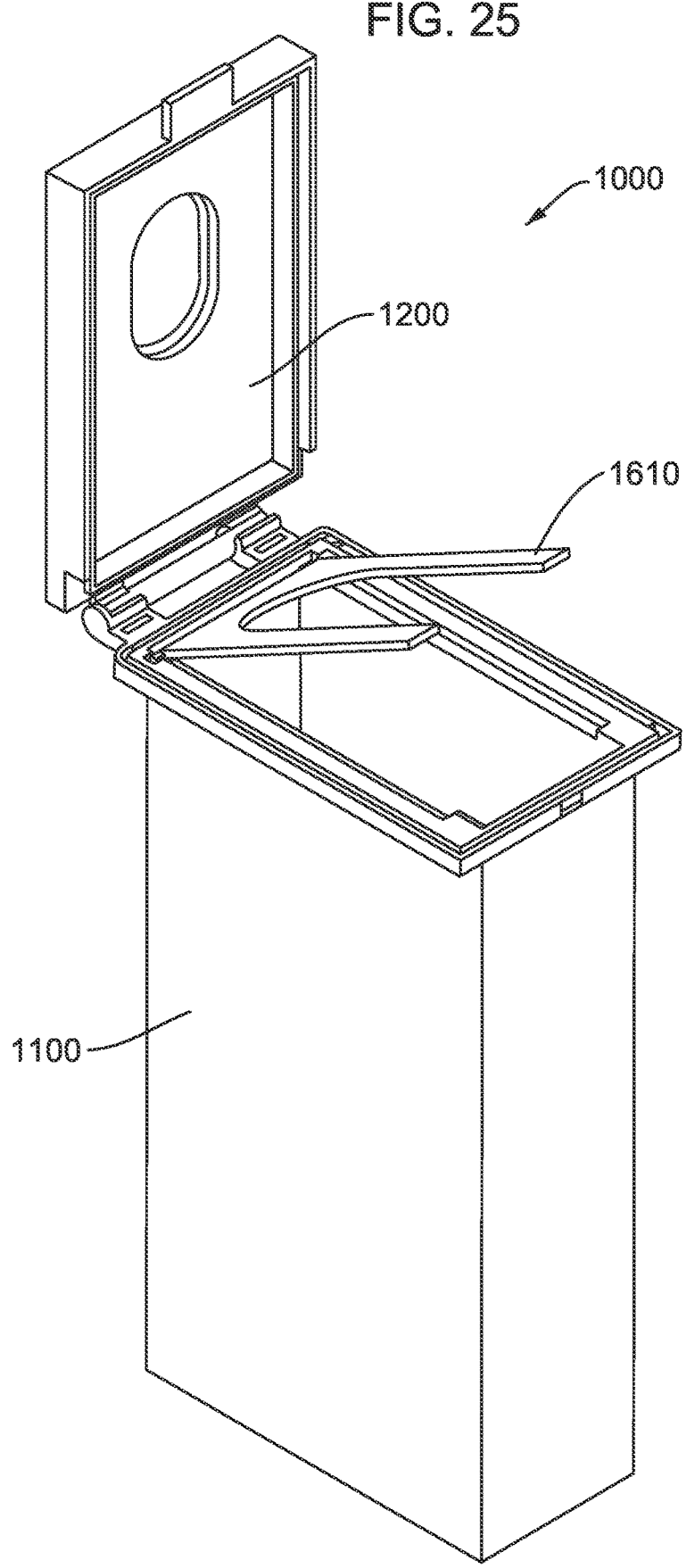
FIG. 25 is an isometric view of the fluid collection system of FIG. 1, shown from above in the open position.

The lid 1200 is moveable between a closed position shown in FIGS. 1 and 3 and an open position shown in FIG. 25. In the closed position, the lid 1200 and the canister 1100 are in sealing engagement with one another, and the lid 1200 partially closes the opening 1131 of the canister 1100. In the open position, the lid 1200 and the canister 1100 are not in sealing engagement with one another, and the lid 1200 does not cover the opening 1131 of the canister 1100. The user may use the tab 1230 to help move the lid 1200 between the open position and the closed position.

The fluid collection system 1000 also includes a liner assembly 1300 as shown in FIGS. 11-13. The liner assembly 1300 (i.e. fluid receptacle) includes a liner 1310 and a fitment assembly 1400 which cooperate to substantially enclose a fluid chamber 1002.

Figure 14:
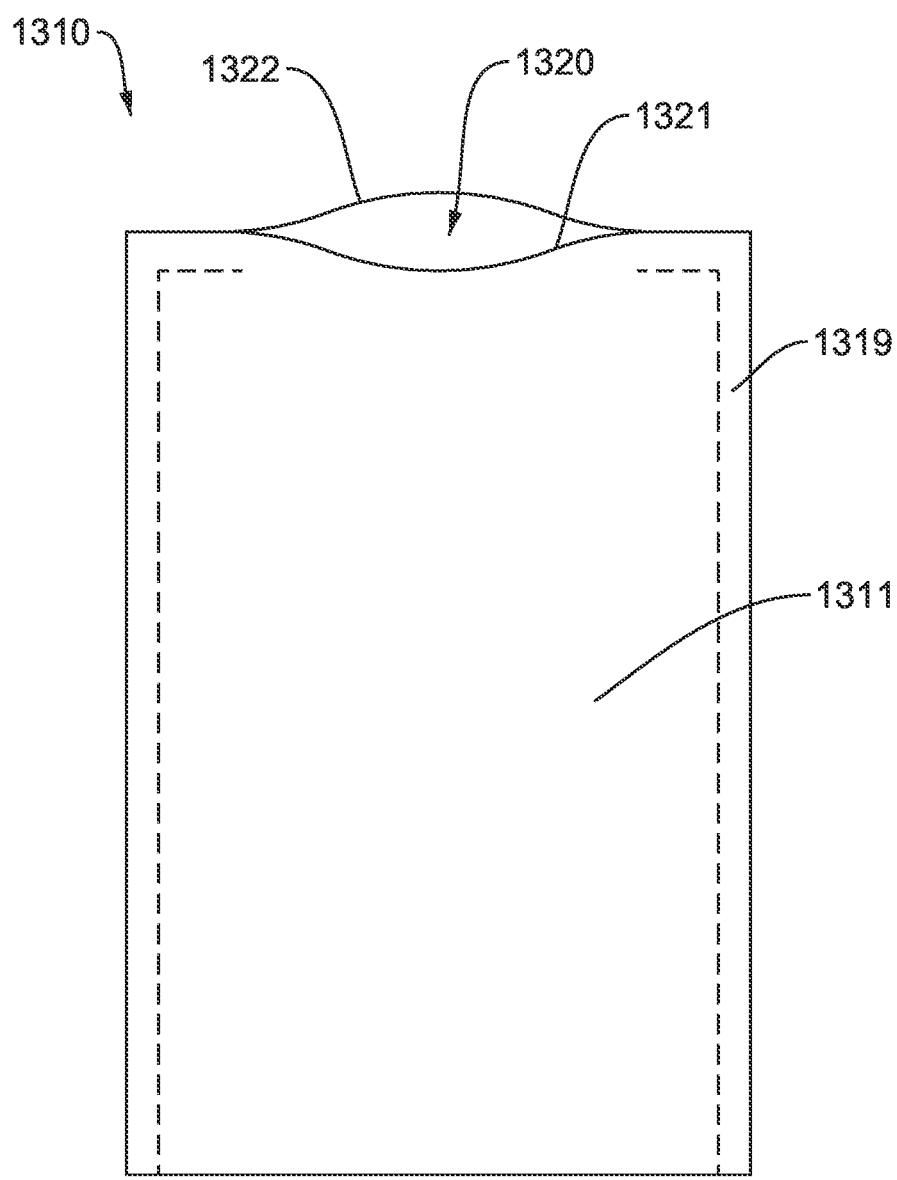
FIG. 14 is a side view of the liner of the liner assembly of FIG. 11.

The liner 1310 of the first embodiment is shown in FIG. 14. FIG. 15 shows the body 1311 of the liner 1310 before the liner 1310 is assembled. The body 1311 of the liner 1310 is made of a thin-walled material. The body 1311 has been folded along a fold line 1314 to create a first panel 1315 having four ends and a second panel 1316 having four ends. The first panel 1315 and the second panel 1316 are joined along one end by the fold, as shown in FIG. 16. The remaining three ends of the first panel 1315 form a first periphery 1317, and the remaining three ends of the second panel 1316 form a second periphery 1318. The first panel 1315 and the second panel 1316 are joined to one another by a seal 1319 extending along at least a portion of the first periphery 1317 and at least a portion of the second periphery 1318 as shown in FIG. 14. The seal 1319 extends from the dashed line in FIG. 14 toward the first periphery 1317 and the second periphery 1318 of the liner 1310. The seal may be about ⅜" wide, or may have a different width as long as an appropriate seal strength is maintained when the liner 1310 is exposed to vacuum and/or contains fluid.

The liner 1310 of the first embodiment has an opening 1320 in the seal 1319 of the liner 1310. At the opening 1320 in the seal 1319, an unsealed portion 1321 of the first periphery 1317 of the first panel 1315 and an unsealed portion 1322 of the second periphery 1318 of the second panel 1316 are not joined to one another. The fitment 1410, described below, is inserted into the opening 1320 in the seal 1319 of the liner 1310.

As shown in FIG. 3, the liner 1310 is positioned in the cavity 1130 of the canister 1100. The liner 1310 has a canister-facing surface 1312 and a fluid chamber surface 1313, as shown in FIG. 13. When the liner assembly 1300 is ready for use, the liner 1310 is oriented such that the canister-facing surface 1312 is on the outside (and may be facing the interior surface 1112 of the bottom wall 1110 and the interior surface 1128 of the side walls 1121, 1122, 1123, 1124 of the canister 1100 when inserted into the canister 1100) and the fluid chamber surface 1313 is on the inside.

A fitment assembly 1400 of the first embodiment is shown in FIGS. 17-18. The fitment assembly 1400 includes a fitment 1410, a filter 1560, and a cap assembly 1550. The fitment assembly 1400 also includes a fluid port 1450, a pour spout 1460, and a fluid chamber vacuum port 1440 which may be located on the fitment 1410.

Figure 20:
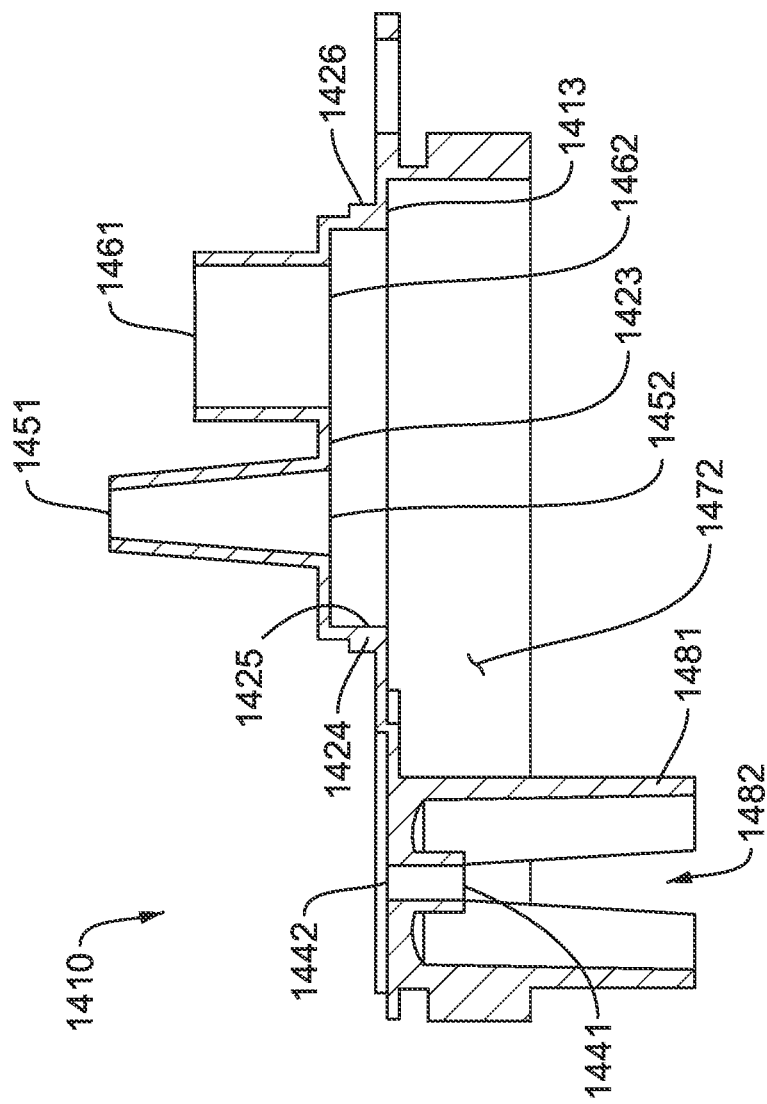
FIG. 20 is a cross-sectional view of the fitment of FIG. 19 taken along line 20, shown from the side.

The fitment 1410 is shown in FIGS. 19-20. A fluid port 1450 on the fitment 1410 and a pour spout 1460 on the fitment 1410 allow fluid to enter and exit the fluid chamber 1002. A fluid chamber vacuum port 1440 on the fitment 1410 allows a vacuum to be applied to the fluid chamber 1002. Preferably, the fluid chamber vacuum port 1440 allows a vacuum in the interstitial chamber 1001 to be transmitted to the fluid chamber 1002. The fitment 1410 may also have a handle 1490 attached to the base 1411. The handle 1490 may be positioned near an end of the fitment 1410 which includes the fluid port 1450 and the pour spout 1460. The handle 1490 assists with removal of the liner assembly 1300 from the canister 1100 and/or from the optional fitment support 1600. The fitment 1410 preferably has an elongated shape, which may help the user to orient the fitment 1410 properly in the canister 1100 and/or fitment support 1600.

The fitment 1410 includes a base 1411 having an upper surface 1412 and a lower surface 1413. When the fitment 1410 is positioned as shown in FIG. 3, the upper surface 1412 of the base 1411 faces the lid 1200, and the lower surface 1413 of the base 1411 faces the fitment support 1600 (if present) and the bottom wall 1110 of the canister 1100.

A protrusion 1420 extends from the upper surface 1412 of the base 1411 of the fitment 1410. The protrusion 1420 has an upper wall 1421 connected to the upper surface 1412 of the base 1411 by a side wall 1424. The upper wall 1421 has a lower surface 1423 that forms part of the wall of the fluid chamber 1002, and an upper surface 1422 that is exposed to the environment. The protrusion 1420 also has a side wall 1424 with an inner surface 1425 and an outer surface 1426 opposite the inner surface 1425. The inner surface 1425 of the side wall 1424 of the protrusion 1420 forms part of the wall of the fluid chamber 1002. The fitment assembly 1400 may have a sealing surface that seals to the lid 1200. The outer surface 1426 of the side wall 1424 of the protrusion 1420 may be a sealing surface that sealingly engages the inner surface 1214 of the opening 1213 in the lid 1200. The side wall 1424 of the protrusion 1420 is shown as having a series of steps, but could also be one continuous wall extending from the base 1411 to the upper wall 1421 of the protrusion 1420.

A curved rib 1470 protrudes from the lower surface 1413 of the fitment 1410. The rib 1470 may be substantially perpendicular to the lower surface 1413 of the fitment 1410. The rib 1470 may surround at least a portion of the lower surface 1413 including the openings of the fluid chamber vacuum port 1440, fluid port 1450, and pour spout 1460. The portion of the lower surface 1413 that is surrounded by the rib 1470 forms part of the wall of the fluid chamber 1002. The rib 1470 has an inner surface 1472 that forms part of the wall of the fluid chamber 1002 and an outer surface 1471 opposite the inner surface 1472. One or more longitudinal ribs (not shown) may be provided on the outer surface 1471 of the rib 1470 to improve the strength of the seal between the fitment 1410 and the liner 1310. These longitudinal ribs may be substantially parallel to the base 1411 of the fitment 1410.

The fitment 1410 and the liner 1310 are in sealing engagement with one another. The fitment 1410 and the liner 1310 are coupled by inserting the rib 1470 of the fitment 1410 into the opening 1320 in the seal 1319 of the liner 1310. The outer surface 1471 of the rib 1470 is in sealing engagement with the fluid chamber surface 1313 of the liner 1310 at the opening 1320 of the seal 1319 of the liner 1310. More specifically, the unsealed portion 1321 of the first periphery 1317 of the liner 1310 is sealed to a portion of the outer surface 1471 of the rib 1470 on the fitment 1410.

Likewise, the unsealed portion 1322 of the second periphery 1318 of the liner 1310 is sealed to a portion of the outer surface 1471 of the rib 1470 on the fitment 1410.

When moving the fluid collection system 1000 to the closed position, the protrusion 1420 on the fitment 1410 is inserted into the opening 1213 in the upper wall 1210 of the lid 1200. An interference fit may be formed between the inner surface 1214 of the opening 1213 in the lid 1200 and the outer surface 1426 of the side wall 1424 of the fitment 1410. Together, the outer surface 1426 of the side wall 1424 of the fitment 1410 and the inner surface 1214 of the opening 1213 in the lid 1200 cooperate to enable sealing engagement between the fitment 1410 and the lid 1200.

The canister 1100, the lid 1200 and the fitment 1410 are in sealing engagement when the fluid collection system 1000 is in the closed position. As discussed above, the lid 1200 is sealingly engaged with the canister 1100. The fitment 1410 of the fitment assembly 1400 is sealingly engaged with the lid 1200. Together, the fitment assembly 1400 and the lid 1200 substantially close the opening 1131 in the canister 1100.

An interstitial chamber 1001 is formed when the fluid collection system 1000 is in the closed position, as shown in FIG. 3. The interstitial chamber 1001 is the space substantially enclosed by the canister 1100, the liner 1310, the lid 1200 and the fitment assembly 1400. To enable the interstitial chamber 1001 to maintain vacuum pressure, the canister 1100 may be in sealing engagement with the lid 1200, the lid 1200 may be in sealing engagement with the fitment 1410, and the fitment 1410 may be in sealing engagement with the liner 1310. Preferably, the liner 1310 may be sealingly engaged to the fitment 1410 during the manufacturing process. If the fluid chamber vacuum port 1440 uses a pass-through design, the filter 1560 may also be in sealing engagement with the fitment 1410 to substantially enclose the interstitial chamber 1001, and the filter 1560 may separate the interstitial chamber 1001 and the fluid chamber 1002.

When a vacuum is applied to the interstitial chamber 1001, the liner 1310 expands in the cavity 1130 of the canister 1100. The canister-facing surface 1312 of the liner 1310 may at least partially conform to the bottom wall 1110 and the side walls 1121, 1122, 1123, 1124 of the canister 1100. A vacuum source 1700, such as a vacuum pump, is used to provide a vacuum. The vacuum is communicated to the interstitial chamber 1001 by coupling the vacuum source 1700 to the vacuum source end 1172 of the interstitial vacuum port 1170.

The fitment 1410 includes a fluid port 1450 that allows fluid to enter the fluid chamber 1002. The fluid port 1450 is an opening that extends from the upper surface 1422 of the upper wall 1421 of the protrusion 1420 to the lower surface 1423 of the upper wall 1421 of the protrusion 1420. The patient end 1451 of the fluid port 1450 protrudes from the upper surface 1422 of the upper wall 1421 of the protrusion 1420, such that a patient tube may be connected to the patient end 1451 of the fluid port 1450. A fluid chamber end 1452 of the fluid port 1450 opens proximate the lower surface 1423 of the upper wall 1421. The fluid chamber end 1452 of the fluid port 1450 opens within the area enclosed by the rib 1470. The fluid chamber end 1452 of the fluid port 1450 may protrude from the lower surface 1423 of the upper wall 1421, or it may be simply an opening in the upper wall 1421. Fluid flows from the patient tube and through the fluid port 1450 on the fitment 1410 before entering the fluid chamber 1002.

In order to prevent contamination, it is desirable to prevent fluid from flowing upstream (from the fluid chamber 1002, out of the fluid port 1450 and into the patient tube, toward the patient) after the fluid has entered the fluid chamber 1002. Accordingly, a fluid port check valve (not shown) may optionally be coupled to the fluid port 1450 to allow one-directional flow of fluid through the fluid port 1450. A fluid port check valve permits fluid to flow downstream from the patient toward the fluid chamber 1002, but prevents fluid from flowing upstream from the fluid chamber 1002 toward the patient.

The fitment 1410 includes a fluid chamber vacuum port 1440 through which a vacuum is applied to the fluid chamber 1002. The fluid chamber vacuum port 1440 may preferably be a pass-through vacuum port which allows the vacuum applied to the interstitial chamber 1001 to pass through to the fluid chamber 1002. The fluid chamber vacuum port 1440 is an opening in the base 1411 of the fitment 1410 that allows gas to move between the fluid chamber 1002 and the interstitial chamber 1001. The fluid chamber vacuum port 1440 has a fluid chamber end 1441 located on, and protruding from, the lower surface 1413 of the fitment 1410, within the portion of the lower surface 1413 enclosed by the rib 1470. An interstitial chamber end 1442 of the fluid chamber vacuum port 1440 is located on a recessed portion 1416 of the upper surface 1412 of the base 1411. The recessed portion 1416 may extend from an end of the base 1411 toward the interstitial chamber end 1442 of the fluid chamber vacuum port 1440.

The vacuum source 1700 is connected to the interstitial chamber 1001, resulting in a reduced pressure in the interstitial chamber 1001. The reduced pressure in the interstitial chamber 1001 may cause air from the fluid chamber 1002 to pass through the fluid chamber vacuum port 1440 and into the interstitial chamber 1001, thereby creating a vacuum in the fluid chamber 1002. In this pass-through configuration, the fluid chamber 1002 is upstream of the interstitial chamber 1001. The pass-through configuration may be preferred over other configurations where the fluid chamber vacuum port 1440 is independently connected to the vacuum source 1700 because the user does not need to connect a vacuum tube to the fluid chamber 1002 during each procedure. However, either configuration of fluid chamber vacuum ports 1440 may be used.

Figure 23:
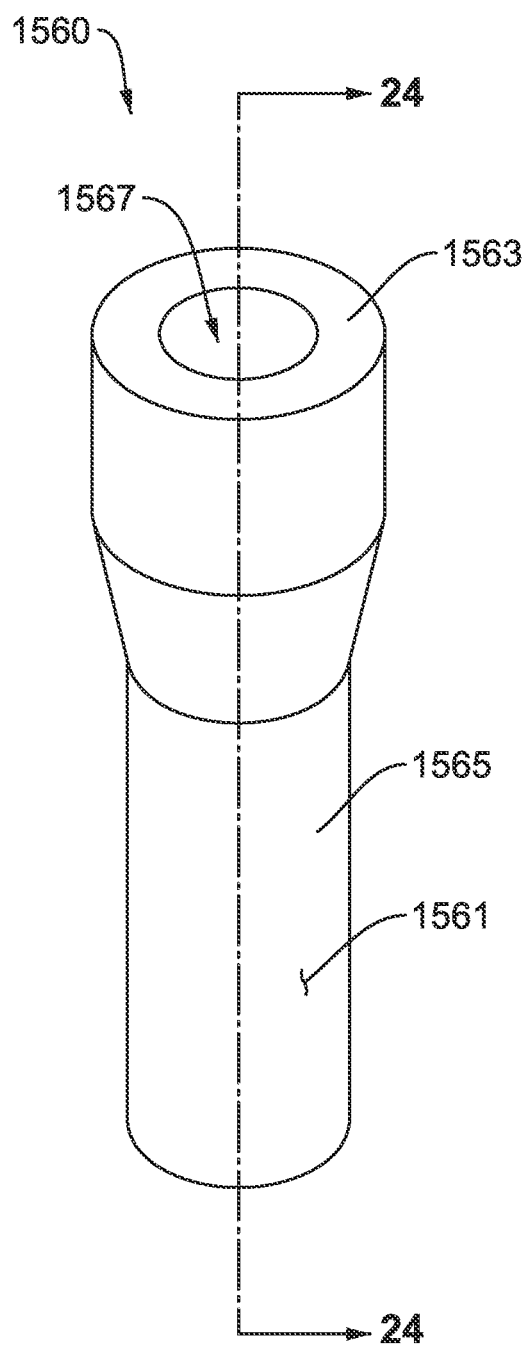
FIG. 23 is an isometric view of a filter of the fitment assembly of FIG. 17, shown from above.
Figure 24:
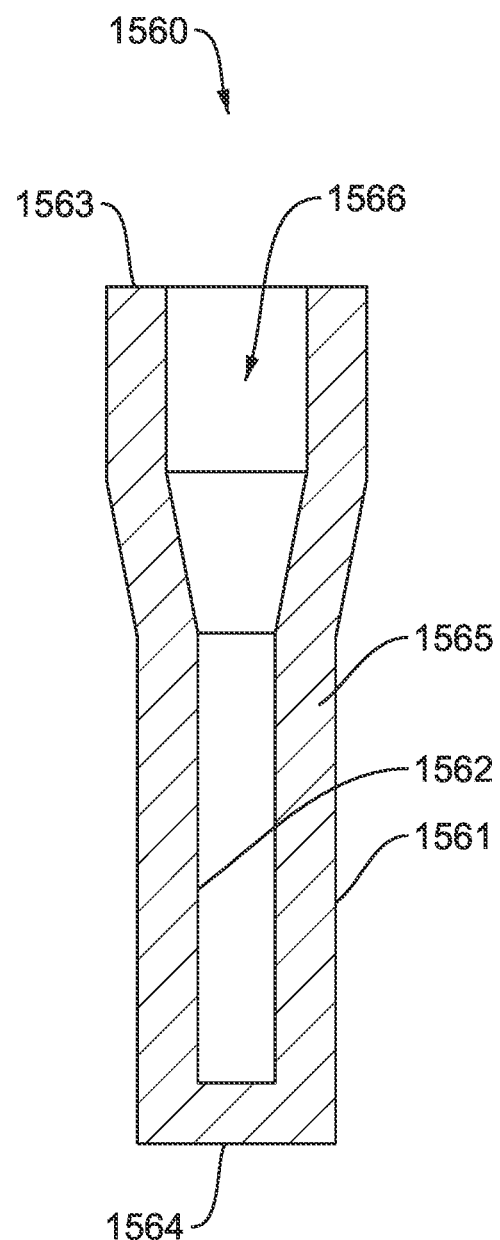
FIG. 24 is a cross-sectional view of the filter of FIG. 23 taken along line 24, shown from the side.

A filter 1560 shown in FIGS. 23-24 is coupled to the fluid chamber vacuum port 1440. Air passes through the filter 1560 when it is drawn from the fluid chamber 1002 toward the vacuum source 1700. The filter 1560 serves two purposes. First, the filter 1560 prevents damage to the vacuum source 1700 by removing bacteria, particulates and other solid matter from the air flowing toward the vacuum source 1700. Second, the filter 1560 acts as a vacuum shut-off, which stops the vacuum from being applied to the fluid chamber 1002 once the fluid chamber 1002 reaches its predetermined capacity.

The filter 1560 may be made from any number of materials. Preferably, the filter may be made from a porous hydrophobic material that has a dry state and a wet state. The filter material is in a dry state when it is not in contact with a liquid. The filter material is in a wet state when it is in contact with a liquid. When the filter material is in the dry state, the pores in the material are large enough that gas is able to pass through the filter material but small enough that solid materials (e.g., bacteria, particulates) cannot. In the wet state, when the filter material comes into contact with a liquid, the material swells and the pores shrink such that gas is no longer able to pass through the filter material.

The filter 1560 has a hollow cylindrical shape. The filter 1560 has a first end 1563, a second end 1564, and a side wall 1565 extending therebetween. The filter 1560 has a length extending from the first end 1563 to the second end 1564. A cylindrical central chamber 1566 extends from an opening 1567 in the first end 1563 toward the second end 1564. However, the central chamber 1566 does not have an opening on the second end 1564, and thus does not extend along the entire length of the filter 1560.

The filter 1560 is coupled to the fluid chamber vacuum port 1440 on the fitment 1410. More specifically, an interference fit between the side wall 1565 of the filter 1560 and the fluid chamber end 1441 of the fluid chamber vacuum port 1440 may create sealing engagement between the filter 1560 and the fitment 1410. The filter 1560 has an upstream surface 1561 that may be in communication with the fluid chamber 1002 and a downstream surface 1562 that may be in communication with the interstitial chamber 1001 and the vacuum source 1700 during use. The inner surface of the side wall 1565 forms the downstream surface 1562 of the filter 1560. During use, air moves through the filter 1560 in a downstream direction. Air passes from the fluid chamber 1002 into the filter 1560 at the upstream surface 1561, moves through the filter 1560, and leaves the filter 1560 on the downstream surface 1562 as it moves toward the vacuum source 1700.

Figure 26:
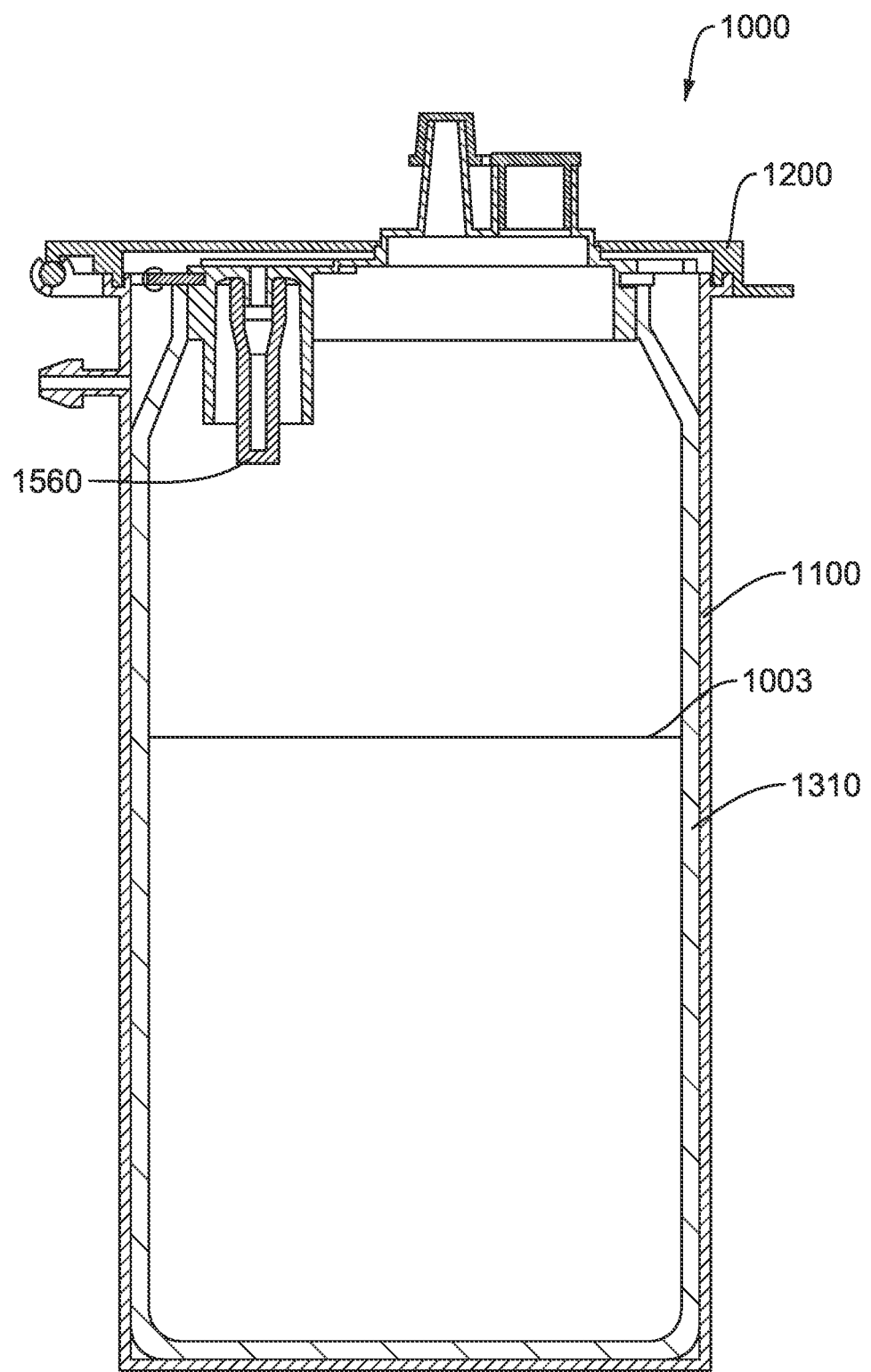
FIGS. 26-28 are cross-sectional views of the fluid collection system of FIG. 1 taken along line 3, shown from the side in a closed position when the fluid level is at varying positions in the fluid chamber.
Figure 27:
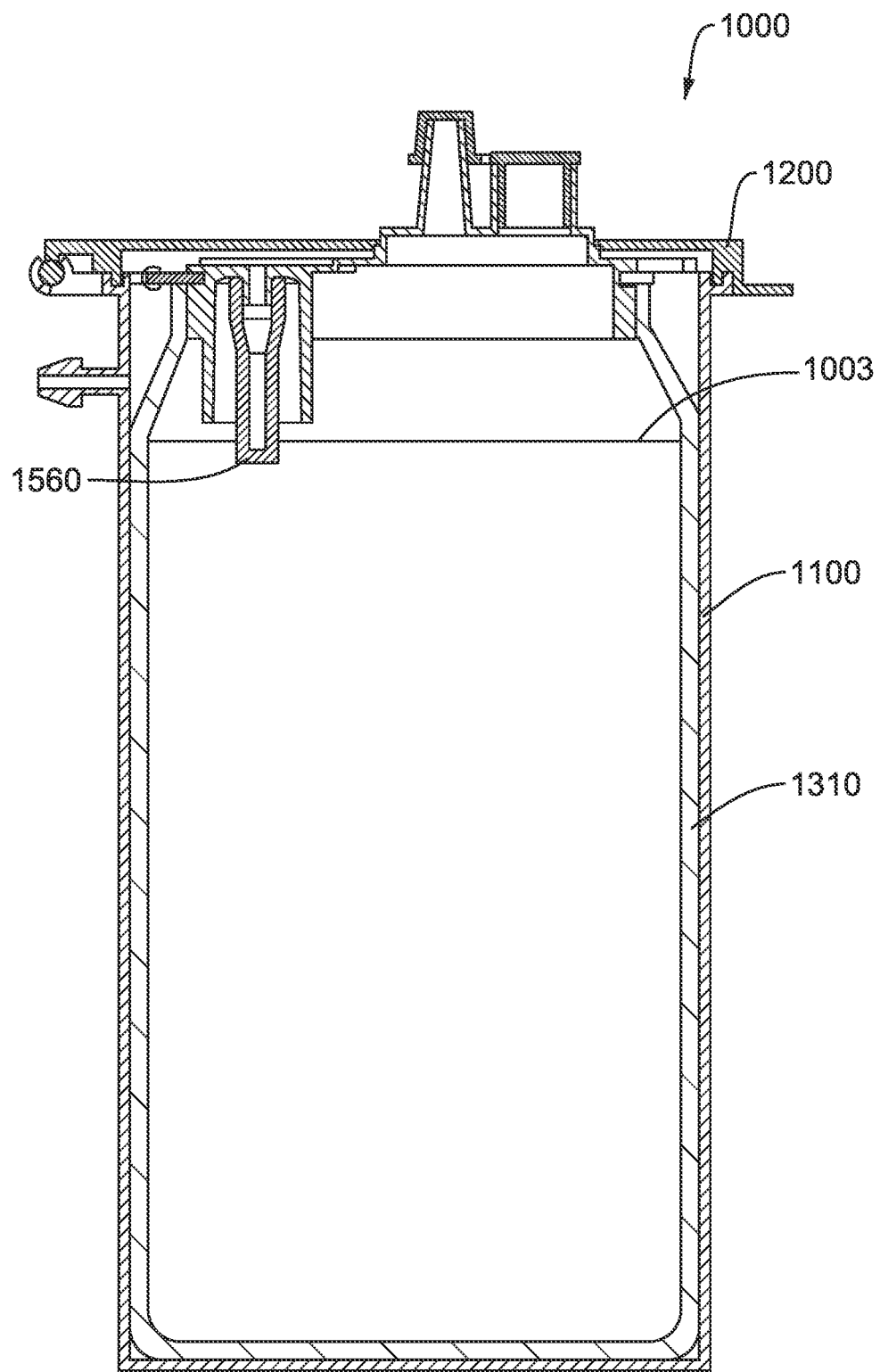
Figure 28:
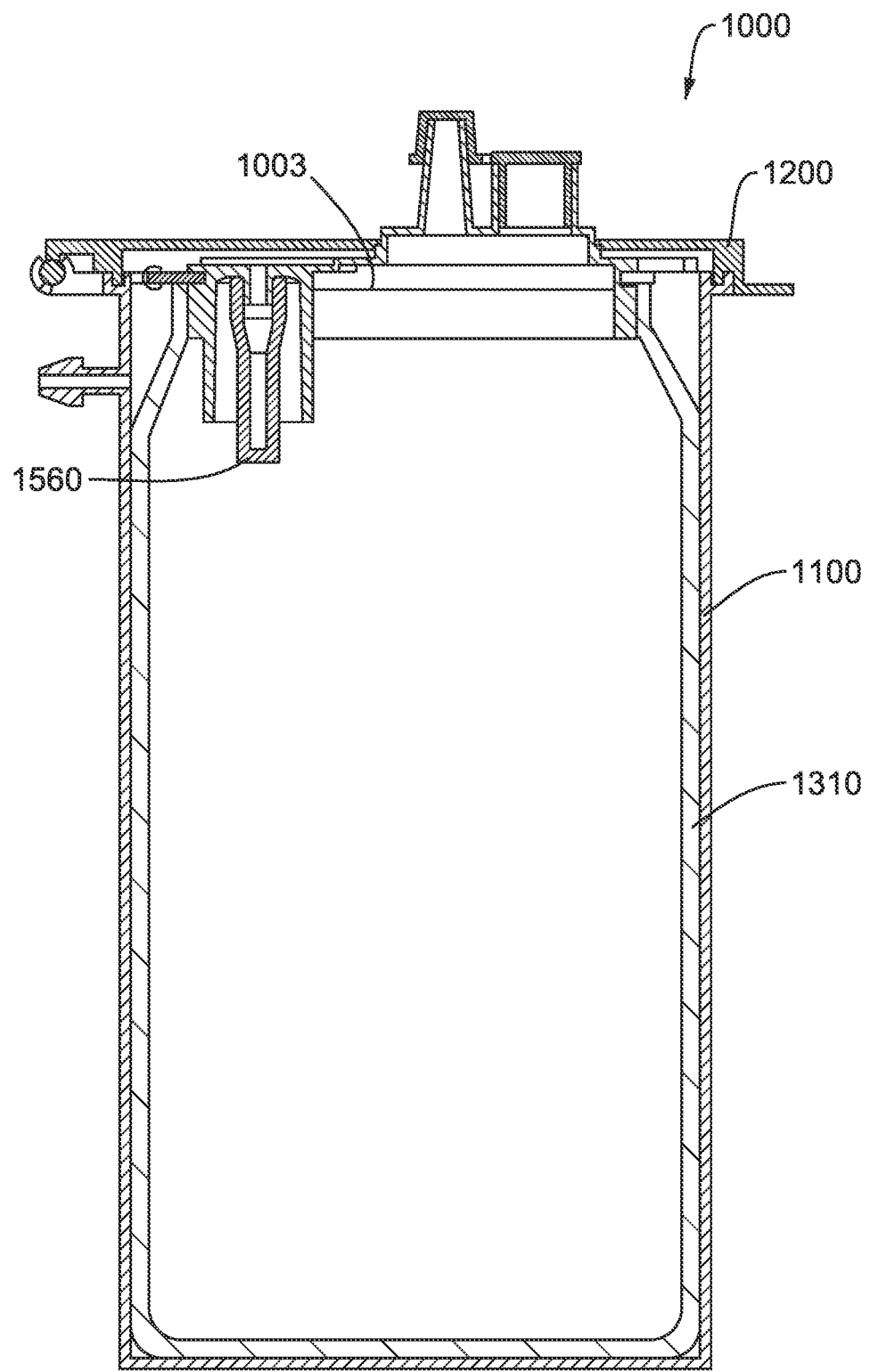

FIGS. 26-28 show various stages of operation of the filter 1560. The filter 1560 starts in a dry state. Air is pulled through the filter 1560 from the fluid chamber 1002 toward the vacuum source 1700, thereby creating a vacuum in the fluid chamber 1002. Fluid from the patient then flows through the fluid port 1450 and into the fluid chamber 1002, causing the fluid level 1003 in the fluid chamber 1002 to rise (FIG. 26). Eventually, the fluid level 1003 in the fluid chamber 1002 rises such the fluid contacts a portion of the upstream surface 1561 of the filter 1560 (FIG. 27). At this point, the pores on the upstream surface 1561 begin to close if they are in contact with the fluid. However, if a portion of the upstream surface 1561 of the filter 1560 is still dry, air may still flow through the filter 1560 at the dry areas on the upstream surface 1561. Vacuum is therefore still being provided to the fluid chamber 1002 through pores on the upstream surface 1561 that are not in contact with the fluid (i.e., areas of the upstream surface 1561 that are above the fluid level 1003). Finally, the fluid level 1003 rises to the uppermost point on the upstream surface 1561 of the filter 1560 such that fluid is contacting substantially all of the upstream surface 1561 of the filter 1560 (FIG. 28). Once the upstream surface 1561 of the filter 1560 is saturated with liquid, the pores on the filter 1560 close. Therefore, air cannot flow through the filter 1560 and the vacuum is no longer applied to the fluid chamber 1002, which prevents additional fluid from collecting in the fluid chamber 1002.

In order to stop the flow of air through the filter 1560, the upstream surface 1561 of the filter 1560 should be saturated with liquid. However, it is undesirable for the fluid to penetrate through the filter 1560 from the upstream surface 1561 to the downstream surface 1562. The presence of fluid on the downstream surface 1562 of the filter 1560 may indicate a failure of the filter 1560. Ideally, the upstream surface 1561 of the filter 1560 will become substantially saturated with liquid while the downstream surface 1562 of the filter 1560 remains substantially dry.

The height of the filter 1560 relative to the bottom wall 1110 of the canister 1100 determines how much fluid can collect in the fluid chamber 1002 before the vacuum is no longer applied to the fluid chamber 1002. Placing the filter 1560 farther from the bottom wall 1110 of the canister 1100 allows more fluid to collect in the fluid chamber 1002 before the vacuum to the fluid chamber 1002 is shut off. In a preferred embodiment, the filter 1560 is vertically positioned above the bottom wall 1110 of the canister 1100 and below the fluid port 1450 when the liner assembly 1300 is inserted into the canister 1100. The fluid level 1003 will rise such that the upstream surface 1561 of the filter 1560 becomes saturated before the fluid level 1003 reaches the fluid port 1450, which will stop vacuum from being applied to the fluid chamber 1002 before the fluid level 1003 reaches the patient end 1451 of the fluid port 1450. Therefore, a fluid port check valve is not needed if the filter 1560 is positioned below the fluid port 1450 because the fluid level 1003 in the fluid chamber 1002 will not typically rise high enough to allow a reverse fluid flow from the fluid chamber 1002 to the patient. This positioning of the filter 1560 relative to the fluid port 1450 is shown in FIG. 3. Once the fluid level 1003 reaches the upper most point of the upstream surface 1561 of the filter 1560, the vacuum source 1700 cannot apply a vacuum into the fluid chamber 1002 so no more fluid will be collected in the fluid chamber 1002. However, the fluid level 1003 is still below the patient end 1451 of the fluid port 1450, and therefore fluid will not flow out of the fluid port 1450 and back to the patient.

The fitment 1410 may also include a filter guard 1480 that is designed to prevent fluid in the fluid chamber 1002 from splashing onto the filter 1560. Without a filter guard 1480, fluid may splash onto the filter 1560 as it enters the fluid chamber 1002. Accidental fluid splashes are undesirable because the filter 1560 will become wet and the vacuum in the fluid chamber 1002 may be significantly decreased or shut off entirely, even though the fluid level 1003 in the fluid chamber 1002 is well below the capacity. Therefore, a filter guard 1480 is built into the fitment 1410 to partially surround the filter 1560 and protect the filter 1560 from accidental fluid splashes. The filter guard 1480 may be a cylindrical sheath 1481 protruding from the portion of the lower surface 1413 of the fitment 1410 that lies within the rib 1470. The cylindrical sheath 1481 may have two slots 1482 to improve air flow to the filter 1560.

The fitment 1410 may also include a pour spout 1460 that would allow the user to empty the fluid from the fluid chamber 1002 after the surgical procedure has been completed. The pour spout 1460 extends between an external end 1461 that opens to the surrounding environment on the upper surface 1422 of the upper wall 1421 and a fluid chamber end 1462 that opens to the fluid chamber 1002 on the lower surface 1423 of the upper wall 1421. The pour spout 1460 may have a larger diameter than a fluid port 1450 in order to facilitate an increased flow rate. The pour spout 1460 may also be used as an accessory port during the procedure, allowing a specimen sock or a solidifier to be inserted into the fluid chamber 1002.

Caps are provided to close the fluid port 1450 and the pour spout 1460. Any unused fluid ports and/or pour spouts are capped during the procedure to ensure that adequate vacuum levels are supplied to the patient. Without a cap, air would flow into the fluid chamber 1002 through the open fluid port 1450 or the open pour spout 1460 and reduce the vacuum being provided to the patient. The fluid port 1450 and pour spout 1460 are also capped when removing the liner assembly 1300 from the canister 1100. A cap on the pour spout 1460 may be removed when emptying fluid from the fluid chamber 1002.

Therefore, a cap assembly 1550 may also be provided with the fitment assembly 1400 of the first embodiment. The cap assembly 1550 is shown as part of the fitment assembly 1400 in FIGS. 17-18. A fluid port cap 1551 is configured to close the fluid port 1450, and a pour spout cap 1552 is configured to close the pour spout 1460. The caps are connected via a bridge 1553. The liner assembly 1300 may be provided such that the cap assembly 1550 is connected to the fitment 1410, either by inserting the fluid port cap 1551 into the fluid port 1450 and the pour spout cap 1552 into the pour spout 1460, or by connecting the bridge 1553 to the fitment 1410.

Figure 9:
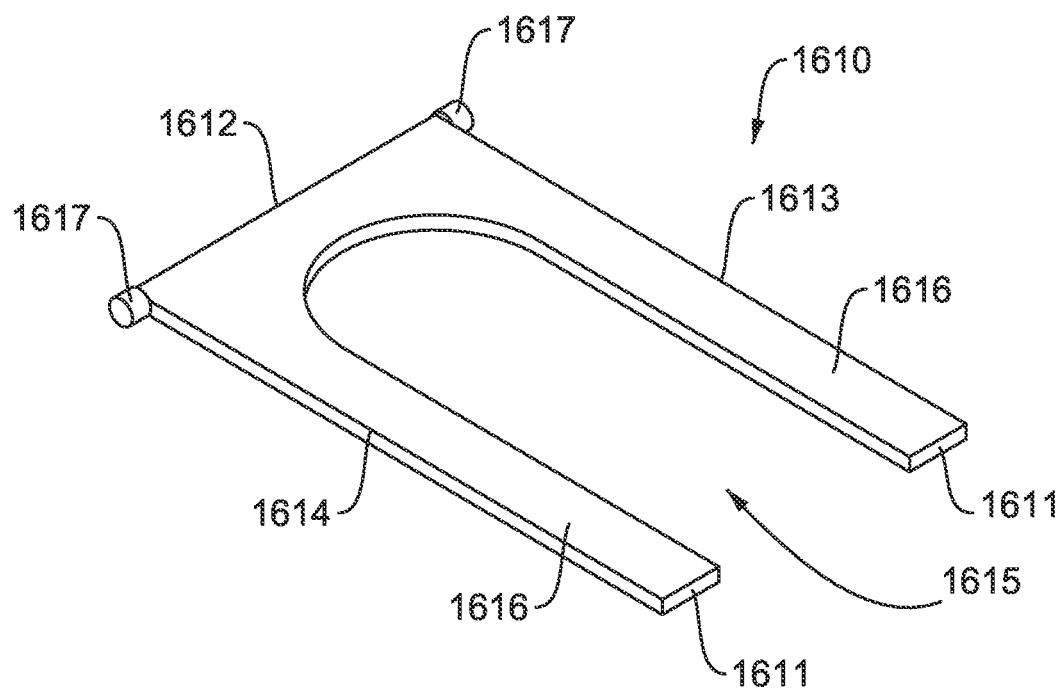
FIG. 9 is an isometric view of a bracket of the fluid collection system of FIG. 1, shown from above.
Figure 10:
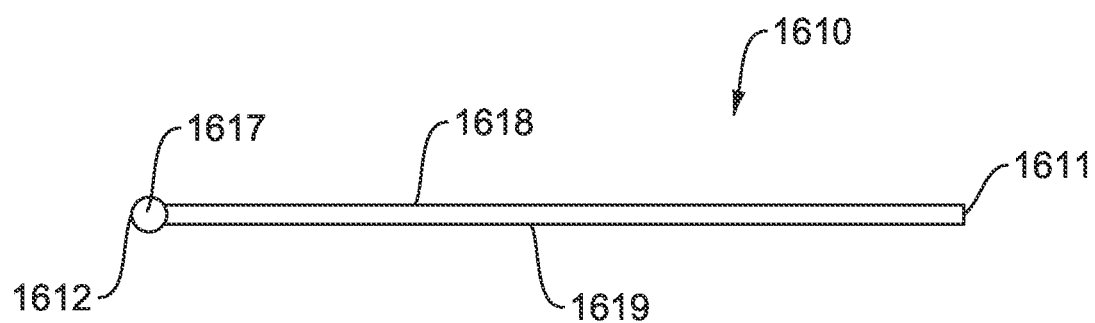
FIG. 10 is a side view of the bracket of FIG. 9.

The fluid collection system 1000 optionally includes a fitment support 1600, which holds the fitment 1410 in place. A bracket 1610, shown in FIGS. 9-10, is one example of a fitment support 1600. The bracket 1610 has an upper surface 1618 and a lower surface 1619, and may be substantially planar. The bracket 1610 has a first end 1611 and a second end 1612 opposite the first end 1611. The bracket 1610 may also have third and fourth ends 1613, 1614, both adjacent to each of the first and second ends 1611, 1612. A slot 1615 extends from the first end 1611 of the bracket 1610 toward the second end 1612, forming two prongs 1616, one on either side of the slot 1615.

When the fluid collection system 1000 is in the closed position as shown in FIGS. 1 and 3, the upper surface 1618 of the bracket 1610 faces the lid 1200 and the lower surface 1619 of the bracket 1610 faces the bottom wall 1110 of the canister 1100. The third side wall 1123 and the fourth side wall 1124 of the canister 1100 may each include a ledge 1161 adjacent to the interior surface 1128 of the side wall, proximate the top end 1127. Each ledge 1161 may extend along the full length of the side wall, or the ledge 1161 may extend along only a portion of the length of the side wall. Furthermore, the ledges 1161 could also extend along at least a portion of the top end 1127 of the first side wall 1121 and/or second side wall 1122. The bracket 1610 may rest on the ledges 1161 while the fluid collection system 1000 is in the closed position. The bracket 1610 is positioned relative to the canister 1100 such that the bracket 1610 is surrounded by the groove 1140 on the canister 1100. Therefore, when the fluid collection system 1000 is in the closed position, the bracket 1610 is located entirely within the interstitial chamber 1001.

The bracket 1610 is moveably coupled to the canister 1100 by a second hinge. The bracket 1610 may have a second hinge element 1617 and the canister 1100 may have a second hinge element 1152. When assembled, the second hinge element 1617 on the bracket 1610 and the second hinge element 1152 on the canister 1100 cooperate to form the second hinge. The second hinge element 1152 on the canister 1100 may be positioned to allow the bracket 1610 to rotate around an axis that is substantially parallel to the top end 1127 of the side wall that includes the first hinge element 1151. As shown in FIG. 3, the second hinge element 1125 allows the bracket 1610 to rotate around an axis that is substantially parallel to the top end 1127 of the second side wall 1122. The second hinge element 1152 may include grooves located on the top end 1127 of each of the third side wall 1123 and the fourth side wall 1124, proximate the second side wall 1122. The second hinge element 1617 on the bracket 1610 may be proximate the second end 1612 of the bracket 1610.

In order to facilitate the insertion of the fitment assembly 1400 into the bracket 1610, it may be preferable that the end of the bracket 1610 that contains the second hinge element 1617 is longer than the adjacent ends. Therefore, based on the above description of the bracket 1610, it may be preferable that the second end 1612 of the bracket 1610 is longer than the third and fourth ends 1613, 1614 of the bracket 1610. The side walls of the canister 1100 and the lid 1200 may be adjusted accordingly. Because the bracket 1610, as described above, rotates about an axis substantially parallel to the second side wall 1122 of the canister 1100, it may be preferable that the second side wall 1122 is longer than the third and fourth side walls 1123, 1124 of the canister 1100. Likewise, it may be preferable that the second side wall 1222 of the lid 1200 is longer than the third and fourth side walls 1223, 1224 of the lid 1200.

The bracket 1610 is moveable between an open position shown in FIG. 25 and a closed position shown in FIG. 3. In the closed position, the first end 1611 of the bracket 1610 is positioned near the top end 1127 of the first side wall 1121 of the canister 1100, and the lower surface 1619 of the bracket 1610 rests on the ledges 1161 of the canister 1100. In the open position, the first end 1611 of the bracket 1610 is moved away from the top end 1127 of the first side wall 1121 of the canister 1100, and the lower surface 1619 of the bracket 1610 does not rest on the ledges 1161 of the canister 1100.

The bracket 1610 and the lid 1200 may also be moveably coupled, such that moving the lid 1200 to the open position also causes the bracket 1610 to move to the open position and moving the lid 1200 to the closed position also causes the bracket 1610 to move to the closed position. The connection between the bracket 1610 and the lid 1200 may be a pin and slot connection, for example. The pin and slot connection allows the bracket 1610 and the lid 1200 to be opened and closed simultaneously at different yet related rates. Preferably, the first side wall 1221 of the lid 1200 will travel farther than the first end 1611 of the bracket 1610 to allow the user access to the bracket 1610 such that the fitment 1410 of the liner assembly 1300 may be inserted into the slot 1615 of the bracket 1610. For example, the first side wall 1221 of the lid 1200 may travel twice as far as the first end 1611 of the bracket 1610.

When the fluid collection system 1000 is in the closed position, the fitment 1410 is resting in the slot 1615 in the bracket 1610 such that the lower surface 1413 of the base 1411 of the fitment 1410 rests on the upper surface 1618 of the bracket 1610, and the liner 1310 is placed in the cavity 1130 of the canister 1100.

Figure 29:
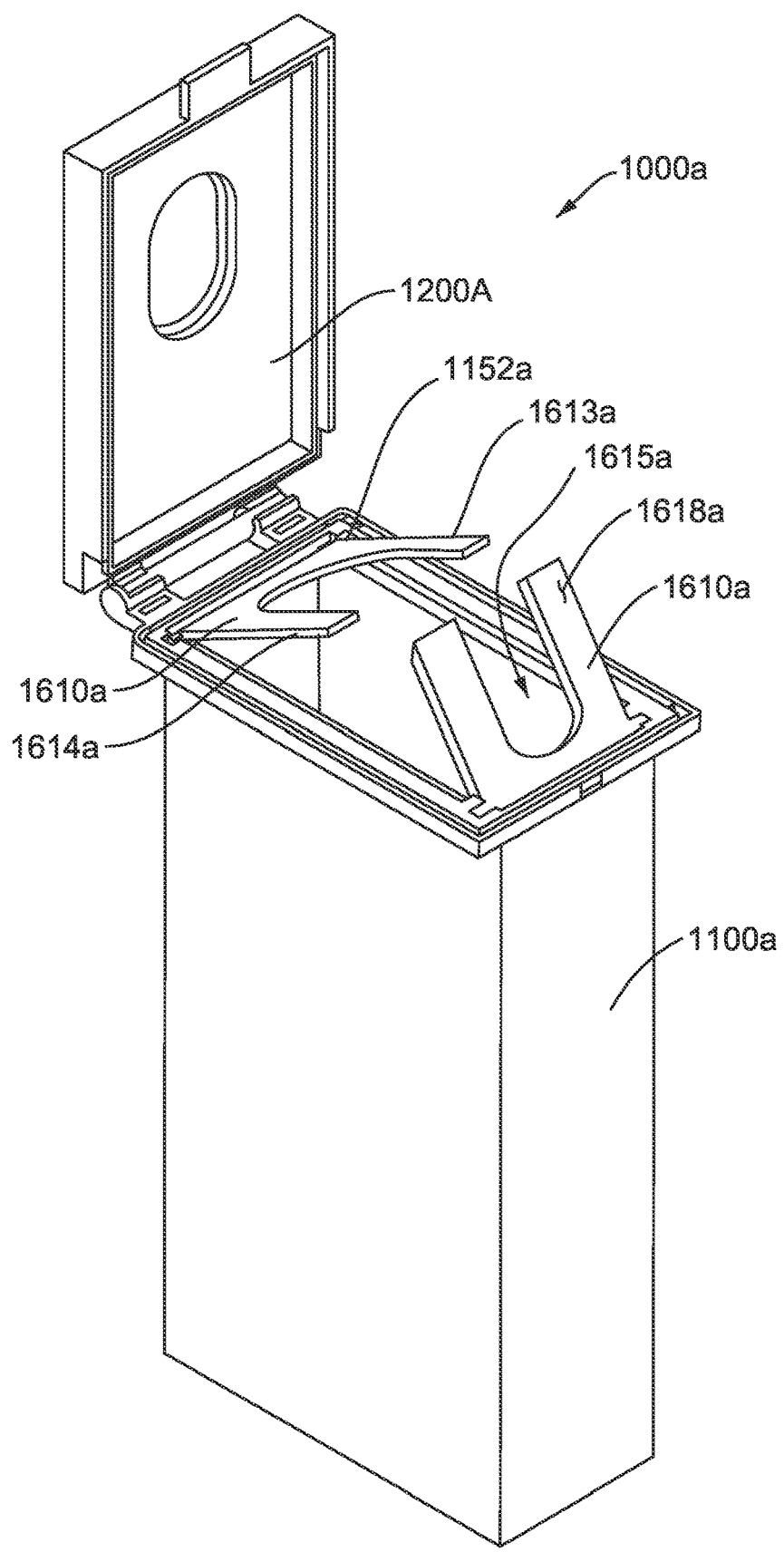
FIG. 29 is an isometric view of a variation of the fluid collection system of FIG. 1 including two brackets, shown from above in the open position.

Any number of brackets may be used. For example, FIG. 29 shows an open position of a fluid collection system 1000*a* having a canister 1100*a*, a lid 1200*a*, and two brackets 1610*a*. The fluid collection system 1000*a* may be similar to fluid collection system 1000, and reference will now be made to figures wherein like structures are provided with like reference designations. The liner assembly, not shown in FIG. 29, of fluid collection system 1000*a* could be similar to the liner assembly 1300 of fluid collection system 1000, shown in FIG. 11. The lid 1200*a* of fluid collection system 1000*a* may be the same as the lid 1200 of fluid collection system 1000. The canister 1100*a* may be similar to the canister 1100 of fluid collection system 1000; however, the canister 1100*a* may have two second hinge elements 1152*a* instead of one. The second hinge elements 1152*a* may be positioned such that the brackets 1610*a* rotate about axes parallel to opposing side walls of the canister 1100*a*. The brackets 1610*a* of fluid collection system 1000*a* may be similar to the bracket 1610 of fluid collection system 1000; however, the third and fourth ends 1613*a*, 1614*a* of the brackets 1610*a* may be shorter in length compared to the third and fourth ends 1613, 1614 of bracket 1610. It may be preferable that the first ends 1611*a* of the brackets 1610*a* do not overlap in the closed position.

The brackets 1610*a* are moveable between an open position shown in FIG. 29 and a closed position. When the brackets 1610*a* are in a closed position, the slots 1615*a* in the brackets 1610*a* are aligned to form a hole shaped and sized to receive the fitment. The lower surface of the base of the fitment rests on the upper surface 1618*a* of each bracket 1610*a*.

Figure 21:
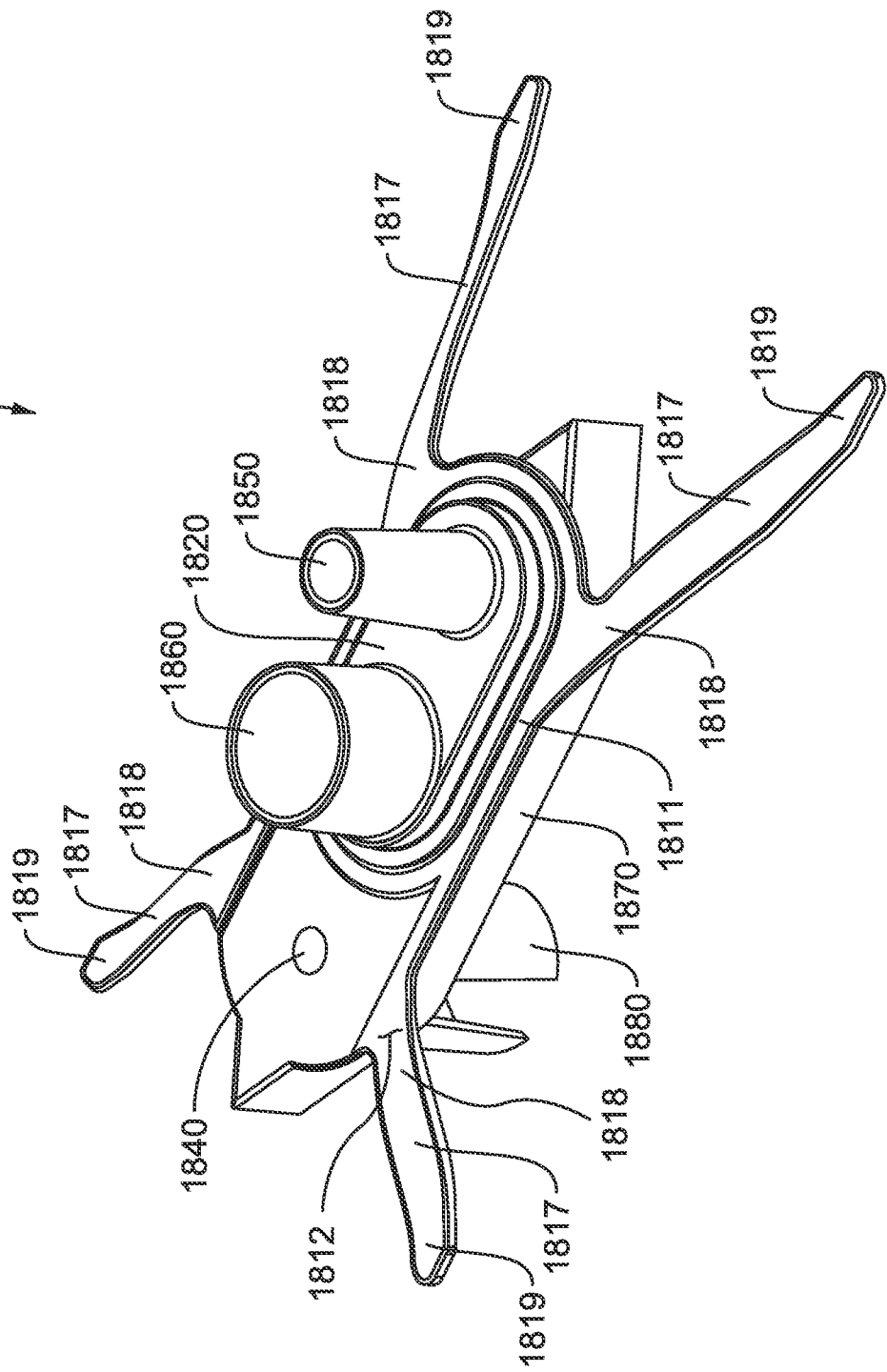
FIG. 21 is an isometric view of a variation of the fitment of FIG. 19 including supports incorporated into the fitment, shown from above.
Figure 22:
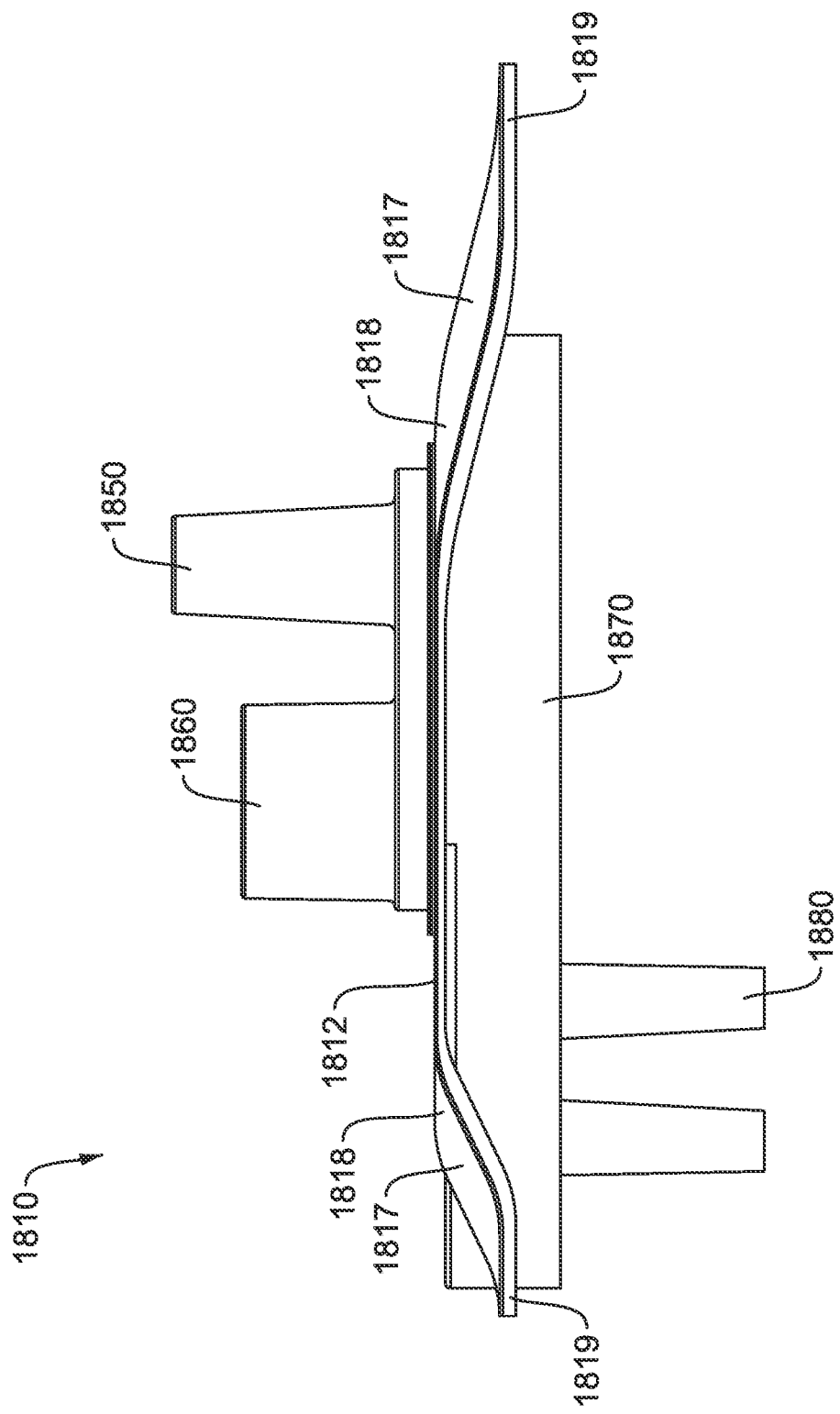
FIG. 22 is a side view of the fitment of FIG. 21.

Alternatively, the fitment support 1600 (for example, the bracket 1610) may be eliminated, and the fitment itself may instead be modified. Fitment 1810 is similar to fitment 1410, and includes many of the same features as fitment 1410. Reference will now be made to figures wherein like structures are provided with like reference designations. Fitment 1810 includes supports 1817, as shown in FIGS. 21-22. The supports 1817 may be legs extending from any surface of the fitment 1810. In preferred embodiments, the supports 1817 may extend from the base 1811 of the fitment 1810. Each support 1817 may have a proximal end 1818 connected to the base 1811 of the fitment 1810, and a distal end 1819 opposite the proximal end 1818.

The supports 1817 may have a variety of shapes. The supports 1817 may be substantially planar and parallel to the upper surface 1812 of the base 1811. Alternatively, the supports 1817 may be curved, angled, or otherwise nonplanar. In particular, the supports 1817 may curve or angle downward, such that the distal end 1819 of each support 1817 is farther from the upper surface 1812 of the base 1811 of the fitment 1810 compared to the proximal end 1818 of each support 1817.

When the fluid collection system 1000 is in the closed position, the supports 1817 of the fitment 1810 may rest on top edge 1127 of one or more of the side walls 1121, 1122, 1123, 1124 of the canister 1100. If ledges 1161 are included on the canister 1100, the supports 1817 of the fitment 1810 may rest on the ledges 1161. Furthermore, if nonplanar supports 1817 are used, closing the lid 1200 may cause the supports 1817 to deflect and flatten out, and thereby generate a force that pushes up on the fitment 1810, further ensuring a proper seal between the fitment 1810 and the lid 1200. Therefore, non-planar supports may be preferred.

The open position of the fluid collection system 1000 is shown in FIG. 25. The lid 1200 and the optional fitment support 1600 are in their respective open positions, and the lid 1200 is not sealingly engaged with the canister 1100. In FIG. 25, the liner assembly 1300 has not yet been inserted into the canister 1100. When the liner assembly 1300 is inserted into the canister 1100, the liner 1310 is positioned within the cavity 1130 of the canister 1100 and the fitment 1410 is resting on the fitment support 1600 or on the canister 1100.

The closed position of the fluid collection system 1000 is shown in FIGS. 1 and 3. The lid 1200 and the optional fitment support 1600 are in their respective closed positions. The liner assembly 1300 is inserted into the canister 1100, such that the liner 1310 is positioned within the cavity 1130 of the canister 1100 and the fitment 1410 is resting on the upper surface 1618 of the fitment support 1600, or on the top edge 1127 of one or more of the side walls 1121, 1122, 1123, 1124 of the canister 1100 if no fitment support 1600 is needed. The canister 1100 and the lid 1200 may be in sealing engagement with one another. The lid 1200 and the fitment 1410 may be in sealing engagement with one another. The fitment 1410 and the liner 1310 may be in sealing engagement with one another. The fitment 1410 and the filter 1560 may be in sealing engagement with one another. Thus, the interstitial chamber 1001 may be sealed such that vacuum applied via the interstitial vacuum port 1170 is substantially maintained.

When using the fluid collection system 1000, the lid 1200 and the optional fitment support 1600 begin in their respective open positions as shown in FIGS. 25 and 29. The user then inserts the liner assembly 1300 into the canister 1100. If one bracket 1610 is being used as a fitment support 1600, the fitment 1410 is inserted into slot 1615 in the bracket 1610 so that the lower surface 1413 of the fitment 1410 rests on the upper surface 1618 of the bracket 1610. The fitment 1410 is positioned in the slot 1615 of the bracket 1610 such that the handle 1490 is positioned proximate to the first end 1611 of the bracket 1610. At the same time, the liner 1310 is positioned within the cavity 1130 of the canister 1100. If multiple brackets 1610 are being used as a fitment support 1600, the liner 1310 is positioned within the cavity 1130 of the canister 1100, and the fitment 1410 is centered over the slots 1615 in each bracket 1610 so that a portion of the lower surface 1413 of the fitment 1410 rests on the upper surface 1618 of each bracket 1610 when the brackets 1610 are moved to a closed position. If the fitment support 1600 is eliminated and supports 1817 are included on the fitment 1810 itself, then the fitment 1810 is positioned relative to the canister 1100 such that the supports 1817 on the fitment 1810 rest on the top edge 1127 of one or more of the side walls 1121, 1122, 1123, 1124 of the canister 1100.

Next, the fluid collection system 1000 is moved to the closed position as shown in FIGS. 1 and 3. The lid 1200 and the fitment support 1600 are moved to their respective closed positions, and the interstitial chamber 1001 is formed. A patient tube is connected to the patient end 1451 of the fluid port 1450 on the fitment 1410. Any unused ports are capped.

Vacuum is applied to the interstitial chamber 1001. A first method for applying the vacuum to the interstitial chamber 1001 is by physically connecting the vacuum source 1700 to the interstitial vacuum port 1170 (e.g., connecting a tube or other conduit). A second method for applying the vacuum to the interstitial chamber 1001 is by adjusting a regulator or on/off valve associated with the vacuum source 1700, such that the tube or other conduit between the vacuum source 1700 and the interstitial vacuum port 1170 may remain connected between procedures. Air is drawn out of the interstitial chamber 1001 through the interstitial vacuum port 1170 and toward the vacuum source 1700. The vacuum in the interstitial chamber 1001 may cause the liner 1310 to expand and at least partially conform to the interior surface 1112 of the bottom wall 1110 and the interior surface 1128 of the side walls 1121, 1122, 1123, 1124 of the canister 1100. The vacuum in the interstitial chamber 1001 may also draw air out of the fluid chamber 1002 through the fluid chamber vacuum port 1440. Therefore, a vacuum may be applied to both the interstitial chamber 1001 and the fluid chamber 1002.

The reduced pressure in the fluid chamber 1002 creates a vacuum in the fluid chamber 1002. Fluid from the patient flows along the patient tube, through the fluid port 1450, and into the fluid chamber 1002 where the fluid is collected. If the fluid chamber 1002 reaches its capacity (the fluid level 1003 in the fluid chamber 1002 rises high enough to saturate the upstream surface 1561 of the filter 1560), the vacuum to the fluid chamber 1002 is shut off, even though vacuum may still be applied to the interstitial chamber 1001 by the interstitial vacuum port 1170.

When the user is ready to remove the liner assembly 1300 from the canister 1100 (for example, at the end of a procedure or when the fluid chamber 1002 reaches its capacity), the vacuum source 1700 is physically disconnected from the interstitial vacuum port 1170, or the vacuum source 1700 is turned off using the regulator or on/off switch. The vacuum is no longer applied to the interstitial chamber 1001, and therefore the vacuum is also no longer applied through the fluid chamber vacuum port 1440 to the fluid chamber 1002. The lid 1200 and fitment support 1600 are moved to their respective open positions. If a bracket 1610 is used as the fitment support 1600, the liner assembly 1300 is removed from the canister 1100 by sliding the fitment 1410 out of the slot 1615 in the bracket 1610, and removing the liner 1310 from the cavity 1130 of the canister 1100. If multiple brackets 1610 are used as the fitment support 1600, the liner assembly 1300 is removed from the canister 1100 by lifting the fitment 1410, opening the brackets 1610, and removing the liner 1310 from the cavity 1130 of the canister 1100. If supports 1817 are included in the fitment 1810, the liner assembly is simply removed from the canister 1100 by lifting the fitment 1810. The user may use the handle 1490 on the fitment 1410 to assist with removal of the liner assembly 1300.

The fluid may then then be removed from the fluid chamber 1002. The pour spout cap 1552 is removed from the pour spout 1460 before fluid is poured out of the fluid chamber 1002 through the pour spout 1460. The liner assembly 1300 may then be disposed using standard medical waste disposal techniques.

The filter 1560 of the first embodiment is described as having a hollow cylindrical shape. However, the filter could also be substantially planar as described in the second and third embodiment.

The fitment 1410 of the first embodiment as described above has a handle 1490 that is attached to the base 1411 of the fitment 1410 near the end which includes the fluid port 1450 and the pour spout 1460. However, the handle could alternatively be attached anywhere else on the fitment 1410.

The canister 1100 is described as having two ledges 1161, one on the third side wall 1123 of the canister 1100 and one on the fourth side wall 1124 of the canister 1100. However, a ledge could also be provided on the top end 1127 of the second side wall 1122, adjacent to the interior surface 1128. The ledge on the second side wall 1122 could be provided in addition to, or in replacement of, the ledges 1161 on the third side wall 1123 and fourth side wall 1124.

There are also several ways to empty the fluid in the fluid chamber 1002, in addition to simply pouring the fluid out of the pour spout 1460 as described above. The user could also leave the pour spout cap 1552 in the pour spout 1460 and create a hole in the liner (e.g., by cutting, tearing, or any other method). The fluid may be poured out through this hole. If the user does not prefer to pour the fluid out of the fluid chamber 1002, an alternative method includes inserting a tube into the fluid chamber 1002 through the pour spout 1460, and connecting the tube to a pump that suctions the fluid out of the fluid chamber 1002.

Figure 30:
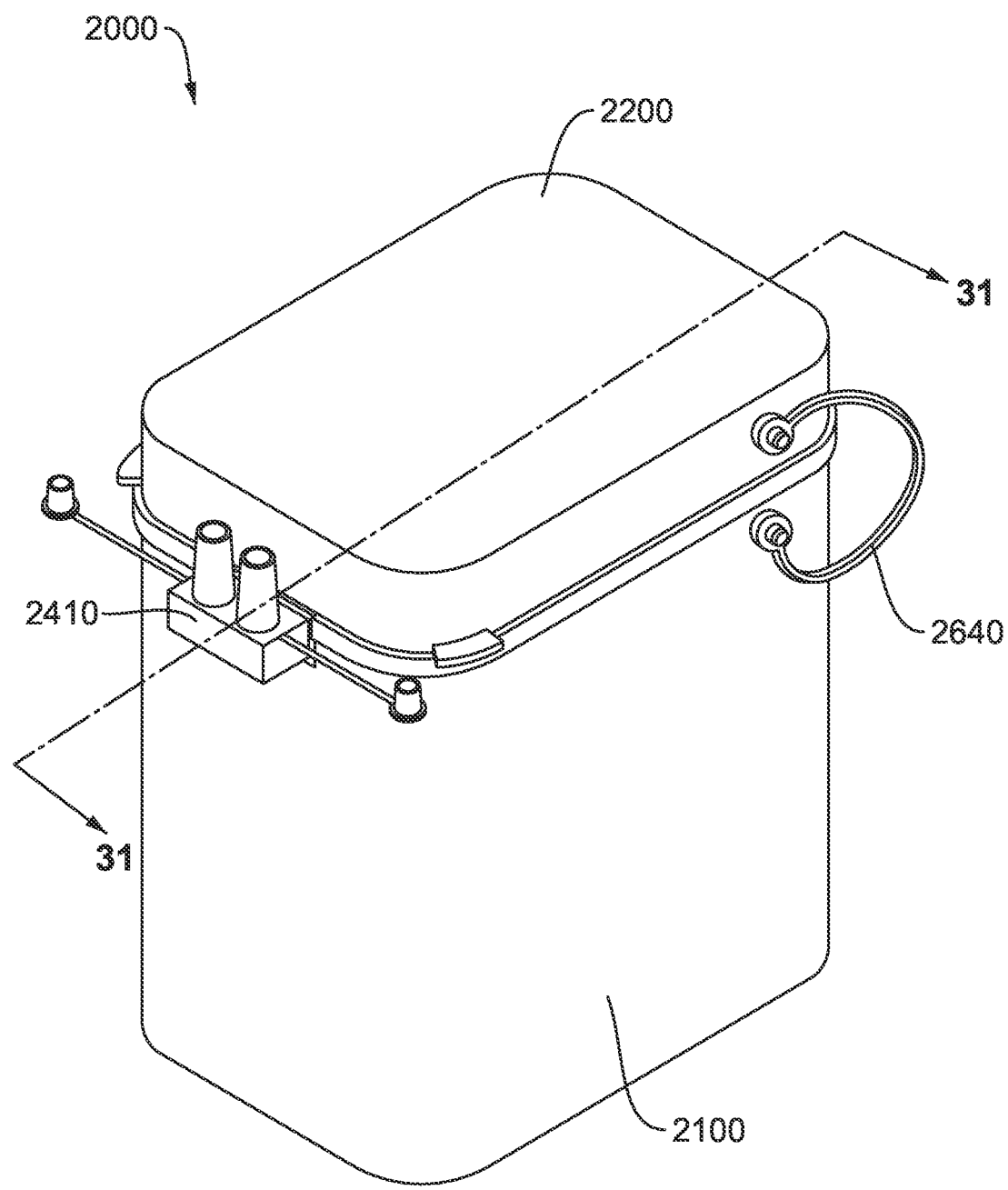
FIG. 30 is an isometric view of a second embodiment of the fluid collection system, shown from above in a closed position, according to certain aspects of the present application.
Figure 31:
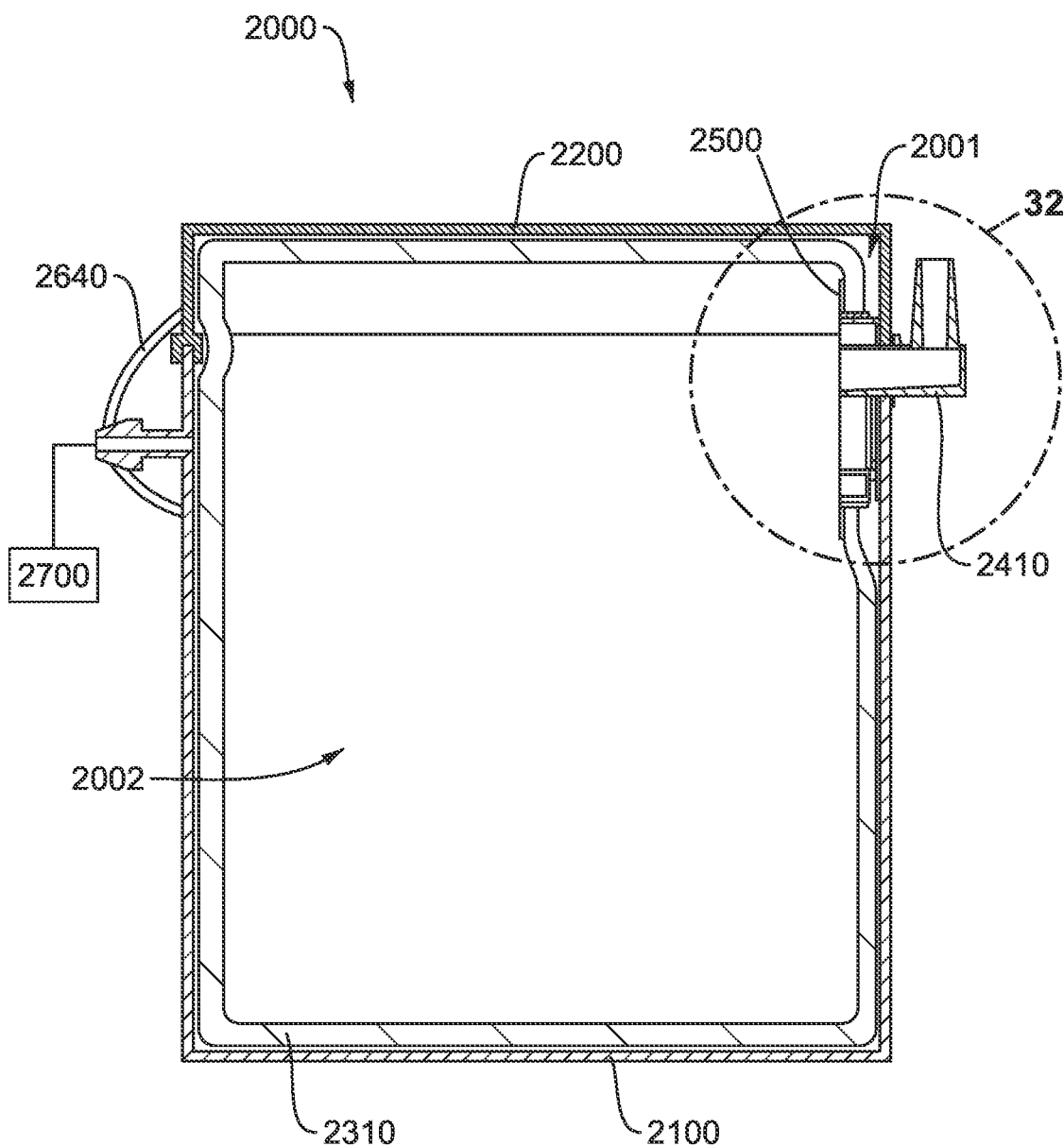
FIG. 31 is a cross-sectional view of the fluid collection system of FIG. 30 taken along line 31, shown from the side in a closed position.
Figure 32:
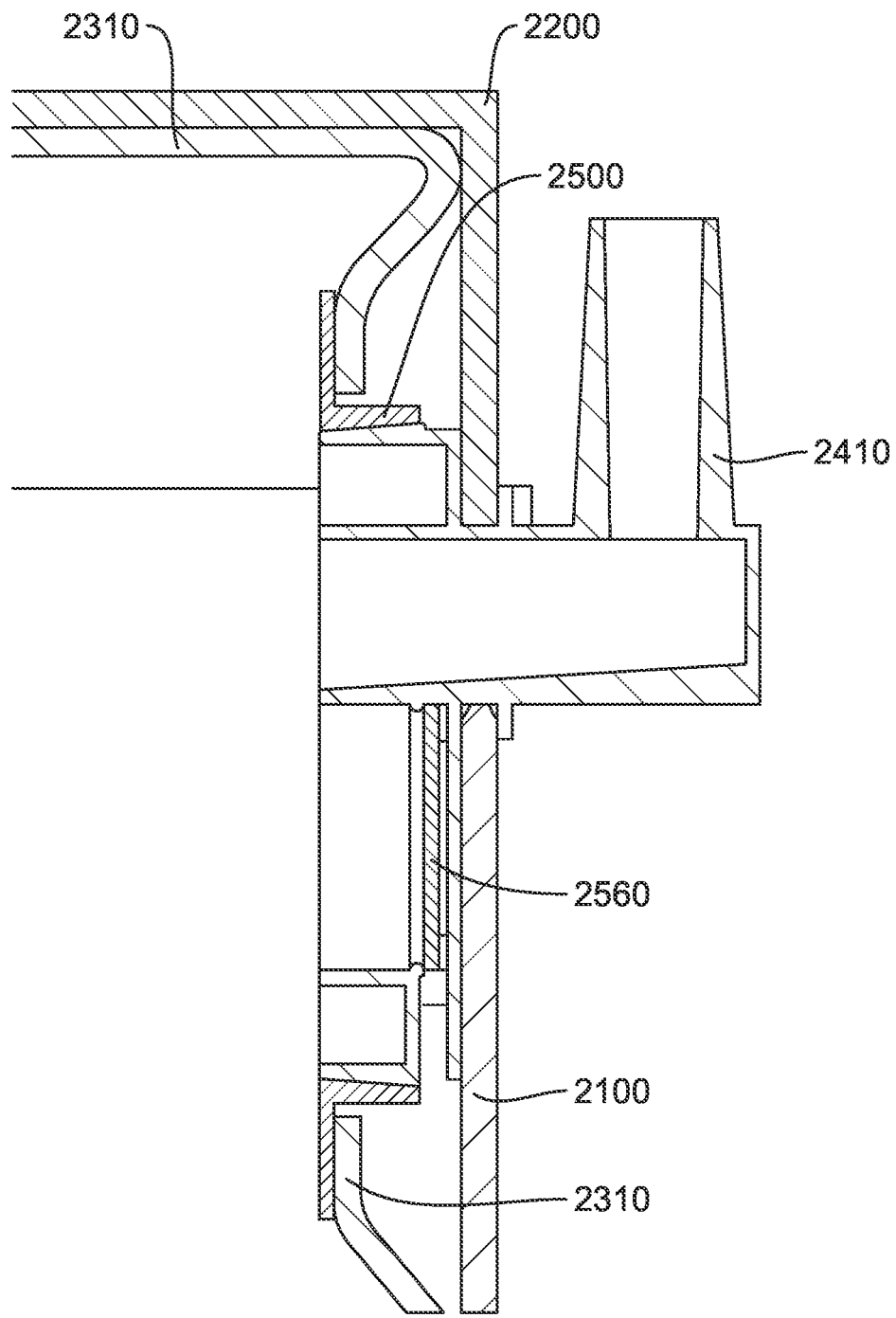
FIG. 32 is a detailed cross-sectional view of the fluid collection system of FIG. 31, shown from the side in a closed position
Figure 38:
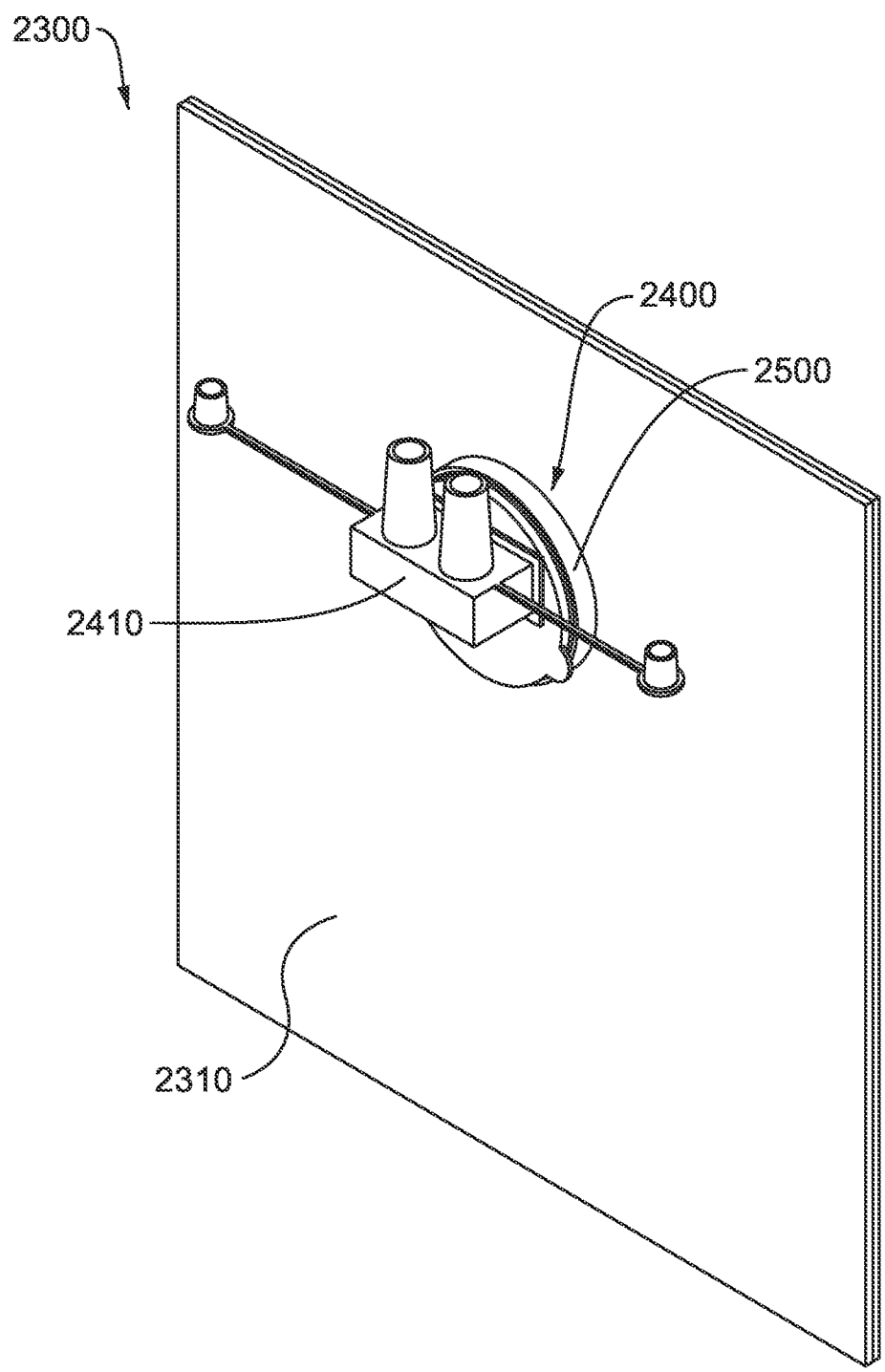
FIG. 38 is an isometric view of a liner assembly of the fluid collection system of FIG. 30, shown from above.
Figure 42:
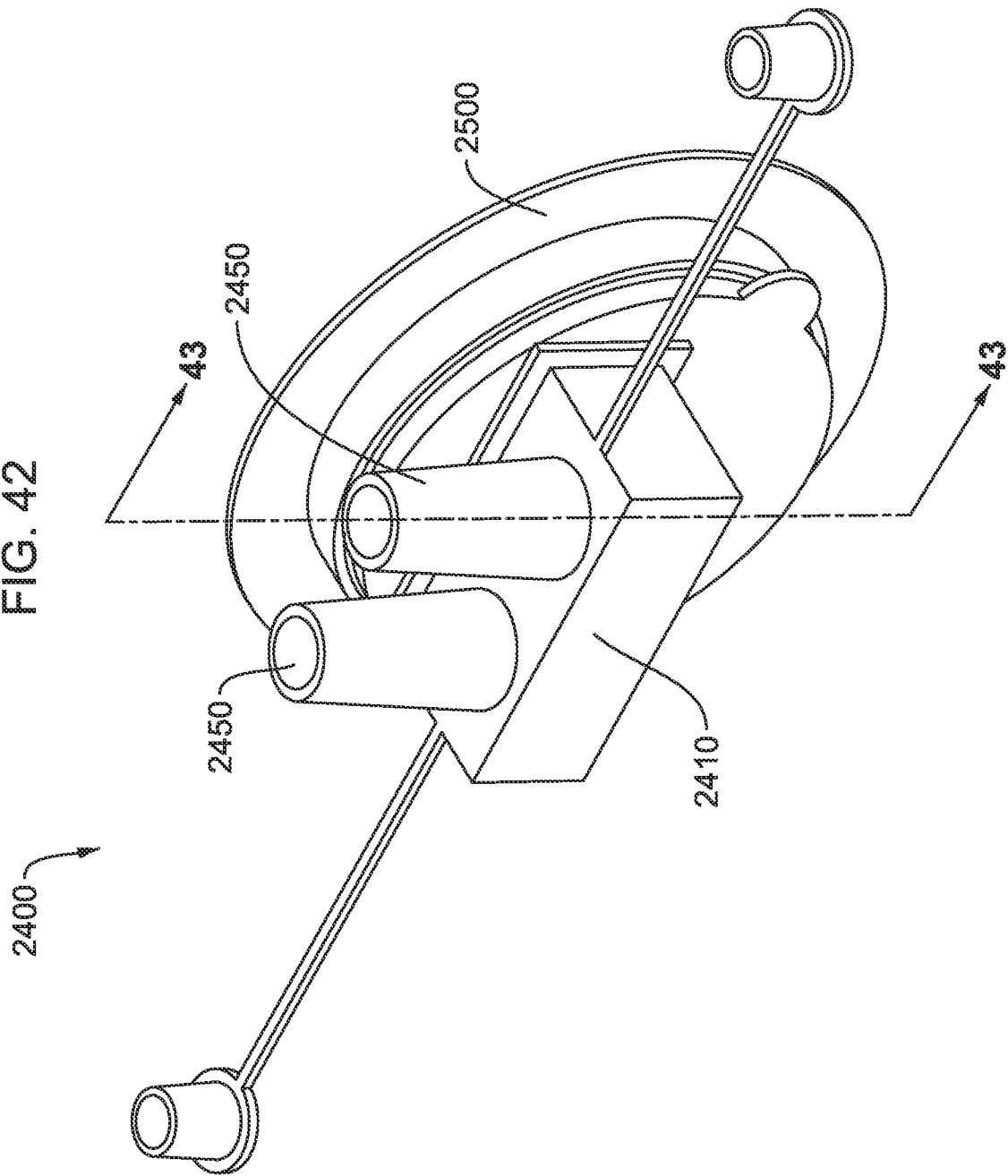
FIG. 42 is an isometric view of a fitment assembly of the fluid collection system of FIG. 30, shown from above.
Figure 43:
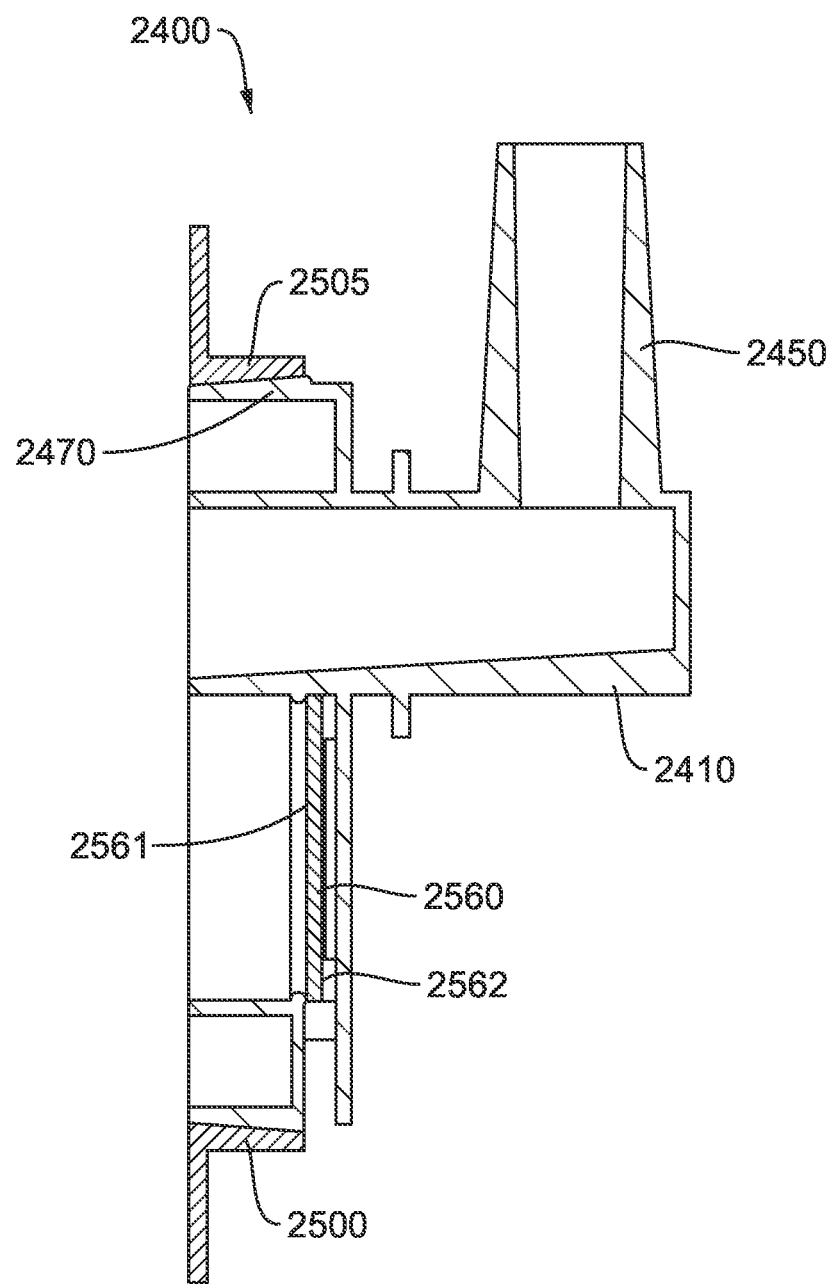
FIG. 43 is a cross-sectional view of the fitment assembly of FIG. 42 taken along line 43, shown from the side.

A second embodiment of the fluid collection system 2000 is shown in FIGS. 30-32 and may include a canister 2100, a lid 2200, a liner 2310, a fitment 2410, a gland 2500, a filter 2560, and a tether 2640. Together, the fitment 2410, the gland 2500 and the filter 2560 form a fitment assembly 2400, as shown in FIGS. 42-43. Together, the fitment assembly 2400 and the liner 2310 form a liner assembly 2300, as shown in FIG. 38. With respect to this embodiment, the terms "upper," "lower," "top," "bottom", "above" and "below" are discussed as shown in FIG. 31.

When the fluid collection system 2000 is in the closed position as shown in FIGS. 30-31, two chambers are formed: a fluid chamber 2002 and an interstitial chamber 2001. The fluid chamber 2002 may be substantially enclosed by the fitment assembly 2400 and the liner 2310. The interstitial chamber 2001 may be substantially enclosed by the canister 2100, the lid 2200, the fitment assembly 2400, and the liner 2310. A filter 2560 in the fitment assembly 2400 may separate the fluid chamber 2002 from the interstitial chamber 2001.

Figure 34:
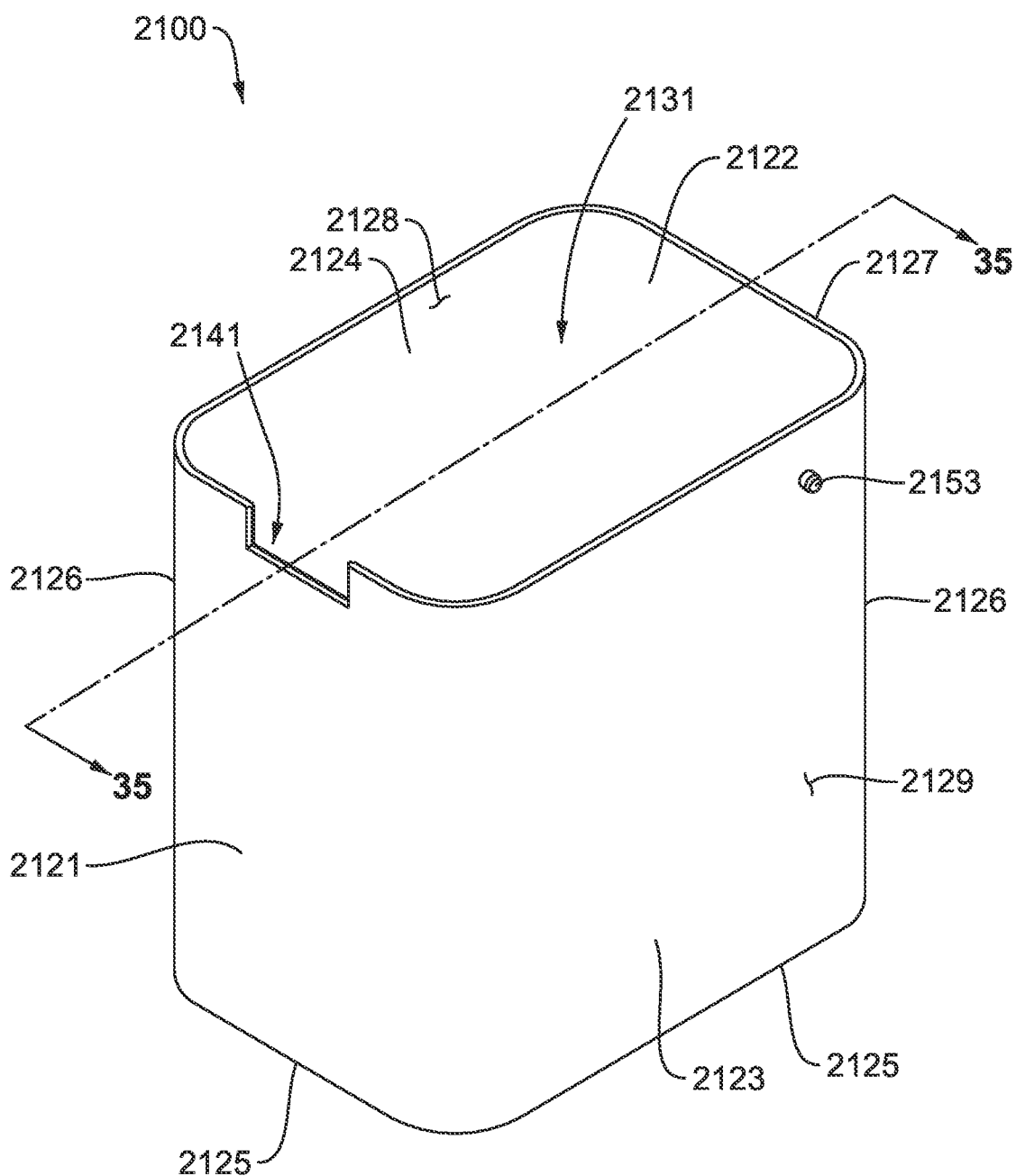
FIG. 34 is an isometric view of a canister of the fluid collection system of FIG. 30, shown from above.
Figure 35:
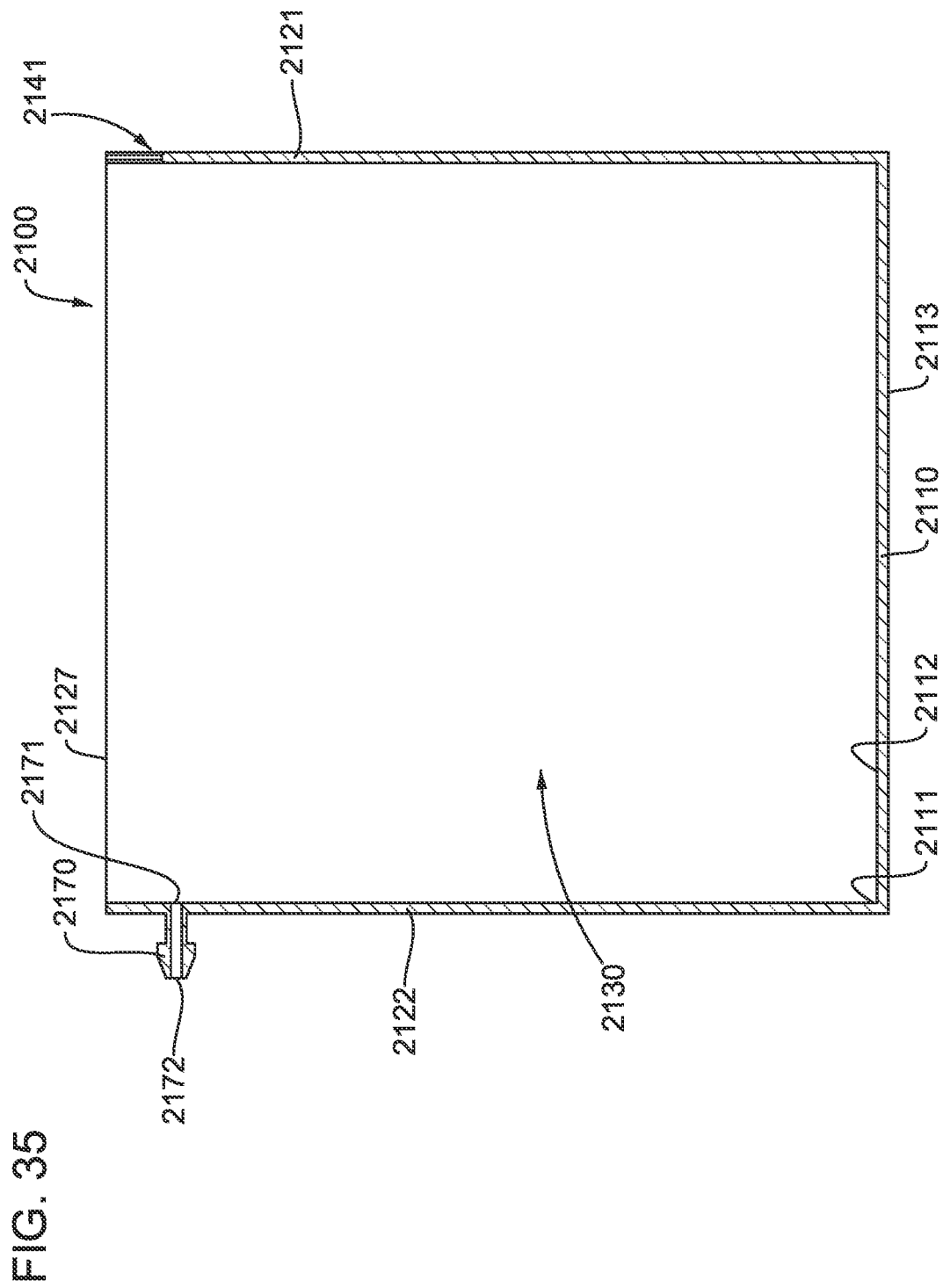
FIG. 35 is a cross-sectional view of the canister of FIG. 34 taken along line 35, shown from the side.

FIGS. 34-35 show the canister 2100 of the second embodiment, the canister 2100 having a bottom wall 2110, a first side wall 2121, a second side wall 2122, a third side wall 2123, and a fourth side wall 2124. The bottom wall 2110 has an interior surface 2112, an exterior surface 2113, and four ends 2111. The side walls 2121, 2122, 2123, 2124 of the canister each have a bottom end 2125, two side ends 2126, a top end 2127, an interior surface 2128, and an exterior surface 2129. The bottom end 2125 of each side wall is connected to an end 2111 of the bottom wall 2110. Each side end 2126 of each side wall is connected to a side end 2126 of an adjacent side wall.

In embodiments of canisters 2100 with four side walls, such as those shown in FIGS. 34-35, the first side wall 2121 may be opposite the second side wall 2122 and adjacent to the third side wall 2123 and the fourth side wall 2124, and the second side wall 2122 may also be adjacent to the third side wall 2123 and the fourth side wall 2124. However, the canister 2100 may be configured to have any number of side walls.

The top end 2127 of the first side wall 2121 of the canister 2100 may include a notch 2141. Although the notch 2141 is shown in the canister 2100 of the second embodiment, the notch 2141 could alternatively be included in the lid 2200. Furthermore, a portion of the notch 2141 could be included in the canister 2100 and a portion of the notch 2141 could be included in the lid 2200.

During use, the exterior surface 2113 of the bottom wall 2110 and the exterior surface 2129 of the side walls 2121, 2122, 2123, 2124 are exposed to the environment. Together, the interior surface 2112 of the bottom wall 2110 and the interior surface 2128 of the side walls form a cavity 2130 in the canister 2100. The cavity 2130 may have an open end such that the canister 2100 has an opening 2131 opposite the bottom wall 2110. The top ends 2127 of the side walls 2121, 2122, 2123, 2124 may at least partially surround the opening 2131 of the cavity 2130, and may form the open end of the canister 2100.

The canister 2100 may include an interstitial vacuum port 2170 having a vacuum source end 2172 that opens on the exterior of the canister 2100 and a cavity end 2171 that opens into the cavity 2130 of the canister 2100. In FIG. 35, the interstitial vacuum port 2170 is positioned on the second side wall 2122 of the canister 2100. However, the interstitial vacuum port 2170 could be positioned on any of the side walls 2121, 2122, 2123, 2124 of the canister 2100, or on the lid 2200.

Figure 36:
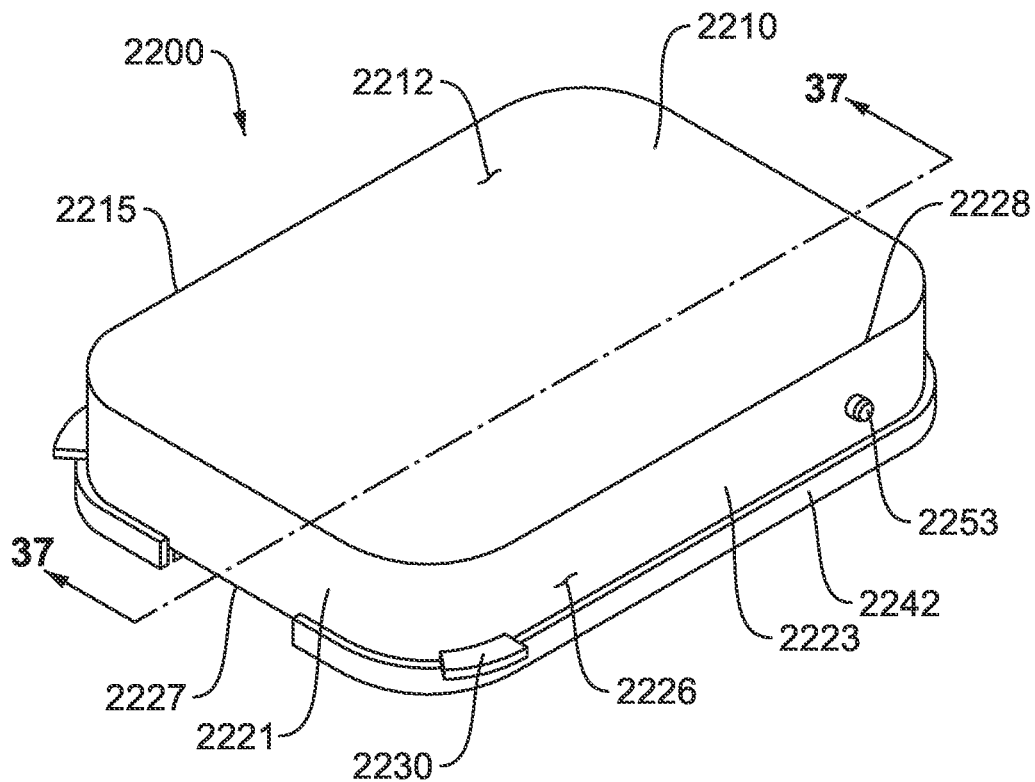
FIG. 36 is an isometric view of a lid of the fluid collection system of FIG. 30, shown from above.
Figure 37:
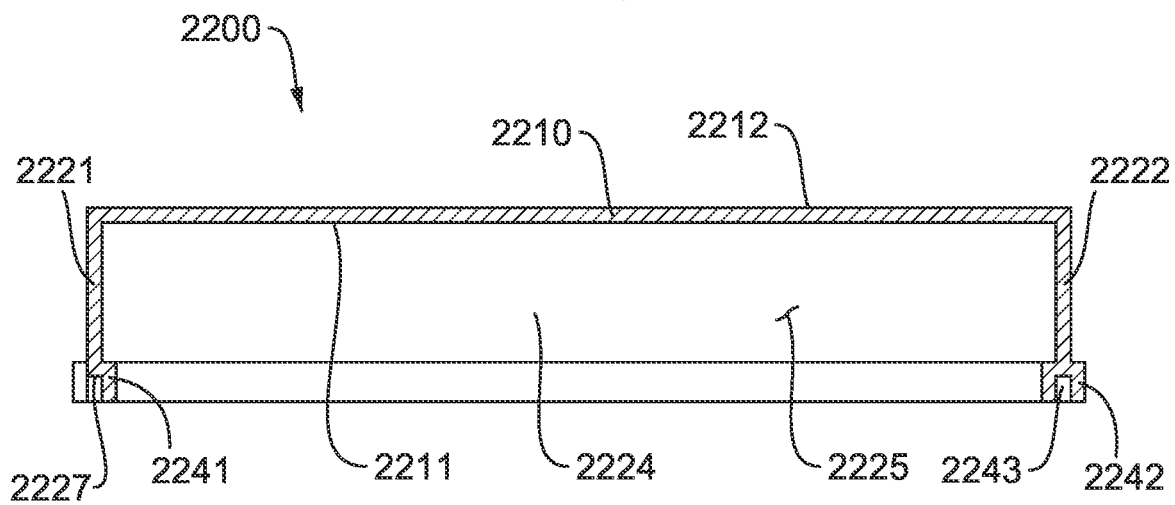
FIG. 37 is a cross-sectional view of the lid of FIG. 36 taken along line 37, shown from the side.

The fluid collection system 2000 also includes a lid 2200 as shown in FIGS. 36-37. The lid 2200 has an upper wall 2210, a first side wall 2221, a second side wall 2222, a third side wall 2223, and a fourth side wall 2224. The upper wall 2210 of the lid 2200 has an interior surface 2211, an exterior surface 2212, and four ends 2215. The side walls 2221, 2222, 2223, 2224 each have a bottom end 2227, a top end 2228, an interior surface 2225 and an exterior surface 2226. The top end 2228 of each side wall is connected to an end 2215 of the upper wall 2210. The lid 2200 may also have one or more tabs 2230 on one or more of the side walls 2221, 2222, 2223, 2224 to facilitate the opening and/or closing of the lid 2200.

An inner rib 2241 and an outer rib 2242 may extend along the bottom end 2227 of the side walls 2221, 2222, 2223, 2224 of the canister 2200. The inner rib 2241 and the outer rib 2242 may be substantially parallel, and separated by a groove 2243 that also extends along the bottom end 2227 of the side walls 2221, 2222, 2223, 2224. It is possible that the ribs 2241, 2242 are not present along at least a portion 2244 of the bottom end 2227 of one or more of the side walls 2221, 2222, 2223, 2224. Alternatively, one or both of the inner rib 2241 and the outer rib 2242 may be omitted from the lid.

In embodiments of lids 2200 with four side walls, such as those shown in FIGS. 36-37, the first side wall 2221 may be opposite the second side wall 2222 and adjacent to the third side wall 2223 and the fourth side wall 2223, and the second side wall 2222 may also be adjacent to the third side wall 2223 and the fourth side wall 2224. However, the lid 2200 may be configured to have any number of side walls.

The lid 2200 may be placed over the opening 2131 of the cavity 2130 of the canister 2100 to partially close the opening 2131. When the lid 2200 is in a closed position, the canister 2100 and the lid 2200 are in sealing engagement with one another around a portion of the opening 2131. The first side wall 2121 of the canister 2100 mates with the first side wall 2221 of the lid 2200. Likewise, the second, third, and fourth side walls 2122, 2123, 2124 of the canister 2100 mate with the second, third, and fourth side walls 2222, 2223, 2224 of the lid 2200, respectively. The bottom end 2227 of the side walls of the lid 2200 mate with the top end 2127 of the side walls of the canister 2100. More specifically, the top end 2127 of the side walls of the canister 2100 may be inserted into the groove 2243 near the bottom end 2227 of the side walls of the lid 2200.

A sealing engagement around a portion of the opening 2131 of the canister 2100 may be formed by one or more interference fits between the canister 2100 and the lid 2200. The interior surface 2128 of the side walls of the canister 2100 may have an interference fit with the exterior surface of the inner rib 2241 on the side walls of the lid 2200. The exterior surface 2129 of the side walls of the canister 2100 may have an interference fit with the interior surface of the outer rib 2242 on the side walls of the lid 2200. If the ribs 2241, 2242 are not present, the interior surface 2128 of the side walls of the canister 2100 may have an interference fit with the exterior surface 2226 of the side walls of the lid 2200, or the exterior surface 2129 of the side walls of the canister 2100 may have an interference fit with the interior surface 2225 of the side walls of the lid 2200.

Although the canister 2100 and the lid 2200 may be in sealing engagement around a portion of the opening 2131 of the canister 2100, the canister 2100 and the lid 2200 may define an aperture where the canister 2100 and lid 2200 are not in sealing engagement. The aperture may be located at the notch 2141 in the canister 2100. The notch 2141 in the canister 2100 may align with the portion of the bottom end 2227 of the side walls of lid 2200 along which the inner rib 2241 and the outer rib 2242 do not extend. The gap between the lid 2200 and the canister 2100 at the notch 2141 in the canister 2100 enables communication into and out of the cavity 2130 of the canister 2100.

The canister 2100 and the lid 2200 may optionally be coupled via a tether 2640. If a tether 2640 is used to couple the canister 2100 and the lid 2200, a pin 2153 may be included on the exterior surface 2129 of any of the side walls of the canister 2100. Likewise, a pin may be included on the exterior surface 2226 of any of the side walls of the lid 2200. The tether 2640 may be connected to the pin 2153 on the canister 2100 and the pin 2253 on the lid 2200. The pins 2153, 2253 may be omitted the tether is not used to couple the canister 2100 and the lid 2200.

Figure 33:
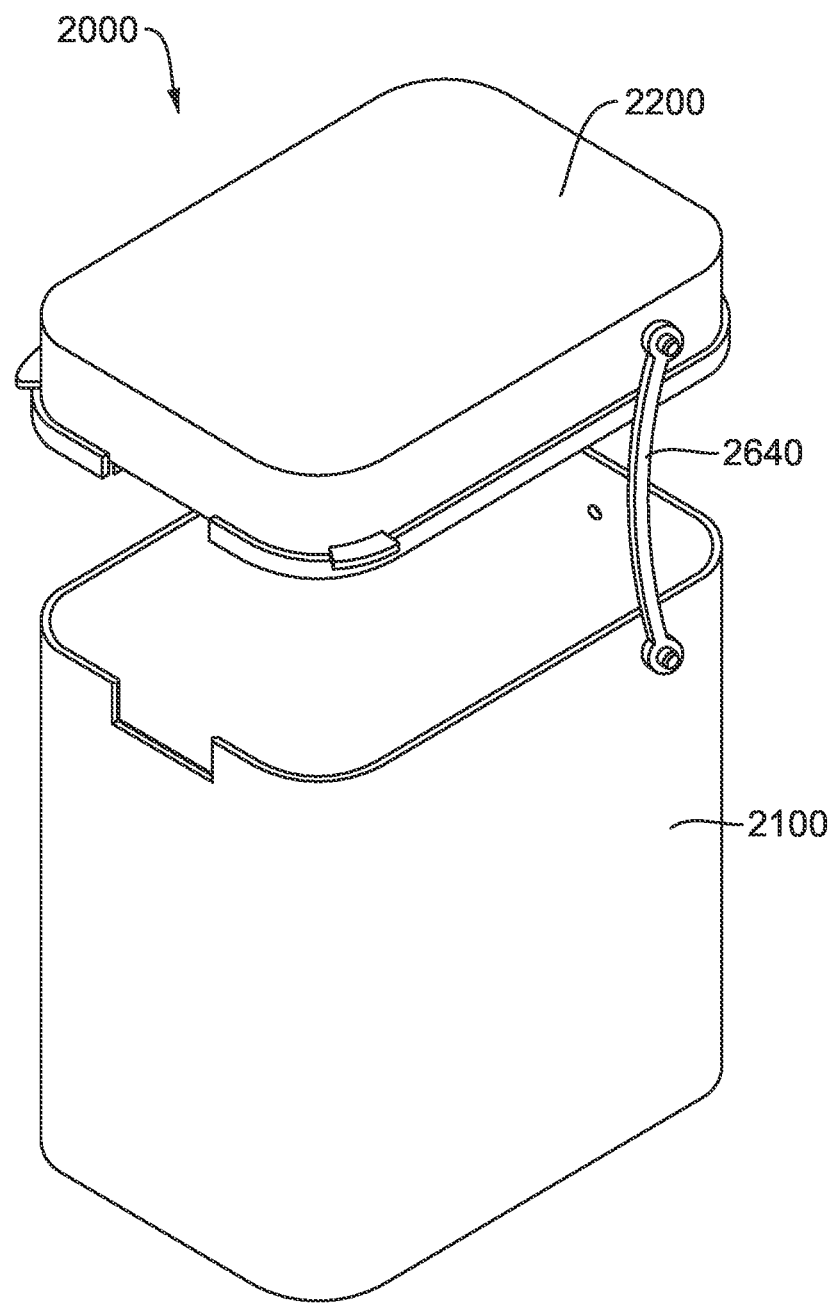
FIG. 33 is an isometric view of the fluid collection system of FIG. 30, shown from above in an open position.

The lid 2200 is moveable between a closed position shown in FIGS. 30-31 and an open position shown in FIG. 33. In the closed position, the lid 2200 and the canister 2100 are in sealing engagement with one another around a portion of the opening 2131. The exterior surface 2212 of the upper wall 2210 is exposed to the environment and the interior surface 2211 of the upper wall 2210 faces the cavity 2130 of the canister 2100 when the lid 2200 is in the closed position, as shown in FIGS. 30-31.

In the open position, the lid 2200 and the canister 2100 are not in sealing engagement with one another.

The fluid collection system 2000 also includes a liner assembly 2300 as shown in FIG. 38. The liner assembly 2300 (i.e. fluid receptacle) includes a liner 2310 and a fitment assembly 2400 which cooperate to substantially enclose a fluid chamber 2002.

Figure 39:
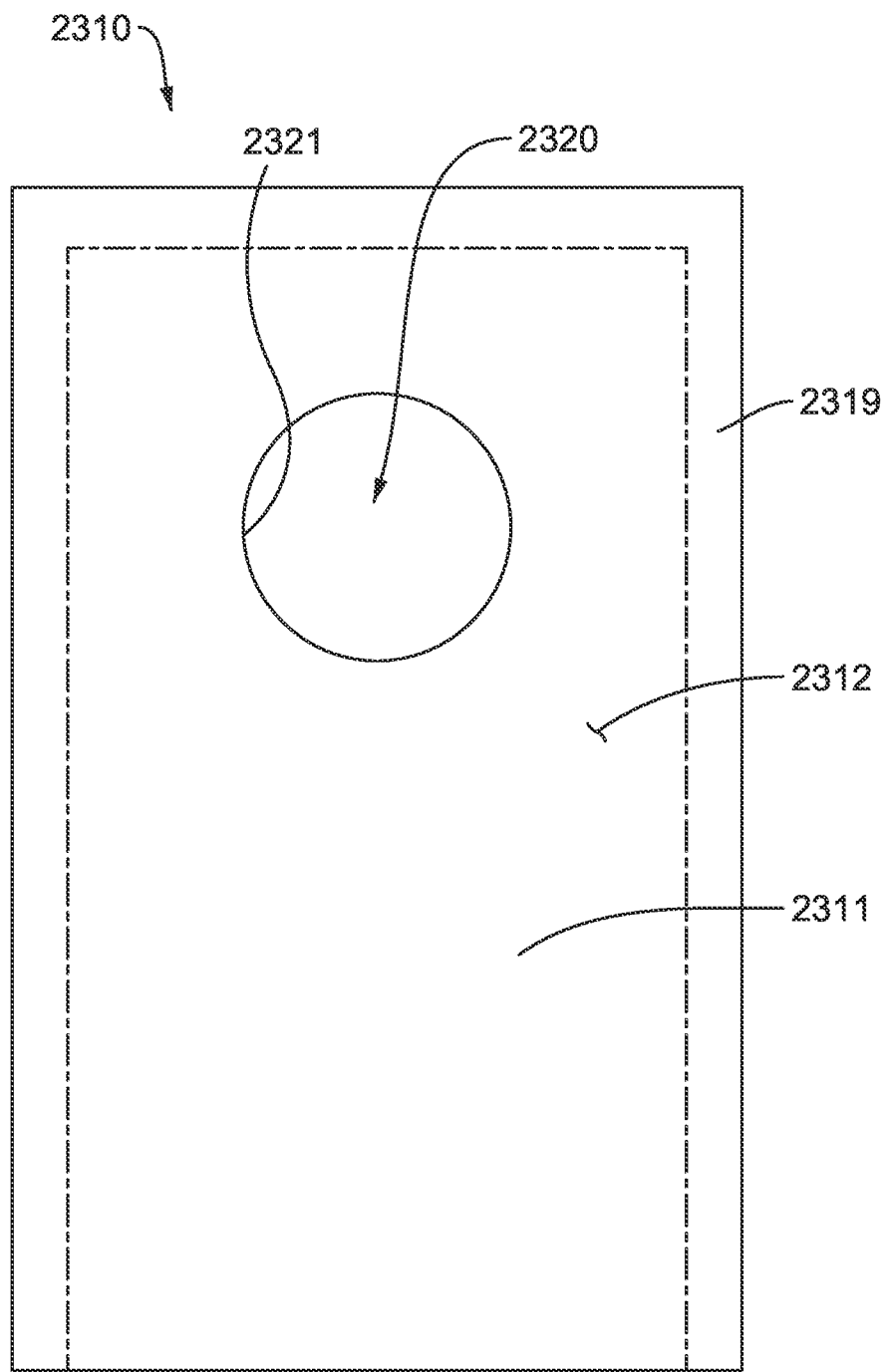
FIG. 39 is a side view of the liner of the liner assembly of FIG. 38.

The liner 2310 of the second embodiment is shown in FIG. 39. FIG. 40 shows the body 2311 of the liner 2310 before the liner 2310 is assembled. The body 2311 of the liner 2310 is made of a thin-walled material. The body 2311 has been folded along a fold line 2314 to create a first panel 2315 having four ends and a second panel 2316 having four ends. The first panel 2315 and the second panel 2316 are joined along one end by the fold, as shown in FIG. 41. The remaining three ends of the first panel 2315 form a first periphery 2317, and the remaining three ends of the second panel 2316 form a second periphery 2318. The first panel 2315 and the second panel 2316 are joined to one another by a seal 2319 extending along the first periphery 2317 and the second periphery 2318 as shown in FIG. 39. The seal 2319 extends from the dashed line in FIG. 39 toward the first periphery 2317 and the second periphery 2318 of the liner 2310. The seal may be about ⅜" wide, or may have a different width as long as an appropriate seal strength is maintained when the liner 2310 is exposed to vacuum and/or contains fluid.

The liner 2310 of the second embodiment has an opening 2320 in the body 2311 of the liner 2310. The opening 2320 may be located on either the first panel 2315 or the second panel 2316. The opening 2320 may be substantially circular, or could be any number of other shapes. The body 2311 has a third periphery 2321 at the edge of the opening 2320. The gland 2500, described below, is configured to be inserted into the opening 2320 in the body 2311 of the liner 2310.

As shown in FIG. 31, the liner 2310 is positioned in the cavity 2130 of the canister 2100. The liner 2310 has a canister-facing surface 2312 and a fluid chamber surface 2313. When the liner assembly 2300 is ready for use, the liner 2310 is oriented such that the canister-facing surface 2312 is on the outside (and may face the interior surface 2112 of the bottom wall 2110 and the interior surfaces 2128 of the side walls 2121, 2122, 2123, 2124 of the canister 2100 when inserted into the canister 2100) and the fluid chamber surface 2313 is on the inside.

A fitment assembly 2400 of the second embodiment is shown in FIGS. 42-43. The fitment assembly 2400 includes a fitment 2410, a gland 2500, and a filter 2560. The fitment assembly 2400 also includes two fluid ports 2450 and a fluid chamber vacuum port 2440 which may be located on the fitment 2410, as shown in FIG. 47.

Figure 44:
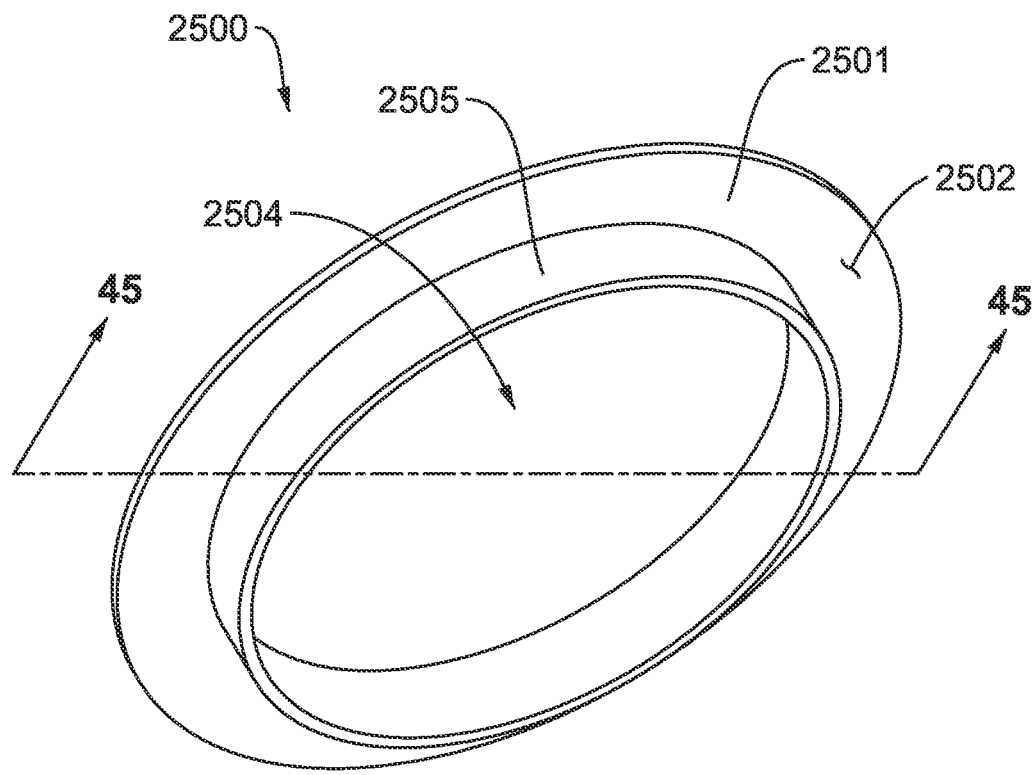
FIG. 44 is an isometric view of a gland of the fitment assembly of FIG. 42, shown from above.
Figure 45:
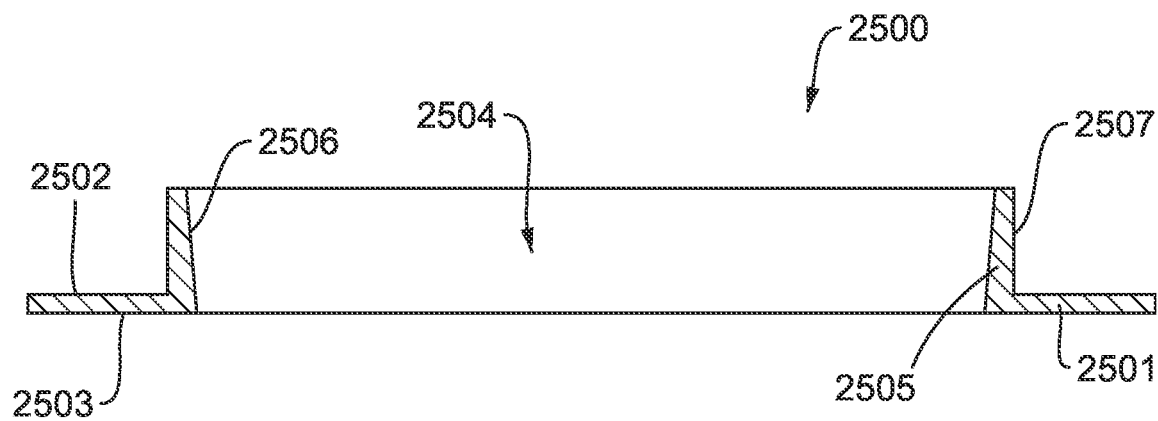
FIG. 45 is a cross-sectional view of the gland of FIG. 44 taken along line 45, shown from the side.

The gland 2500 is shown in FIGS. 44-45. The gland 2500 has a disc-shaped base 2501. The base 2501 has a first surface 2502, a second surface 2503, and an opening 2504. A rib 2505 protrudes from the first surface 2502 of the base 2501 and surrounds the opening 2504. The rib 2505 has an inner surface 2506 facing the opening 2504 and an outer surface 2507 that faces away from the opening 2504.

The gland 2500 and the liner 2310 are in sealing engagement with one another. The gland 2500 and the liner 2310 are coupled by inserting the rib 2505 of the gland 2500 into the opening 2320 in the body 2311 of the liner 2310. The first surface 2502 of the base 2501 of the gland 2500 is in sealing engagement with the fluid chamber surface 2313 of the liner 2310 near the third periphery 2321 surrounding the opening 2320 of the liner 2310.

Figure 46:
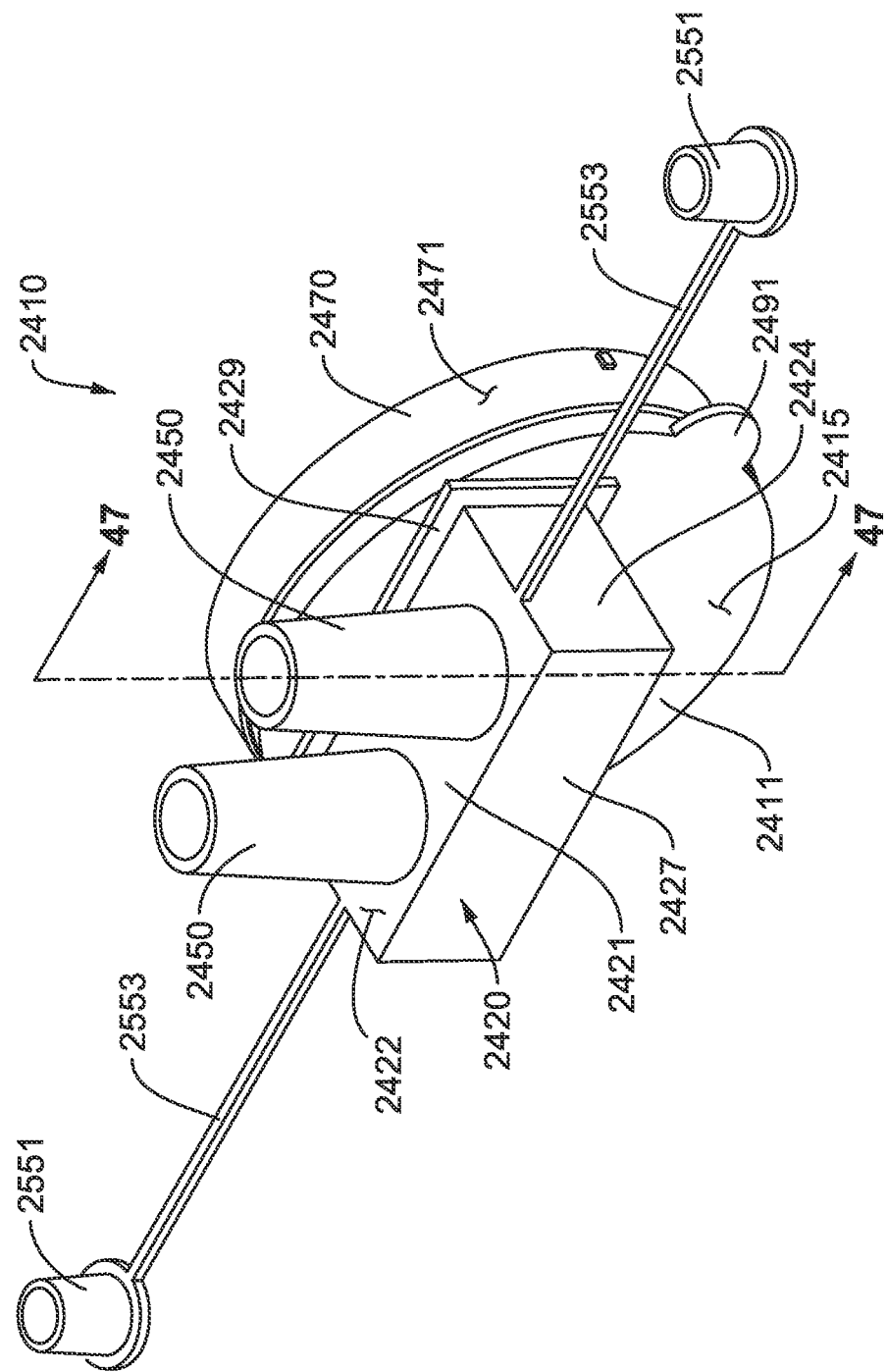
FIG. 46 is an isometric view of a fitment of the fitment assembly of FIG. 42, shown from above.
Figure 47:
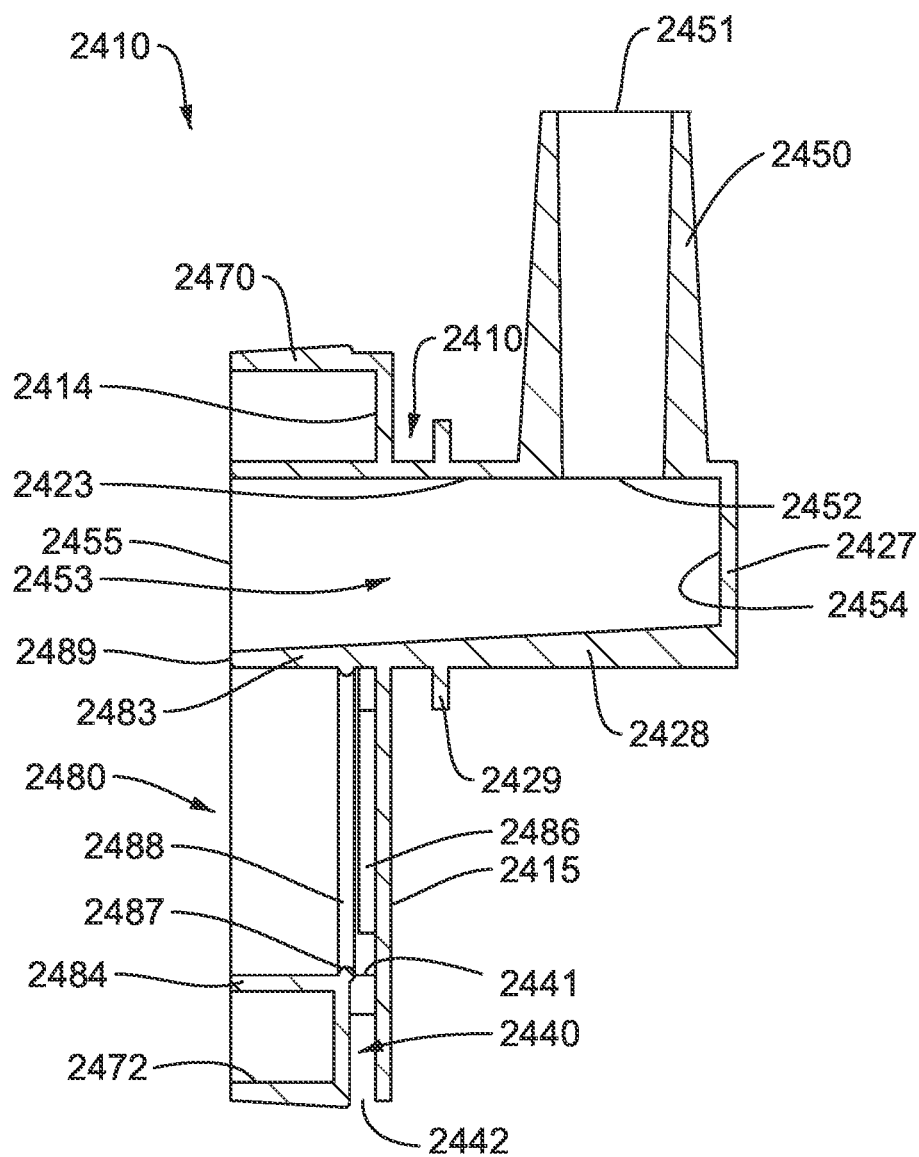
FIG. 47 is a cross-sectional view of the fitment of FIG. 46 taken along line 47, shown from the side.
Figure 48:
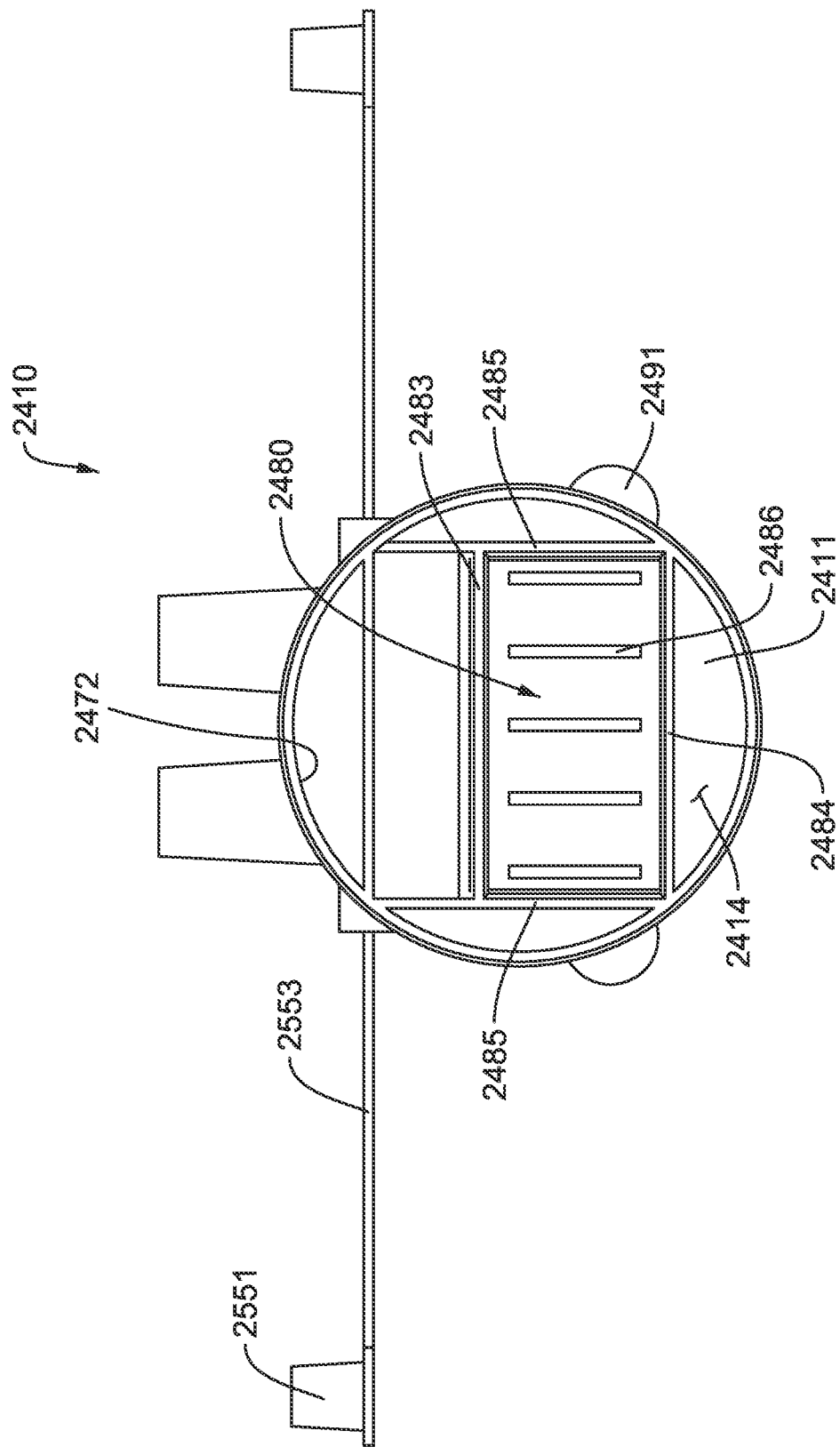
FIG. 48 is a back view of the fitment of FIG. 46.

The fitment 2410 is shown in FIGS. 46-48. Two fluid ports 2450 on the fitment 2410 allow fluid to enter and exit the fluid chamber 2002. A fluid chamber vacuum port 2440 on the fitment 2410 may allow a vacuum in the interstitial chamber 2001 to be transmitted to the fluid chamber 2002.

The fitment 2410 has a base 2411 having a fluid chamber surface 2414 and an exterior surface 2415. When the fitment 2410 is positioned as shown in FIG. 31, the fluid chamber surface 2414 of the base 2411 faces the second side wall 2122 of the canister 2100, and the exterior surface 2415 of the base 2411 faces the first side wall 2121 of the canister 2100. One or more thumb tabs 2491 extend from the base 2411 of the fitment 2410 to aid in removal of the fitment 2410 from the gland 2500.

A first rib 2470 protrudes from the fluid chamber surface 2414 of the base 2411 of the fitment 2410 and surrounds at least a portion of the fluid chamber surface 2414 of the base 2411. The first rib 2470 has an inner surface 2472 and an outer surface 2471.

A protrusion 2420 extends from the exterior surface 2415 of the base 2411 of the fitment 2410. The protrusion 2420 has an end wall 2427 connected to the exterior surface 2415 of the base 2411 by an upper wall 2421, two side walls 2424, and a bottom wall 2428. The upper wall 2421, side walls 2424, end wall 2427 and bottom wall 2428 each have an interior surface that forms part of the wall of the fluid chamber 2002, and an exterior surface that is exposed to the environment.

The protrusion 2420 on the fitment 2410 has a rib 2429 that projects outwardly from the protrusion 2420. More specifically, the rib 2429 projects from the upper wall 2421, the side walls 2424, and the bottom wall 2428 of the protrusion 2420, and is substantially parallel to the exterior surface 2415 of the base 2411. A groove 2430 is formed between the rib 2429 and the exterior surface 2415 of the base 2411.

The fitment 2410 may also include a filter guard 2480 that protects the filter 2560 from accidental splashing, which could result in the same issues discussed with the first embodiment. In addition, the filter guard 2480 of the second embodiment also holds the filter 2560 in place within the fitment 2410. The filter guard 2480 extends from a first end 2488 at the fluid chamber surface 2414 of the base 2411 of the fitment 2410 to a second end 2489 opposite the first end 2488. The filter guard 2480 has an upper wall 2483, a bottom wall 2484, and two side walls 2485 which extend from the fluid chamber surface 2414 of the base 2411 of the fitment 2410.

The filter guard 2480 includes features to hold the filter 2560 in place. Filter support ribs 2486 are positioned within the filter guard 2480 and extend from the fluid chamber surface 2414 of the fitment 2410 in the area substantially enclosed by the upper wall 2483, bottom wall 2484, and two side walls 2485. A filter retaining rib 2487 protrudes inwardly from the upper wall 2483, the bottom wall 2484, and the two side walls 2485 of the filter guard 2480. During use, the second end 2489 of the filter guard 2480 opens into the fluid chamber 2002. When the fitment 2410 is positioned as shown in FIG. 31, the filter guard 2480 is positioned below the fluid ramp 2453. Therefore, the filter 2560 is positioned below the fluid ports 2450 which eliminates the need for a fluid port check valve for the same reasons discussed in the first embodiment.

A sealing engagement is formed between the fitment 2410 and the gland 2500, as shown in FIG. 43. The fitment 2410 and the gland 2500 are coupled by mating the first rib 2470 of the fitment 2410 with the rib 2505 of the gland 2500. The inner surface 2506 of the rib 2505 of the gland 2500 may have an interference fit with the outer surface 2471 of the first rib 2470 of the fitment 2410 to create the sealing engagement between the fitment 2410 and the gland 2500.

When moving the fluid collection system 2000 to the closed position, the protrusion 2420 of the fitment 2410 may be inserted into the notch 2141 in the canister 2100 before the lid 2200 is closed. The bottom wall 2428 and the side walls 2424 of the protrusion 2420 are in sealing engagement with the notch 2141 on the canister 2100. The upper wall 2421 of the protrusion 2420 is in sealing engagement with the bottom end 2227 of the first side wall 2221 of the lid 2200. Specifically, the bottom end 2227 of the first side wall 2221 of the lid 2200 may be inserted into the groove 2430 on the upper wall 2421 of the protrusion 2420, and the edges of the notch 2141 on the canister 2100 are inserted into the groove 2430 on the side walls 2424 and the bottom wall 2428 of the protrusion 2420 of the fitment 2410. The fitment assembly 2400 may have a sealing surface that seals to one or more of the canister 2100 and the lid 2200. The groove 2430 of the fitment 2410 may be a sealing surface that allows the fitment assembly 2400 to seal to the canister 2100 and the lid 2200.

The canister 2100, the lid 2200, and the fitment 2410 are in sealing engagement when the fluid collection system 2000 is in the closed position. As discussed above, the canister 2100 and the lid 2200 are in sealing engagement with one another around a portion of the opening 2131 of the canister 2100. However, the canister 2100 and the lid 2200 are not in sealing engagement at the notch 2141 in the canister 2100. The fitment 2410 form a seal with the canister 2100 and the lid 2200. The fitment may form a seal with the canister 2100 near the notch 2141. The fitment 2410 is sealingly engaged to at least the notch 2141 in the canister 2100, and to a portion of the lid 2200. Together, the fitment assembly 2400 and the lid 2200 substantially close the opening 2131 in the canister 2100.

An interstitial chamber 2001 is formed when the fluid collection system 2000 is in the closed position, as shown in FIG. 31. The interstitial chamber 2001 is the space substantially enclosed by the canister 2100, the liner 2310, the lid 2200, and the fitment assembly 2400. In order to enable the interstitial chamber 2001 to maintain vacuum pressure, the canister 2100 may be in sealing engagement with the lid 2200 and the fitment 2410, the lid 2200 may be in sealing engagement with the fitment 2410, the fitment 2410 may be in sealing engagement with the gland 2500, and the gland 2500 may be in sealing engagement with the liner 2310. Preferably, the liner 2310 may be sealingly engaged with the gland 2500 during the manufacturing process. Additionally, the fitment 2410 may be sealingly engaged with the gland 2500 during the manufacturing process. If the fluid chamber vacuum port 2440 uses a pass-through design, the filter 2560 may also be in sealing engagement with the fitment 2410 to substantially enclose the interstitial chamber 2001, and the filter 2560 may separate the interstitial chamber 2001 and the fluid chamber 2002.

When a vacuum is applied to the interstitial chamber 2001, the liner 2310 expands in the cavity 2130 of the canister 2100. The canister-facing surface 2312 of the liner 2310 may be drawn toward the bottom wall 2110 and the side walls 2121, 2122, 2123, 2124 of the canister 2100. A vacuum source 2700, such as a vacuum pump, is used to provide a vacuum. The vacuum is communicated to the interstitial chamber 2001 by coupling the vacuum source 2700 to the vacuum source end 2172 of the interstitial vacuum port 2170.

The fitment 2410 includes two fluid ports 2450 that allow fluid to enter the fluid chamber 2002. Each fluid port 2450 includes an opening in the upper wall 2421 of the protrusion 2420. The patient end 2451 of each fluid port 2450 may protrude from the upper surface 2422 of the upper wall 2421 of the protrusion 2420, such that a patient tube may be connected to the patient end 2451 of the fluid port 2450. The fluid chamber end 2452 of each fluid port 2450 opens proximate the lower surface 2423 of the upper wall 2421.

The fluid chamber end 2452 of both fluid ports 2450 open into a fluid ramp 2453. The fluid ramp 2453 extends from a first end 2454 proximate the end wall 2427 of the protrusion 2420 to a second end 2455 that opens within the rib 2470. A portion of the bottom wall of the fluid ramp 2453 may be formed by one or more of the upper wall 2483 of the filter guard 2480 and the bottom wall 2428 of the protrusion 2420. During use, fluid enters the first end 2454 of the fluid ramp 2453 from the fluid ports 2450 and travels along the fluid ramp 2453 to the second end 2455, where it enters the fluid chamber 2002.

As discussed in the first embodiment, the second embodiment may optionally include a fluid port check valve (not shown) coupled to the fluid port 2450 to allow one-directional flow of fluid through the fluid port 2450. However, because the filter 2560 is positioned below the fluid ports 2450, a fluid port check valve is not needed for the same reasons discussed in the first embodiment.

The fitment 2410 includes a fluid chamber vacuum port 2440 through which a vacuum is applied to the fluid chamber 2002. The fluid chamber vacuum port 2440 may preferably be an opening in the fitment 2410 that extends between the first rib 2470 of the fitment 2410 and the bottom wall 2484 of the filter guard 2480, and allows gas to move between the fluid chamber 2002 and the interstitial chamber 2001. The fluid chamber vacuum port 2440 has a fluid chamber end 2441 located on the bottom wall 2484 of the filter guard 2480. An interstitial chamber end 2442 of the fluid chamber vacuum port 2440 opens on the first rib 2470 of the fitment 2410. Preferably, the interstitial chamber end 2442 of the fluid chamber vacuum port 2440 opens in an area of the first rib 2470 that will not be closed by the gland 2500 when the gland 2500 and the fitment 2410 are sealingly engaged.

The vacuum source 2700 is connected to the interstitial chamber 2001, resulting in a reduced pressure in the interstitial chamber 2001. The reduced pressure in the interstitial chamber 2001 may cause air from the fluid chamber 2002 to pass through the fluid chamber vacuum port 2440 and into the interstitial chamber 2001, thereby creating a vacuum in the fluid chamber 2002. In this pass-through configuration, the fluid chamber 2002 is upstream of the interstitial chamber 2001. The pass-through configuration may be preferred over other configurations where the fluid chamber vacuum port 2440 is independently connected to the vacuum source 2700 because the user does not need to connect a vacuum tube to the fluid chamber 2002 during each procedure. However, either configuration of fluid chamber vacuum ports 2440 may be used.

A filter 2560 shown in FIG. 43 is coupled to the fluid chamber vacuum port 2440. Similar to the filter of the first embodiment, the filter 2560 of the second embodiment has two purposes: removing bacteria, particulates and other solid matter from air flowing toward the vacuum source 2700, and acting as a vacuum shut-off. The materials used to make the filter in the first embodiment may also be used for the filter of the second embodiment. However, the filter 2560 of the second embodiment is square shaped and substantially planar, having two opposing surfaces: an upstream surface 2561 and a downstream surface 2562.

The filter 2560 is inserted into the filter guard 2480 of the fitment 2410. The downstream surface 2562 of the filter 2560 may be in communication with the interstitial chamber 2001 and the vacuum source 2700, and rests on the filter support ribs 2486 within the filter guard 2480. The upstream surface 2561 of the filter 2560 is in communication with the fluid chamber 2002 and is held in place by the filter retaining rib 2487. The periphery of the filter 2560 may be in sealing engagement with the filter retaining rib 2487, or the upper wall 2483, the bottom wall 2484, and the side walls 2485 of the filter guard 2480, or combinations thereof. During use, air may move through the filter 2560 in a downstream direction, from the fluid chamber 2002, through the filter 2560, and toward the fluid chamber vacuum port 2440, the interstitial chamber 2001, and the vacuum source 2700.

For the same reasons discussed in the first embodiment, any unused fluid ports 2450 in the second embodiment should be capped during the procedure. In the second embodiment, the fluid port caps 2551 may be connected to or integrally molded with the fitment 2410. Each fluid port cap 2551 is connected to the protrusion 2420 on the fitment 2410 by a bridge 2553.

The open position of the fluid collection system 2000 is shown in FIG. 33. The lid 2200 is in the open position, and is not sealingly engaged with the canister 2100. In FIG. 33, the liner assembly 2300 has not yet been inserted into the canister 2100. When the liner assembly 2300 is inserted into the canister 2100, the liner 2310 is positioned within the cavity 2130 of the canister 2100 and the fitment 2410 is inserted into the notch 2141 of the canister 2100.

The closed position of the fluid collection system 2000 is shown in FIGS. 30-31. The liner assembly 2300 may be inserted into the canister 2100, such that the liner 2310 is positioned within the cavity 2130 of the canister 2100 and the fitment 2410 is inserted into the notch 2141 of the canister 2100. The lid 2200 may be in the closed position, and the canister 2100 and the lid 2200 may be in sealing engagement with one another. The fitment 2410 may be in sealing engagement with the canister 2100 and the lid 2200. The fitment 2410 may be in sealing engagement with the gland 2500 and the filter 2560. The gland 2500 may be in sealing engagement with the liner 2310. Thus, the interstitial chamber 2001 may be sealed such that vacuum applied via the interstitial vacuum port 2170 is substantially maintained.

When using the fluid collection system 2000, the lid 2200 begins in the open position as shown in FIG. 33. The user then inserts the liner assembly 2300 into the canister 2100. The fitment 2410 is inserted into the notch 2141 of the canister 2100 so that the protrusion 2420 on the fitment 2410 rests in the notch 2141 of the canister 2100. The sides of the notch 2141 are inserted into the groove 2430 formed between the rib 2429 on the protrusion 2420 of the fitment 2410 and the exterior surface 2415 of the base 2411 of the fitment 2410. At the same time, the liner 2310 is positioned within the cavity 2130 of the canister 2100.

Next, the fluid collection system 2000 is moved to the closed position as shown in FIGS. 30-31. The lid 2200 is moved to a closed position and the interstitial chamber 2001 is formed. A patient tube is connected to the patient end 2451 of the fluid port 2450 on the fitment 2410. Any unused fluid ports 2450 are capped.

Vacuum is applied to the interstitial chamber 2001. A first method for applying the vacuum to the interstitial chamber 2001 is by physically connecting the vacuum source 2700 to the interstitial vacuum port 2170 (e.g., connecting a tube or other conduit). A second method for applying the vacuum to the interstitial chamber 2001 is by adjusting a regulator or on/off valve associated with the vacuum source 2700, such that the tube or other conduit between the vacuum source 2700 and the interstitial vacuum port 2170 may remain connected between procedures. Air is drawn out of the interstitial chamber 2001 through the interstitial vacuum port 2170 and toward the vacuum source 2700. The vacuum in the interstitial chamber 2001 may cause the liner 2310 to expand and at least partially conform to the interior surface 2112 of the bottom wall 2110 and the interior surface 2128 of the side walls 2121, 2122, 2123, 2124 of the canister 2100. The vacuum in the interstitial chamber 2001 may also draw air out of the fluid chamber 2002 through the fluid chamber vacuum port 2440. Therefore, a vacuum may be applied to both the interstitial chamber 2001 and the fluid chamber 2002.

Fluid from the patient flows along the patient tube, through the fluid port 2450 and the fluid ramp 2453, and into the fluid chamber 2002 where the fluid is collected. If the fluid chamber 2002 reaches its capacity (the fluid level in the fluid chamber 2002 rises high enough to saturate the upstream surface 2561 of the filter 2560), the vacuum to the fluid chamber 2002 is shut off, even though vacuum may still be applied to the interstitial chamber 2001 by the interstitial vacuum port 2170.

When the user is ready to remove the liner assembly 2300 from the canister 2100 (for example, at the end of a procedure or when the fluid chamber 2002 reaches its capacity), the vacuum source 2700 is physically disconnected from the interstitial vacuum port 2170, or the vacuum source 2700 is turned off using the regulator or on/off switch. The vacuum is no longer applied to the interstitial chamber 2001, and therefore the vacuum is also no longer applied through the fluid chamber vacuum port 2440 to the fluid chamber 2002. The lid 2200 is moved to the open position. The liner assembly 2300 is removed from the canister 2100 by sliding the fitment 2410 out of the notch 2141 in the canister 2100, and removing the liner 2310 from the cavity 2130 of the canister 2100.

The fluid may then be removed from the fluid chamber 2002. The fitment 2410 may be removed from the gland 2500, allowing the gland 2500 to be used as a pour spout. The thumb tabs 2491 on the fitment 2410 may be used to assist in removal of the fitment 2410 from the gland 2500. The gland 2500 has a dual functionality by both connecting the fitment 2410 to the liner 2310, and acting as a pour spout to allow fluid to be removed from the fluid chamber 2002. Fluid is poured out of the fluid chamber 2002 through the gland 2500. The liner assembly 2300 may then be disposed using standard medical waste disposal techniques.

Figure 49:
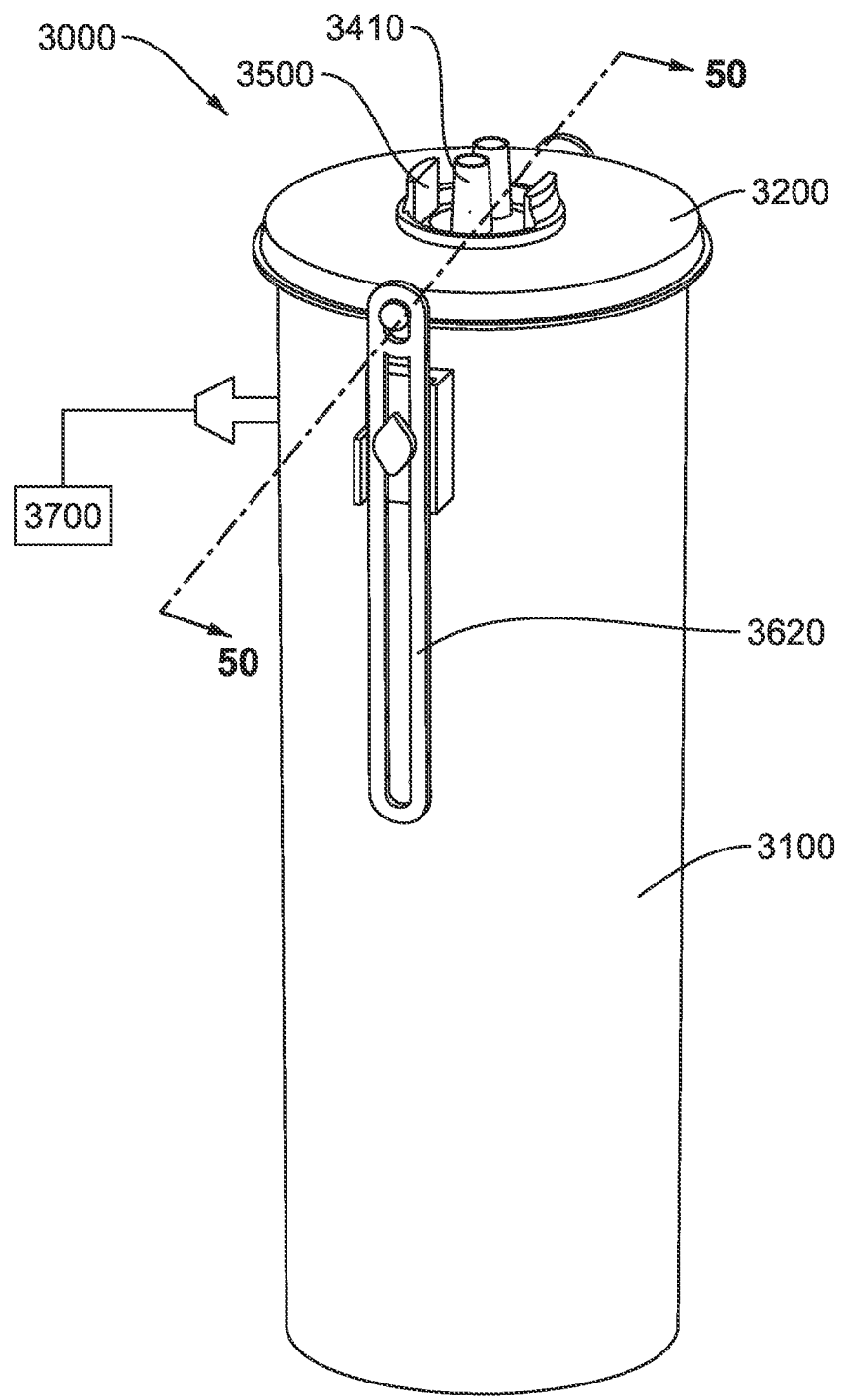
FIG. 49 is an isometric view of a third embodiment of the fluid collection system, shown from above in a closed position, according to certain aspects of the present application.
Figure 50:
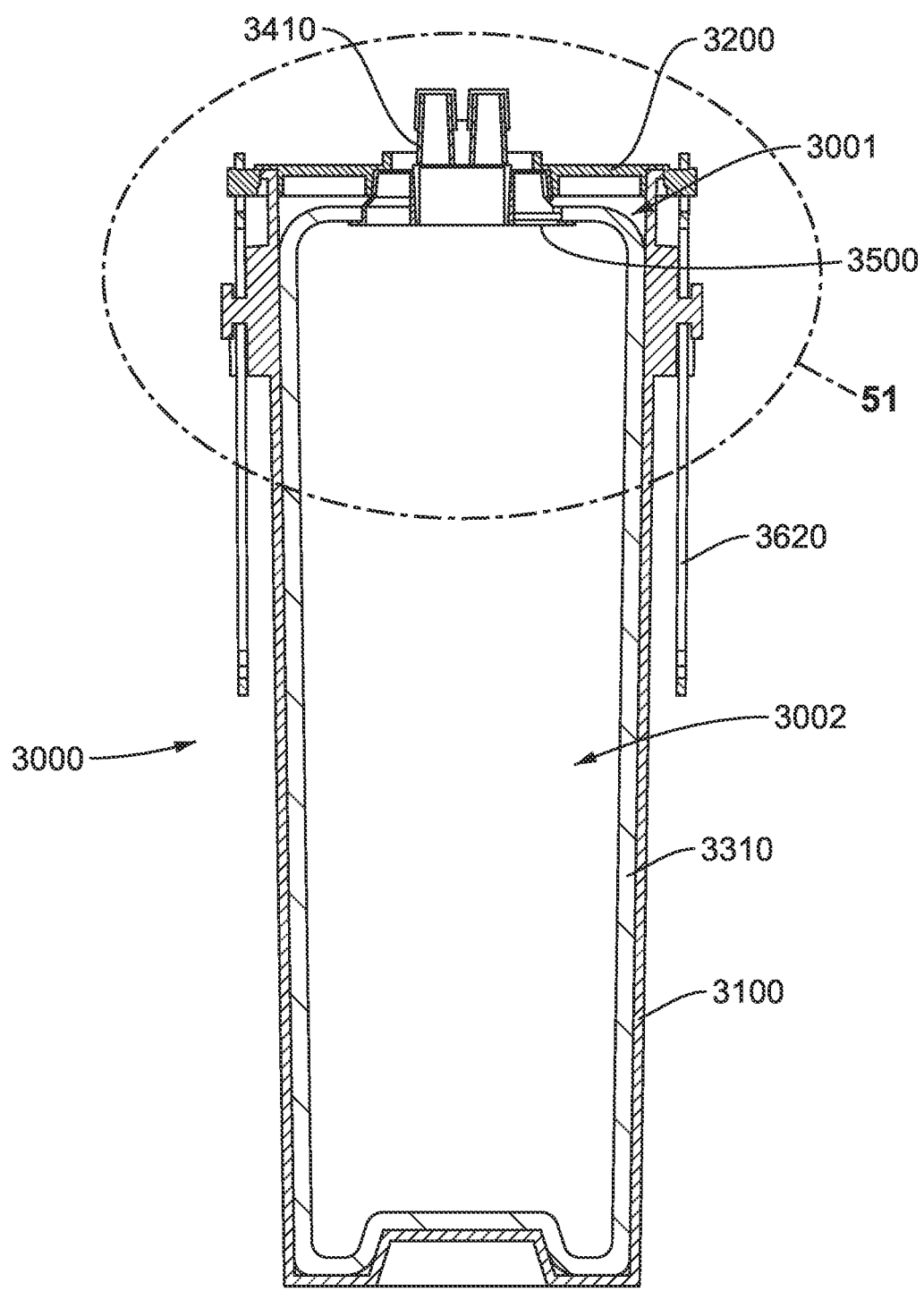
FIG. 50 is a cross-sectional view of the fluid collection system of FIG. 49 taken along line 50, shown from the side in a closed position.
Figure 51:
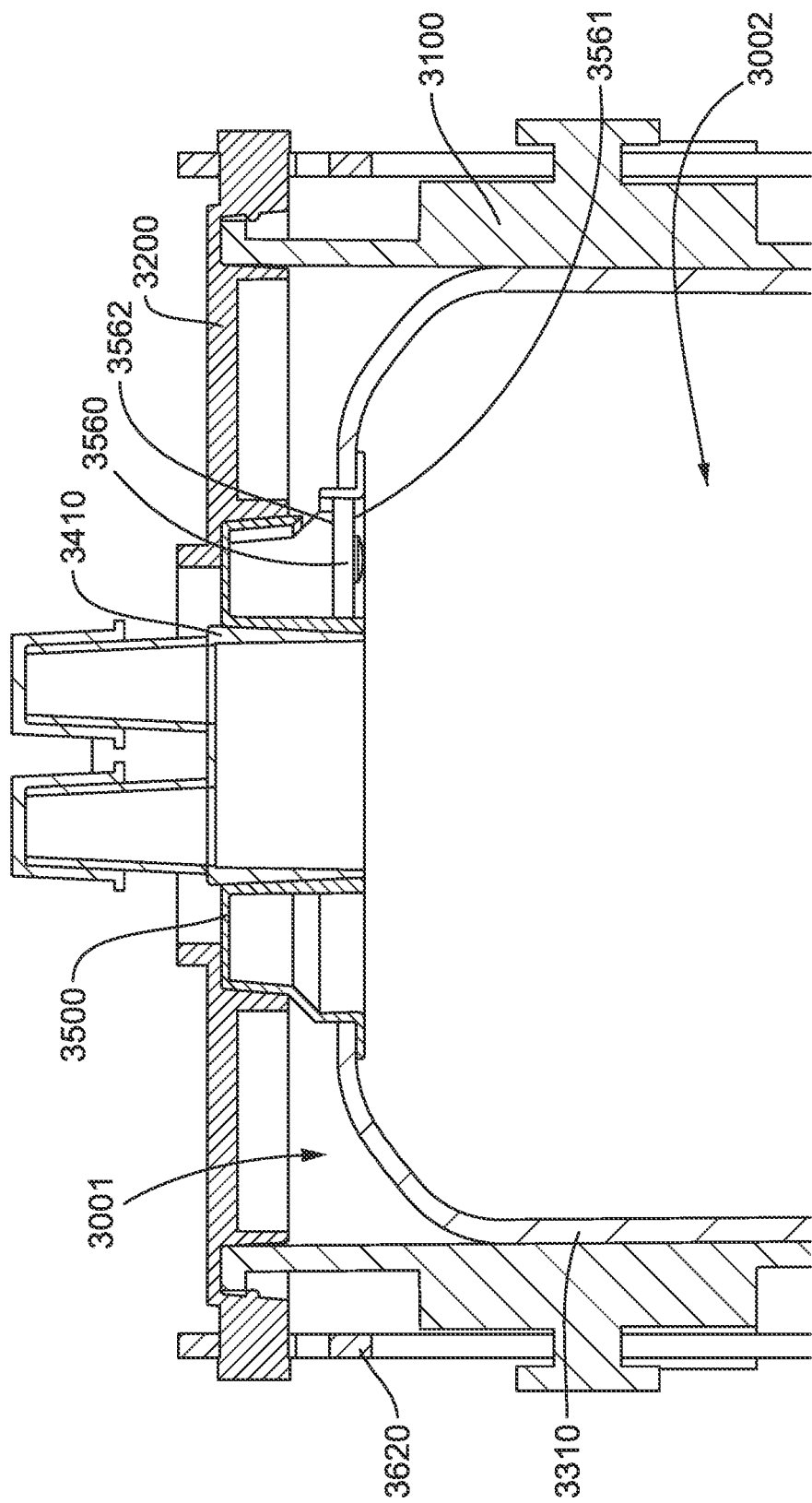
FIG. 51 is a detailed cross-sectional view of the fluid collection system of FIG. 51, shown from the side in a closed position.
Figure 60:
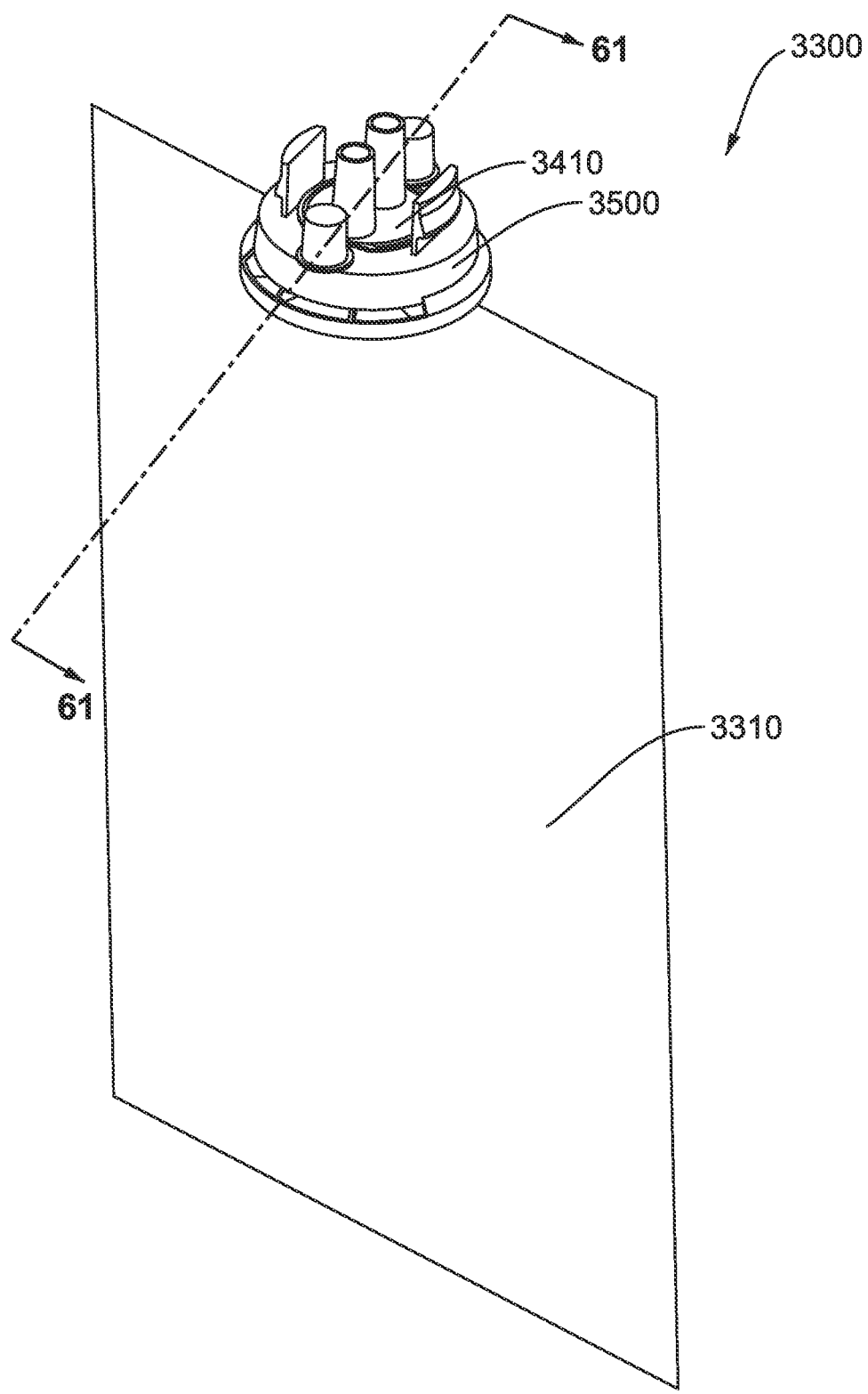
FIG. 60 is an isometric view of a liner assembly of the fluid collection system of FIG. 49, shown from above.
Figure 61:
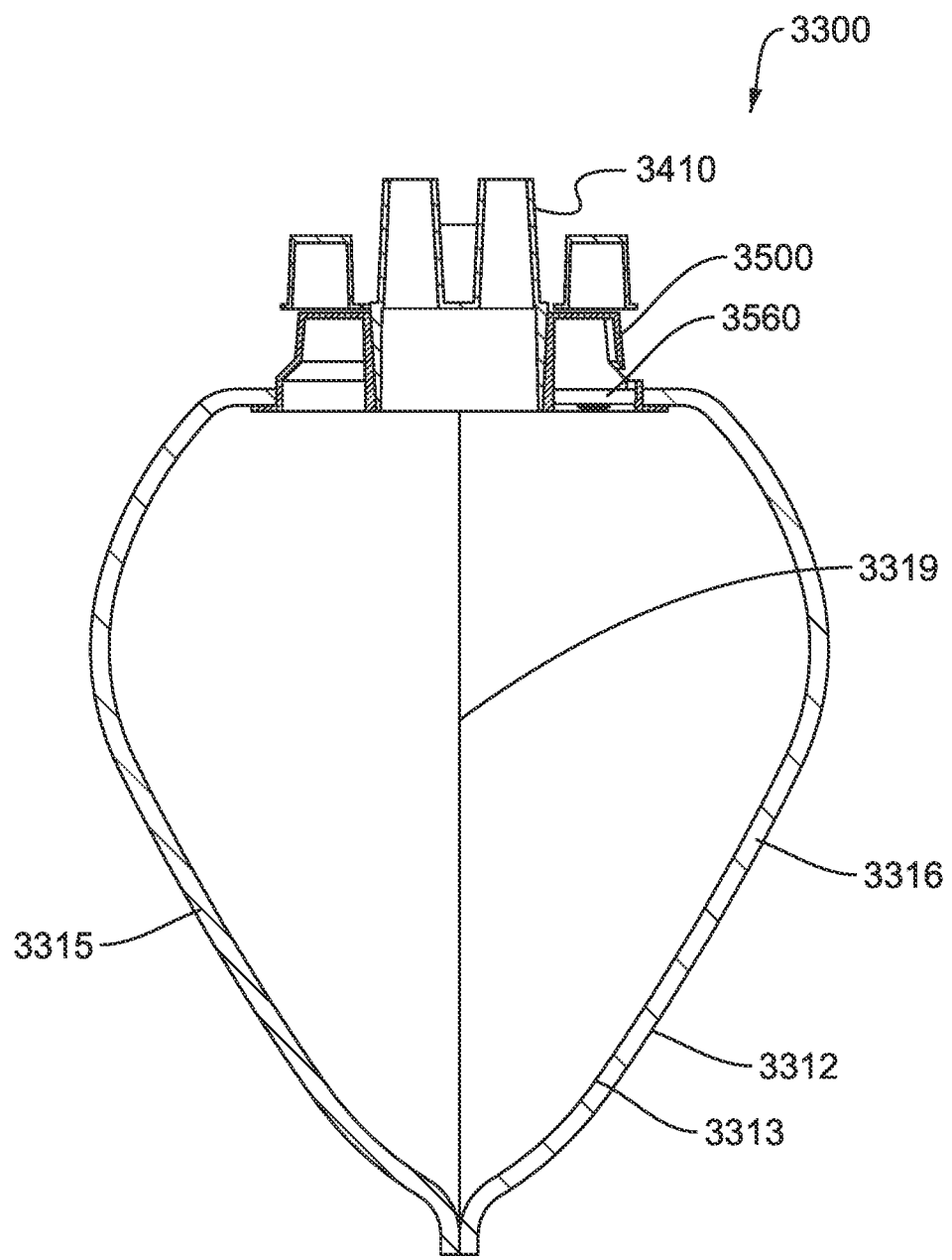
FIG. 61 is a cross-sectional view of the liner assembly of FIG. 60 taken along line 61, shown from the back.
Figure 65:
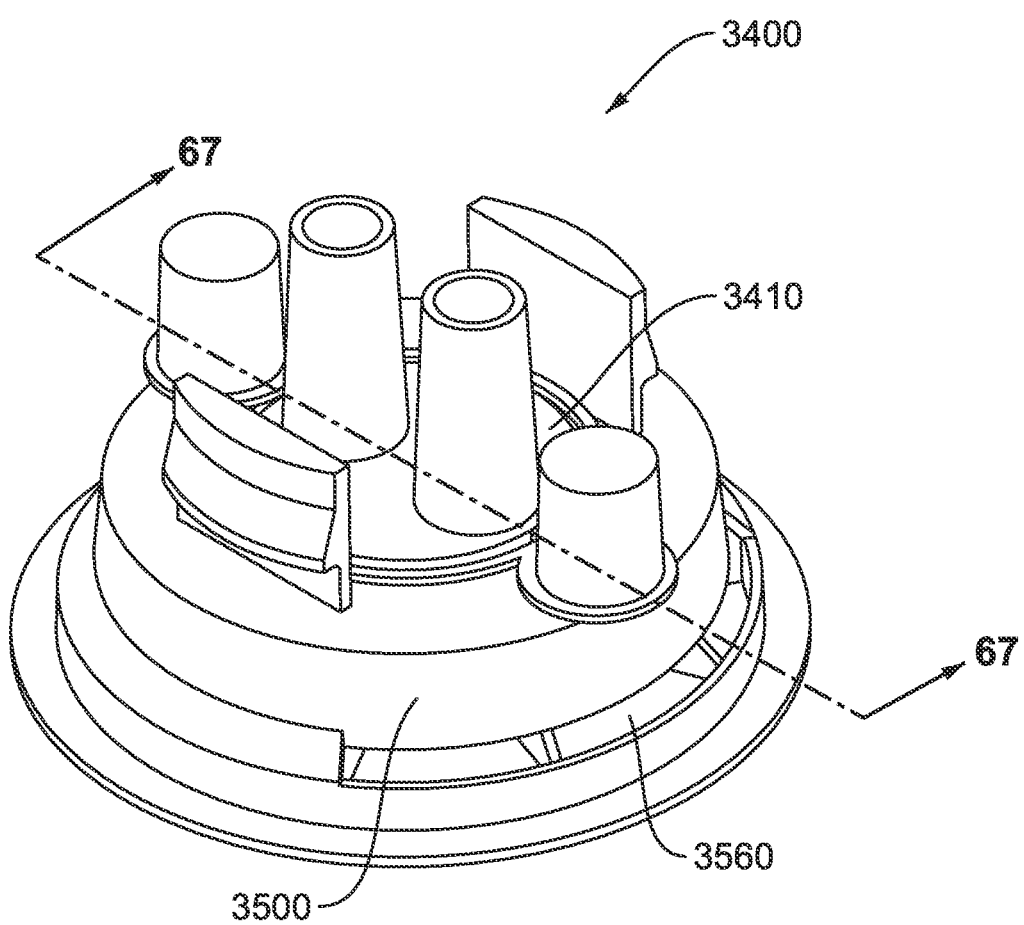
FIG. 65 is an isometric view of a fitment assembly of the fluid collection system of FIG. 49, shown from above.
Figure 66:
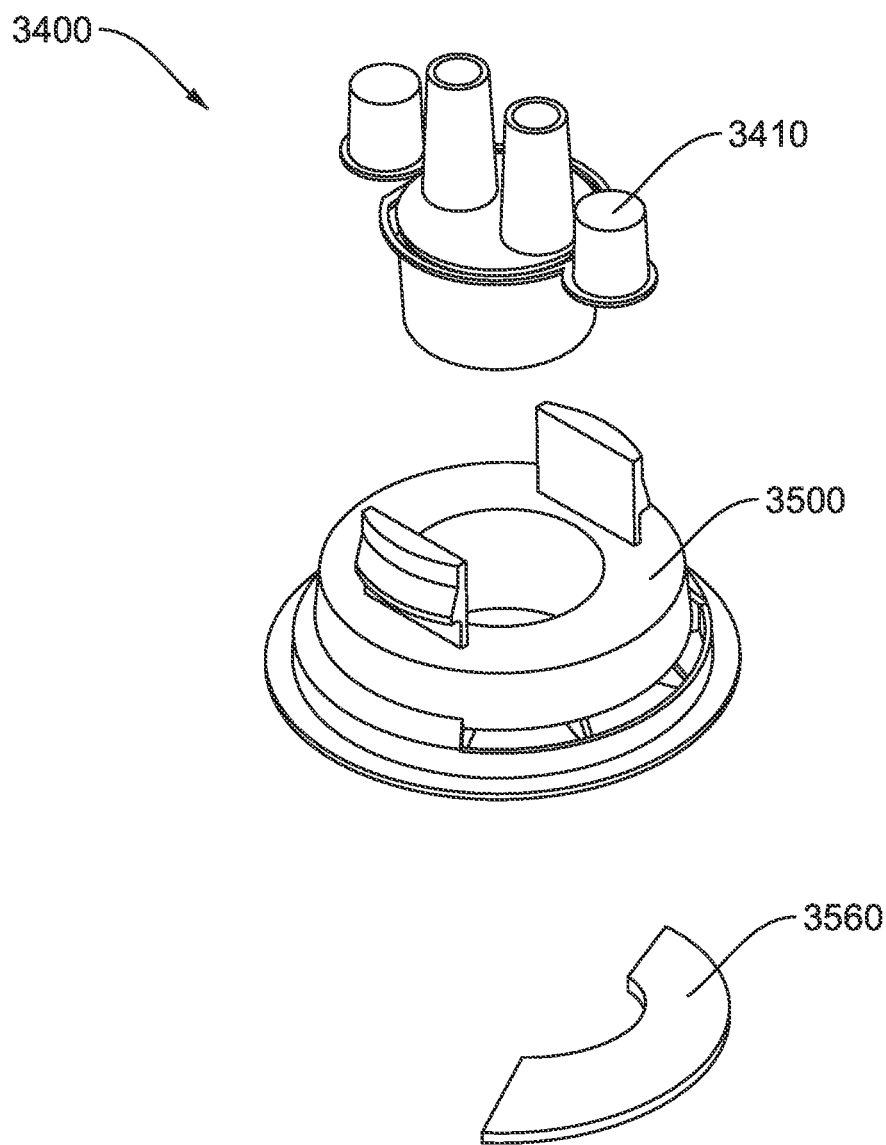
FIG. 66 is an exploded side view of the fitment assembly of FIG. 65.
Figure 67:
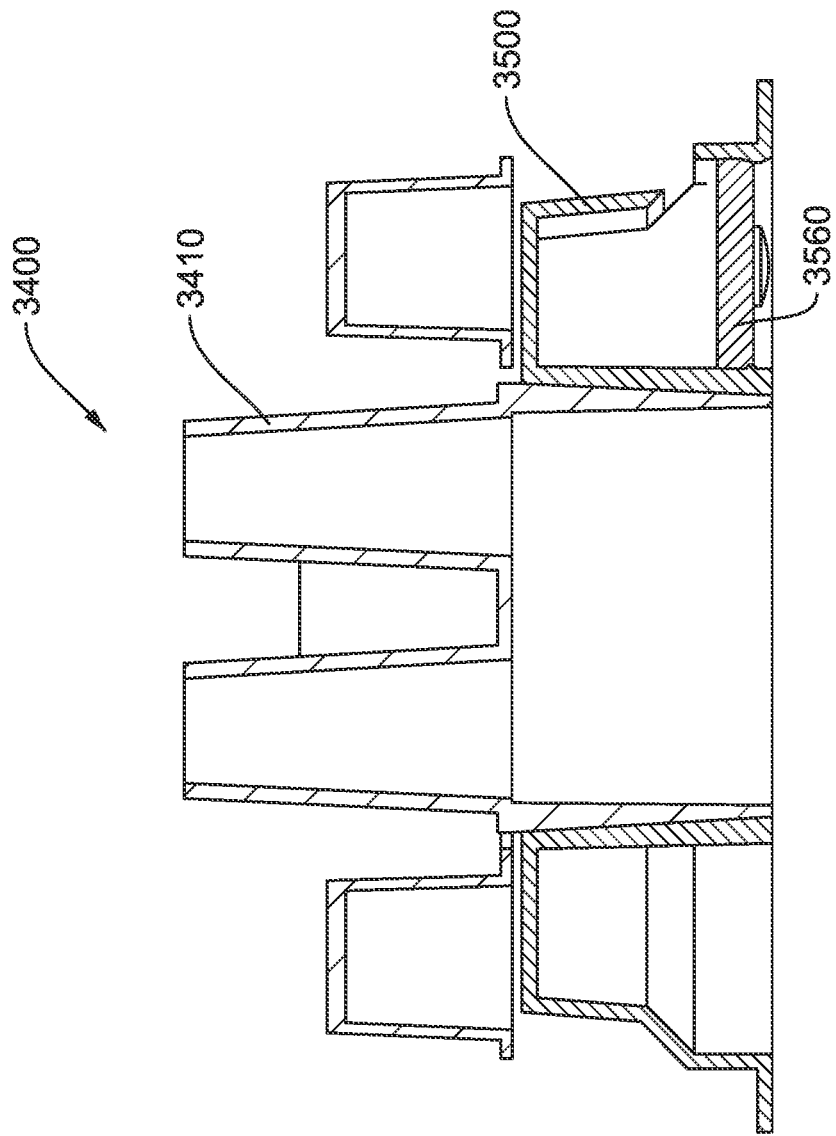
FIG. 67 is a cross-sectional view of the fitment assembly of FIG. 65 taken along line 67, shown from the side.

A third embodiment of the fluid collection system 3000 is shown in FIGS. 49-52 and may include a canister 3100, a lid 3200, a liner 3310 (not shown in FIG. 52), a fitment 3410, a gland 3500, a filter 3560, and two connectors 3630. Together, the fitment 3410, the gland 3500, and the filter 3560 form a fitment assembly 3400, as shown in FIGS. 65-67. Together, the fitment assembly 3400 and the liner 3310 form a liner assembly 3300, as shown in FIGS. 60-61. With respect to this embodiment, the terms "upper," "lower," "top," "bottom," "above," and "below" are discussed as shown in FIG. 50.

When the fluid collection system 3000 is in the closed position as shown in FIGS. 49-50, two chambers are formed: a fluid chamber 3002 and an interstitial chamber 3001. The fluid chamber 3002 may be substantially enclosed by the liner 3310 and the fitment assembly 3400. The interstitial chamber 3001 may be substantially enclosed by the canister 3100, the lid 3200, the liner 3310, and the fitment assembly 3400. A filter 3560 in the fitment assembly 3400 may separate the fluid chamber 3002 from the interstitial chamber 3001.

Figure 53:
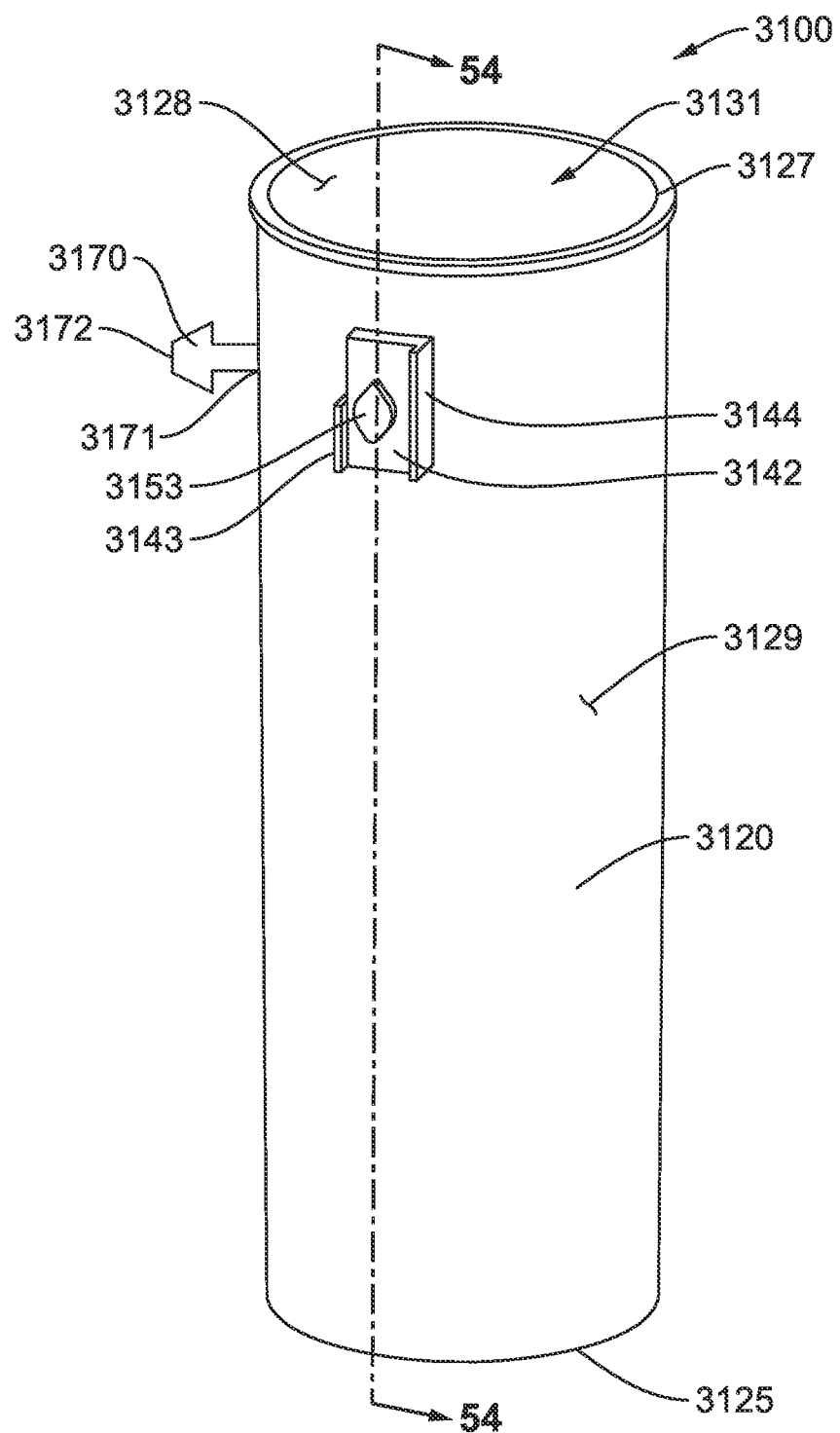
FIG. 53 is an isometric view of a canister of the fluid collection system of FIG. 49, shown from above.
Figure 54:
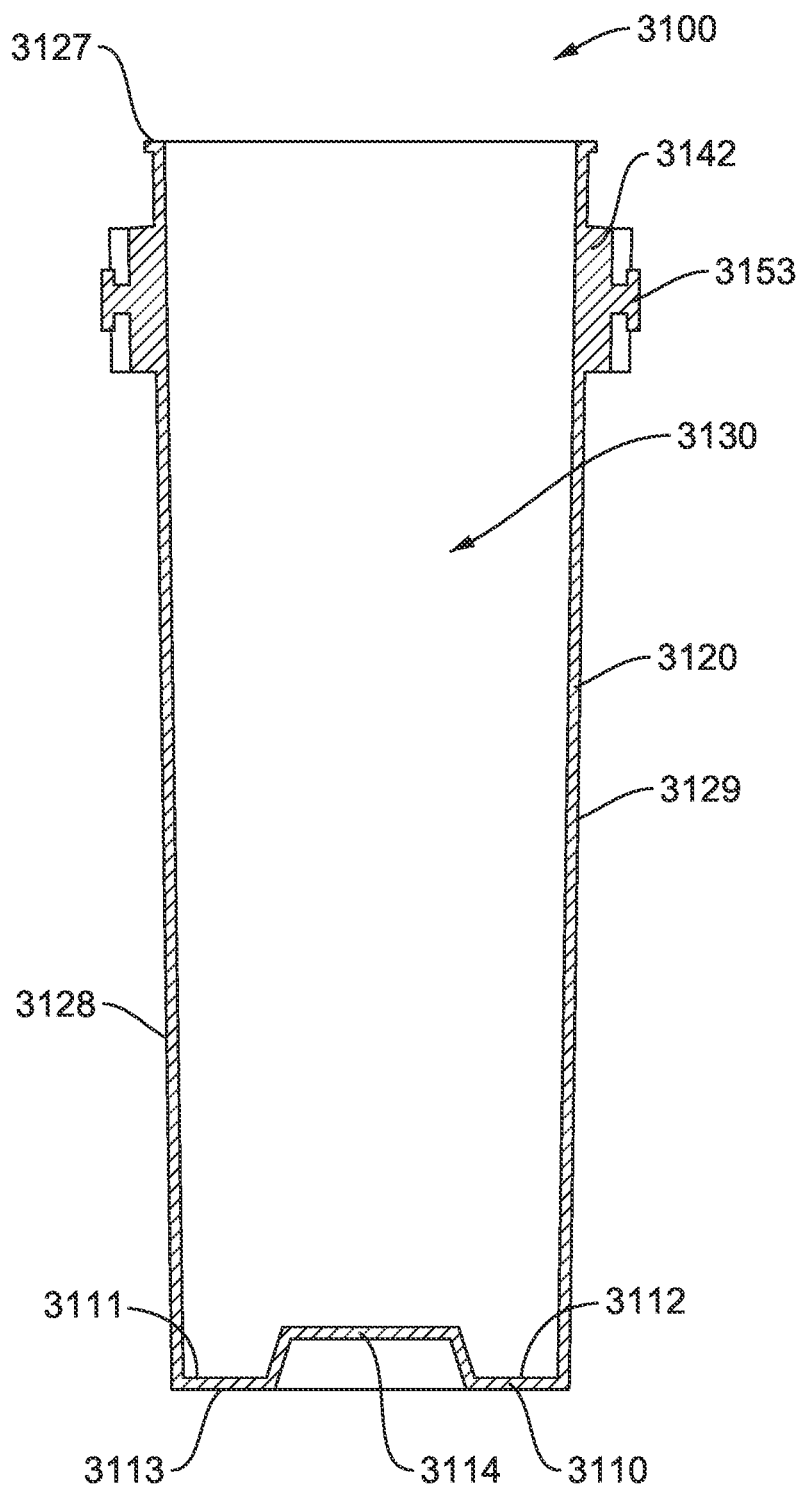
FIG. 54 is a cross-sectional view of the canister of FIG. 53 taken along line 54, shown from the side.

FIGS. 53-54 show the canister 3100 of the third embodiment, the canister 3100 having a bottom wall 3110 and a cylindrical side wall 3120. The bottom wall has an interior surface 3112, an exterior surface 3113, and an end 3111. The side wall 3120 has an interior surface 3128, an exterior surface 3129, a bottom end 3125, and a top end 3127. The bottom end 3125 of the side wall 3120 is connected to the end 3111 of the bottom wall 3110.

During use, the exterior surface 3113 of the bottom wall 3110 and the exterior surface 3129 of the side wall 3120 are exposed to the environment. The interior surface 3112 of the bottom wall 3110 and the interior surface 3128 of the side wall 3120 cooperate to form a cavity 3130. The cavity 3130 may have an open end such that the canister 3100 has an opening 3131 opposite the bottom wall 3110. The top end 3127 of the side wall 3120 may surround the opening 3131 of the cavity 3130, and may form the open end of the canister 3100. The opening 3131 may lie in the same plane as the top end 3127 of the side wall 3120. The bottom wall 3110 may have an indentation 3114 that extends from the interior surface 3112 of the bottom wall 3110 into the cavity 3130.

The canister 3100 may include an interstitial vacuum port 3170 having a vacuum source end 3172 that opens on the exterior of the canister 3100 and a cavity end 3171 that opens into the cavity 3130 of the canister 3100. In FIG. 53, the interstitial vacuum port 3170 is positioned on the side wall 3120 of the canister 3100. However, the interstitial vacuum port 3170 could also be positioned on the lid 3200.

Figure 55:
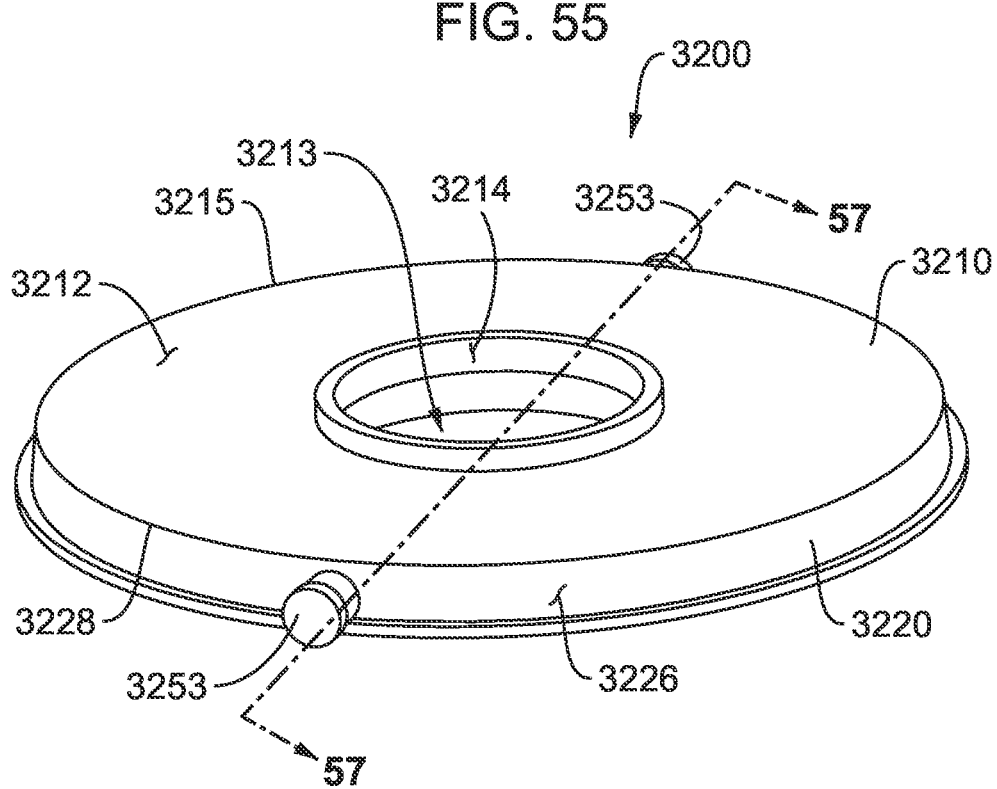
FIG. 55 is an isometric view of a lid of the fluid collection system of FIG. 49, shown from above.
Figure 56:
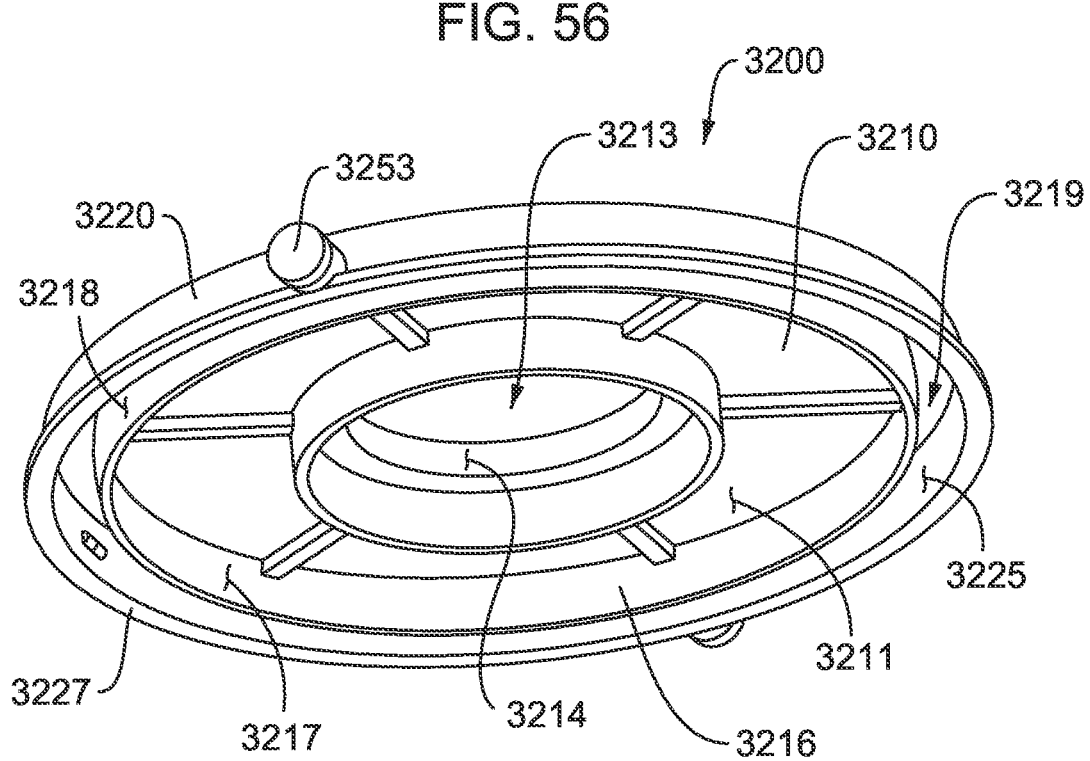
FIG. 56 is an isometric view of a lid of FIG. 55, shown from below.
Figure 57:
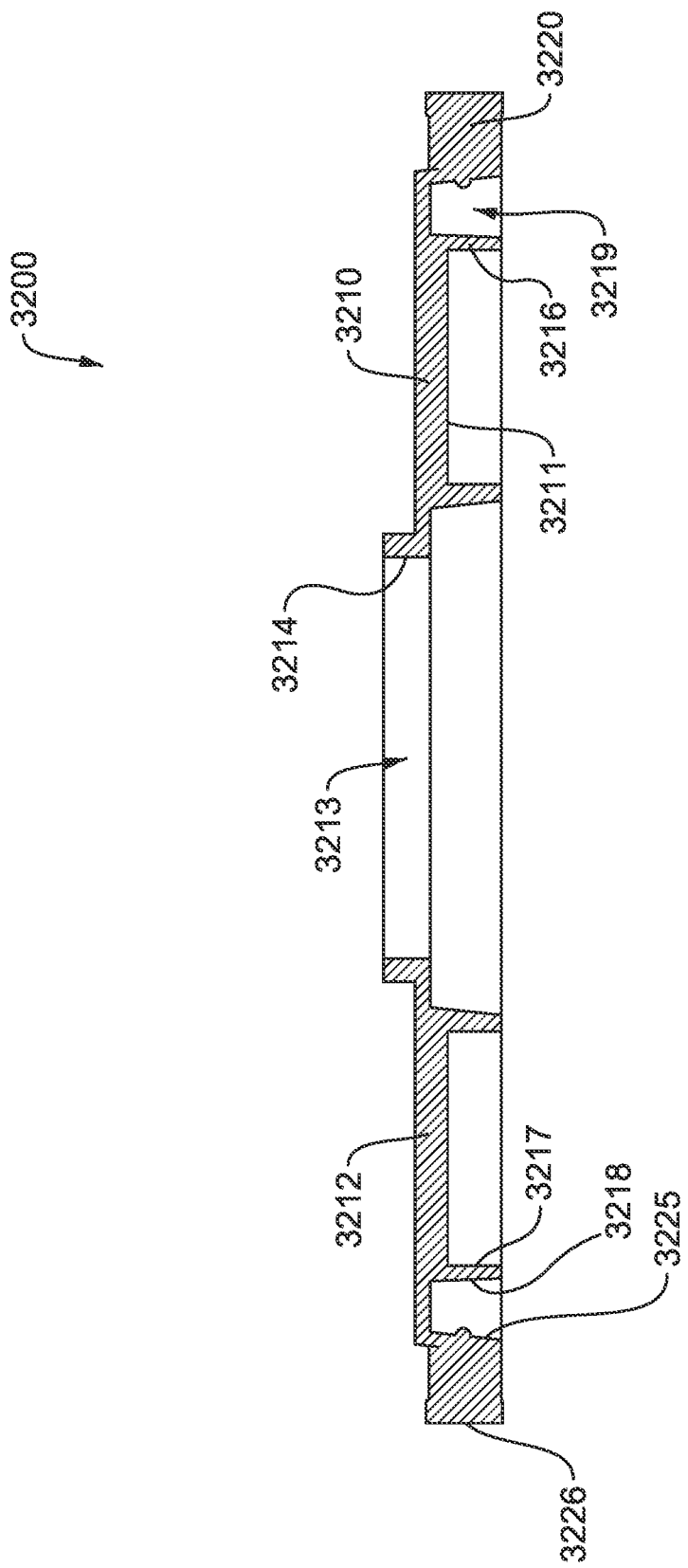
FIG. 57 is a cross-sectional view of the lid of FIG. 55 taken along line 57, shown from the side.

The fluid collection system 3000 also includes a lid 3200 as shown in FIGS. 55-57. The lid 3200 has an upper wall 3210 and a side wall 3220. The upper wall 3210 of the lid 3200 has an exterior surface 3212, an interior surface 3211, and an end 3215. The side wall 3220 has a bottom end 3227, a top end 3228, an interior surface 3225, and an exterior surface 3226. The bottom end 3227 of the side wall 3220 is connected to the end 3215 of the upper wall 3210. When the lid 3200 is in a closed position, the exterior surface 3212 of the upper wall 3210 is exposed to the environment and the interior surface 3211 of the upper wall 3210 faces the cavity 3130 of the canister 3100, as shown in FIGS. 49-50.

An opening 3213 is included in the upper wall 3210 of the lid 3200. The opening has an inner surface 3214. The lid 3200 may be placed over the opening 3131 of the cavity 3130 of the canister 3100 to partially close the opening 3131 of the cavity 3130. The opening 3213 in the upper wall 3210 of the lid 3200 enables communication into and out of the cavity 3130 of the canister 3100.

An annular rib 3216 extends from the interior surface 3211 of the upper wall 3210. The annular rib has an interior surface 3217 on the inner diameter of the rib 3216, and an exterior surface 3218 on the outer diameter of the rib 3216. The rib 3216 surrounds the opening 3213 in the lid 3200, and the side wall 3220 surrounds the rib 3216. The rib 3216, the side wall 3220, and the opening 3213 may be concentric circles. A groove 3219 is formed by the interior surface 3225 of the side wall 3220, the interior surface 3211 of the upper wall 3210, and the exterior surface 3218 of the rib 3216.

When the lid 3200 is in a closed position, the canister 3100 and the lid 3200 are in sealing engagement with one another. The top end 3127 of the side wall 3120 of the canister 3100 is inserted into the groove 3219 in the lid 3200. An interference fit may be formed between the exterior surface 3218 of the rib 3216 on the lid 3200 and the interior surface 3128 of the side wall 3120 of the canister 3100 to create sealing engagement between the canister 3100 and the lid 3200. Together, the groove 3219 on the lid 3200 and the top end 3127 of the side wall 3120 cooperate to enable sealing engagement between the canister 3100 and the lid 3200.

Figure 58:
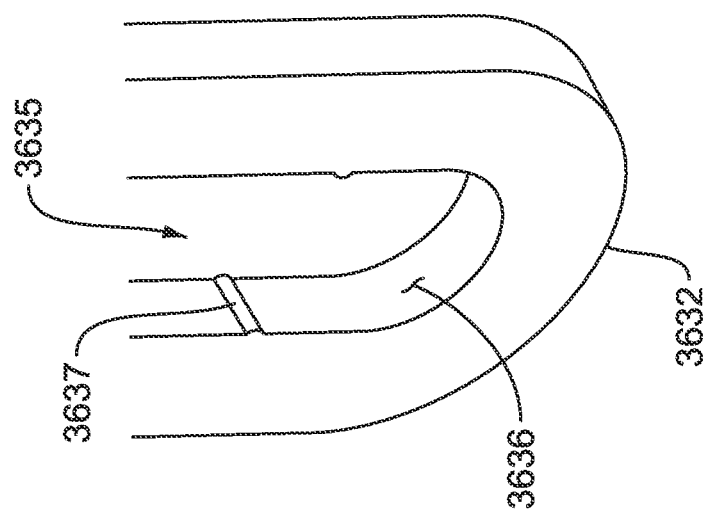
FIG. 58 is an isometric view of a connector of the fluid collection system of FIG. 49, shown from above.
Figure 59:
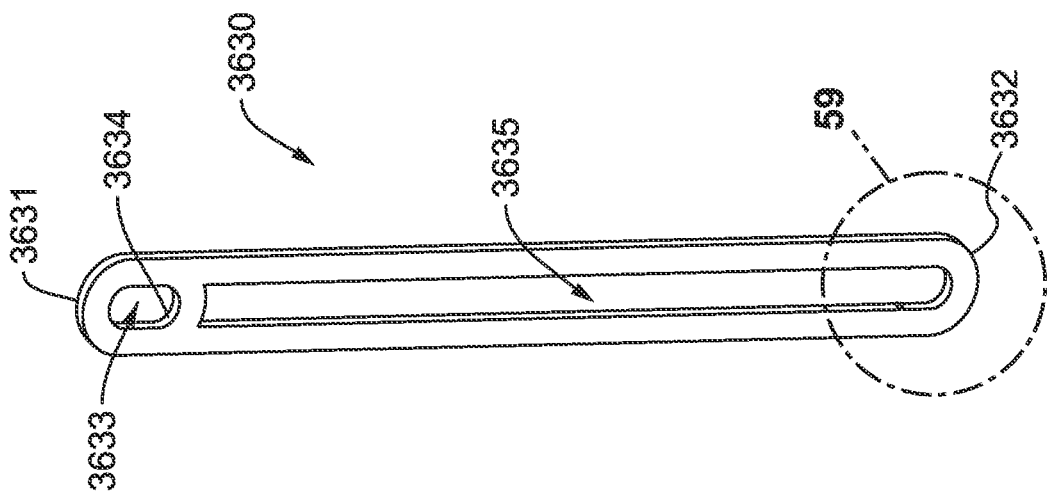
FIG. 59 is a detailed view of the connector of FIG. 58, shown from above.

Connectors 3630 shown in FIGS. 58-59 may optionally be used to couple the canister 3100 and the lid 3200. The connector 3630 is an elongated element extending from a first end 3631 to a second end 3632. A first opening 3633 may be located near the first end 3631, and a second opening 3635 may extend from an area near the second end 3632 toward the first end 3631 to form a track. The second opening 3635 may be substantially longer than the first opening 3633. The first opening 3633 may have an interior surface 3634, and the second opening 3635 may have an interior surface 3636. Two ribs 3637 may extend from the interior surface 3636 of the second opening 3635 of the connector 3630, near the second end 3632.

If connectors 3630 are used to couple the canister 3100 and the lid 3200, one or more pins 3153 may be included on the canister 3100, and one or more pins 3253 may also be included on the lid 3200. Two protrusions 3142 may be located on the exterior surface 3129 of the side wall 3120 of the canister 3100. The protrusions 3142 may be located on opposite sides of the canister 3100. A short rib 3143 and a long rib 3144 extend from the protrusion 3142 and oriented in a direction that is parallel to a line extending from the bottom end 3125 of the side wall 3120 toward the top end 3127 of the side wall 3120. The pin 3153 may be located between the short rib 3143 and the long rib 3144 on each protrusion 3142. Likewise, one or more pins 3253 may be located on the exterior surface 3226 of the side wall 3220 of the lid 3200. If connectors 3630 are not used to couple the canister 3100 and the lid 3200, the pins 3153, 3253, the protrusions 3142, and the ribs 3143, 3144, may be omitted.

If connectors 3630 are used to couple the canister 3100 and the lid 3200, each pin 3153 on the canister 3100 may be inserted into the second opening 3635 on one of the connectors 3630. Each pin 3253 on the lid 3200 may be inserted into the first opening 3633 on one of the connectors 3630. The pins 3153 on the canister 3100 are free to slide along the length of the second opening 3635. The pins 3253 in the lid 3200 are free to rotate within the first opening 3633.

Figure 52:
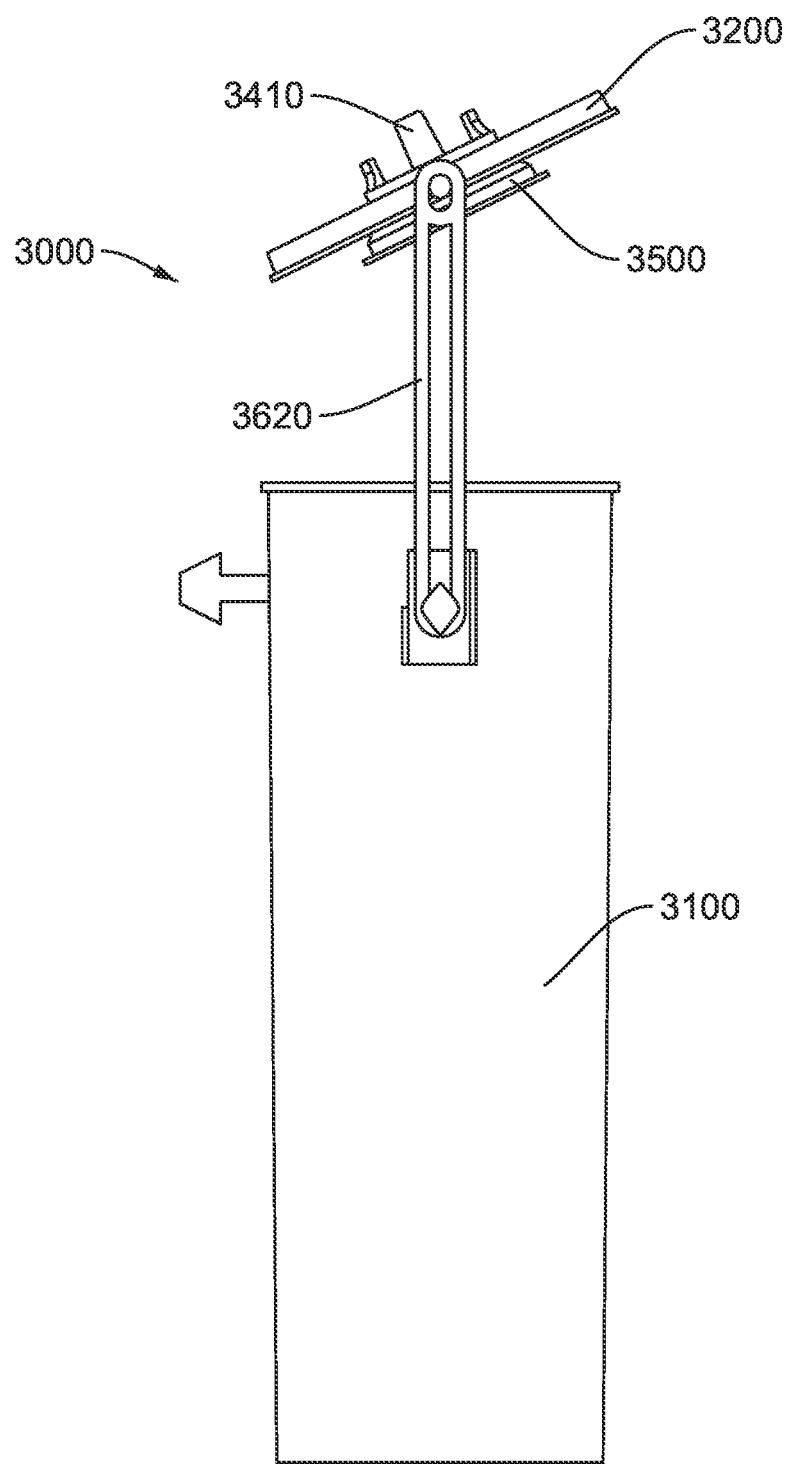
FIG. 52 is a side view of the fluid collection system of FIG. 49, shown in the open position. The liner is not shown in this figure.

The lid 3200 is moveable between a closed position shown in FIGS. 49-50 and an open position shown in FIG. 52. In the closed position, the lid 3200 and the canister 3100 are in sealing engagement with one another, and the lid 3200 partially closes the opening 3131 of the canister 3100. Together, the fitment assembly 3400 and the lid 3200 cooperate to substantially close the opening 3131 in the canister 3100. Moving the lid 3200 to the closed position may cause the pins 3153 on the canister 3100 to slide from the second end 3632 of the connector 3630 toward the first end 3631 of the connector 3630. In the open position, the lid 3200 and the canister 3100 are not in sealing engagement with one another, and the lid 3200 does not cover the opening 3131 of the canister 3100. Moving the lid 3200 to the open position may cause the pins 3153 on the canister 3100 to slide from the first end 3631 of the connector 3630 toward the second end 3632 of the connector 3630. The lid may be held in the open position by sliding the pins 3153 on the canister 3100 over the ribs 3637 in the second opening 3635 of the connector 3630.

The fluid collection system 3000 also includes a liner assembly 3300 as shown in FIGS. 60-61. The liner assembly 3300 (i.e. fluid receptacle) includes a liner 3310 and a fitment assembly 3400 which cooperate to substantially enclose a fluid chamber 3002.

Figure 62:
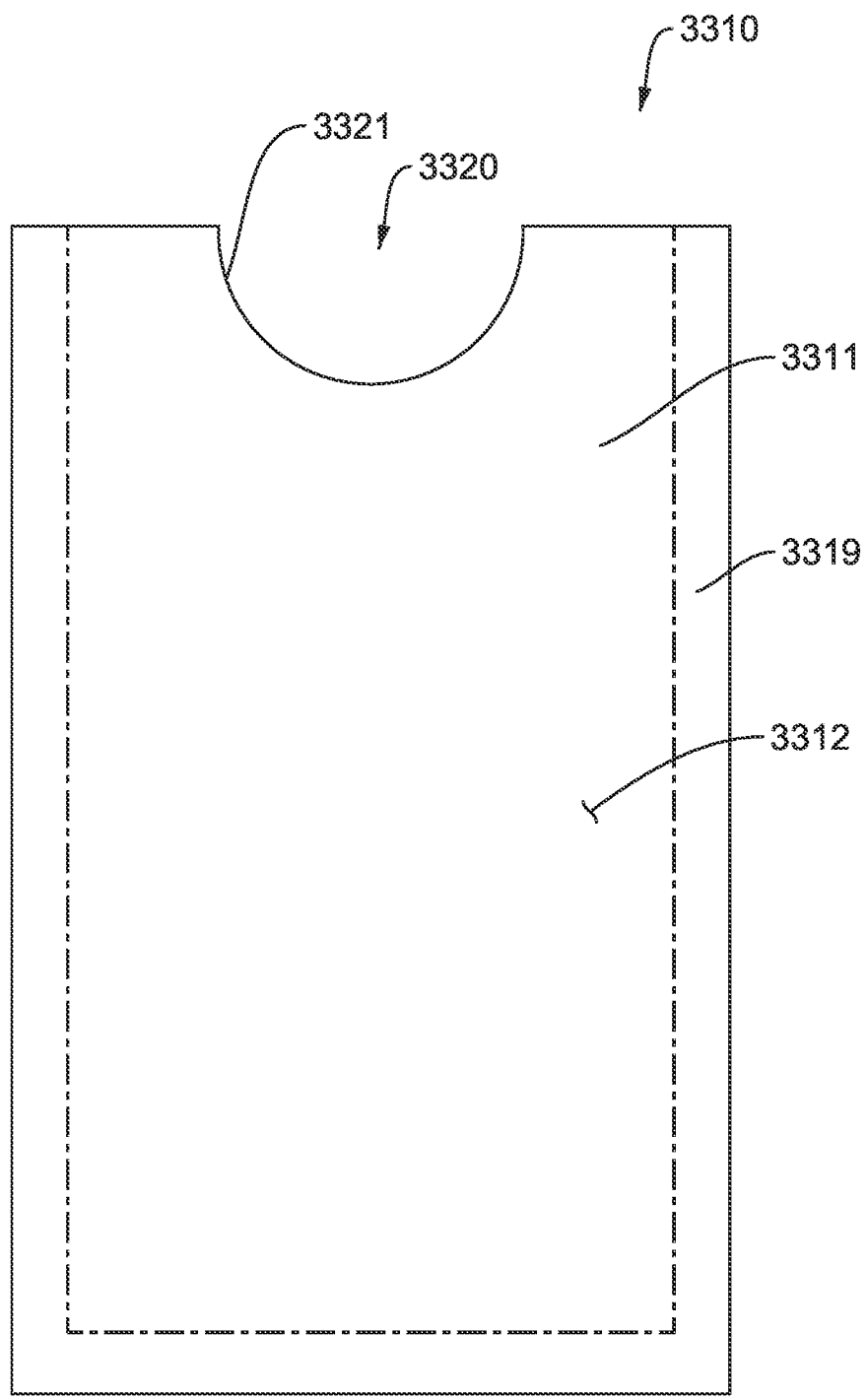
FIG. 62 is a side view of the liner of the liner assembly of FIG. 60.

The liner 3310 of the third embodiment is shown in FIG. 62. FIG. 63 shows the body 3311 of the liner 3310 before the liner 3310 is assembled. The body 3311 of the liner 3310 is made of a thin-walled material. The body 3311 has been folded along a fold line 3314 to create a first panel 3315 having four ends and a second panel 3316 having four ends. The first panel 3315 and the second panel 3316 are joined along one end by the fold, as shown in FIG. 64. The remaining three ends of the first panel 3315 form a first periphery 3317, and the remaining three ends of the second panel 3316 form a second periphery 3318. The first panel 3315 and the second panel 3316 are joined to one another by a seal 3319 extending along the first periphery 3317 and the second periphery 3318 as shown in FIG. 62. The seal 3319 extends from the dashed line in FIG. 62 toward the first periphery 3317 and the second periphery 3318 of the liner 3310. The seal may be about ⅜" wide, or may have a different width as long as an appropriate seal strength is maintained when the liner 3310 is exposed to vacuum and/or contains fluid.

The liner 3310 of the third embodiment has an opening 3320 in the body 3311 of the liner 3310, such that the fold line 3314 passes through the opening 3320. The opening 3320 in the body 3311 of the liner 3310 may be substantially circular, or could be any number of other shapes. The body 3311 has a third periphery 3321 at the edge of the opening 3320. The gland 3500, described below, is configured to be inserted into the opening 3320 in the body 3311 of the liner 3310.

As shown in FIG. 50, the liner 3310 is positioned in the cavity 3130 of the canister 3100. The liner 3310 has a canister-facing surface 3312 and a fluid chamber surface 3313, as shown in FIG. 64. When the liner assembly 3300 is ready for use, the liner 3310 is oriented such that the canister-facing surface 3312 is on the outside (and may be facing the interior surface 3112 of the bottom wall 3110 and the interior surface 3128 of the side wall 3120 when inserted into the canister 3100) and the fluid chamber surface 3313 is on the inside.

The fitment assembly 3400 of the third embodiment is shown in FIGS. 65-67. The fitment assembly 3400 includes a fitment 3410, a gland 3500, and a filter 3560. The fitment assembly 3400 also includes two fluid ports 3450 and a fluid chamber vacuum port 3540. The fluid ports 3450 may be located on the fitment 3410, and the fluid chamber vacuum port 3540 may be located on the gland 3500.

Figure 68:
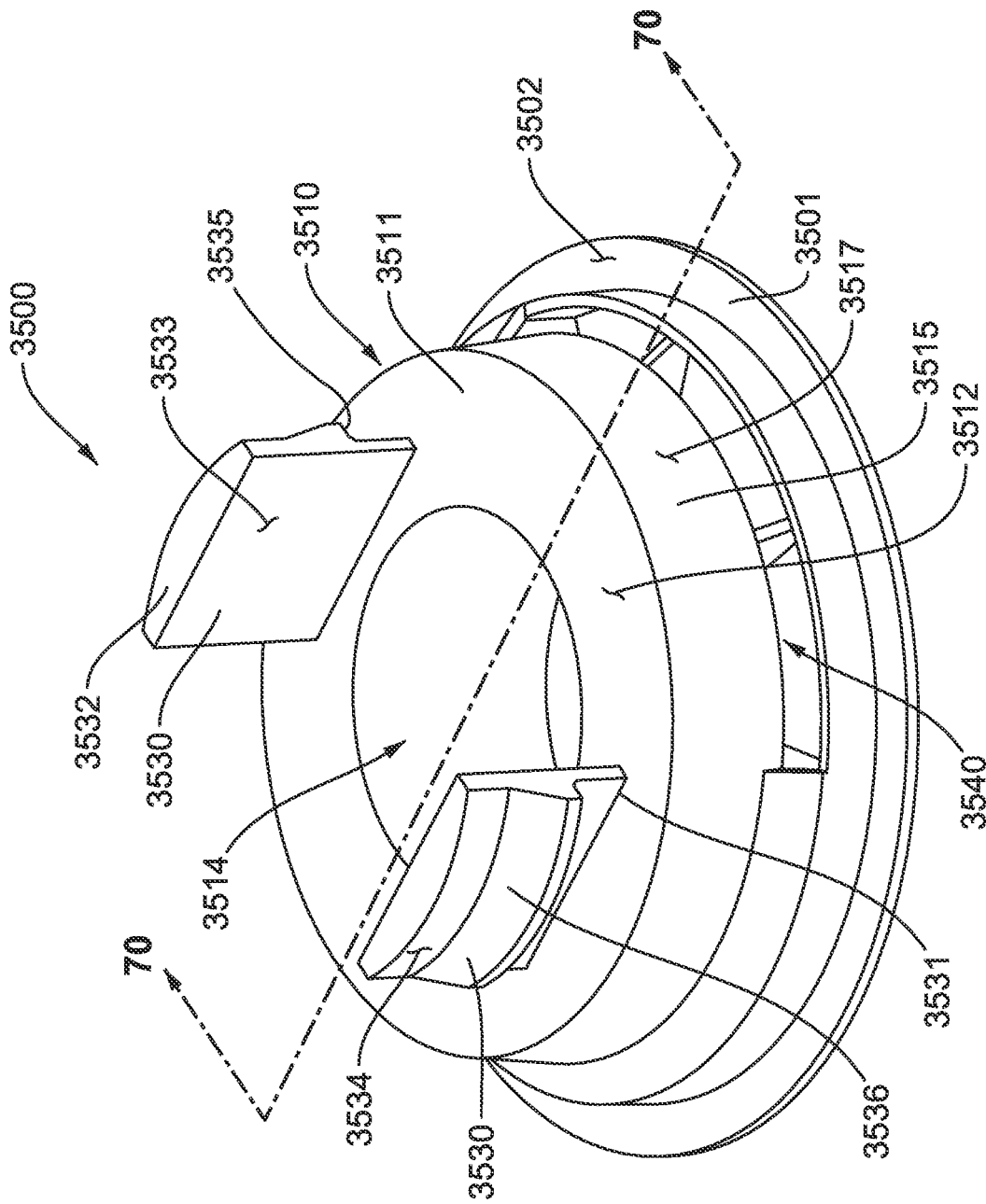
FIG. 68 is an isometric view of a gland of the fitment assembly of FIG. 65, shown from the top.
Figure 69:
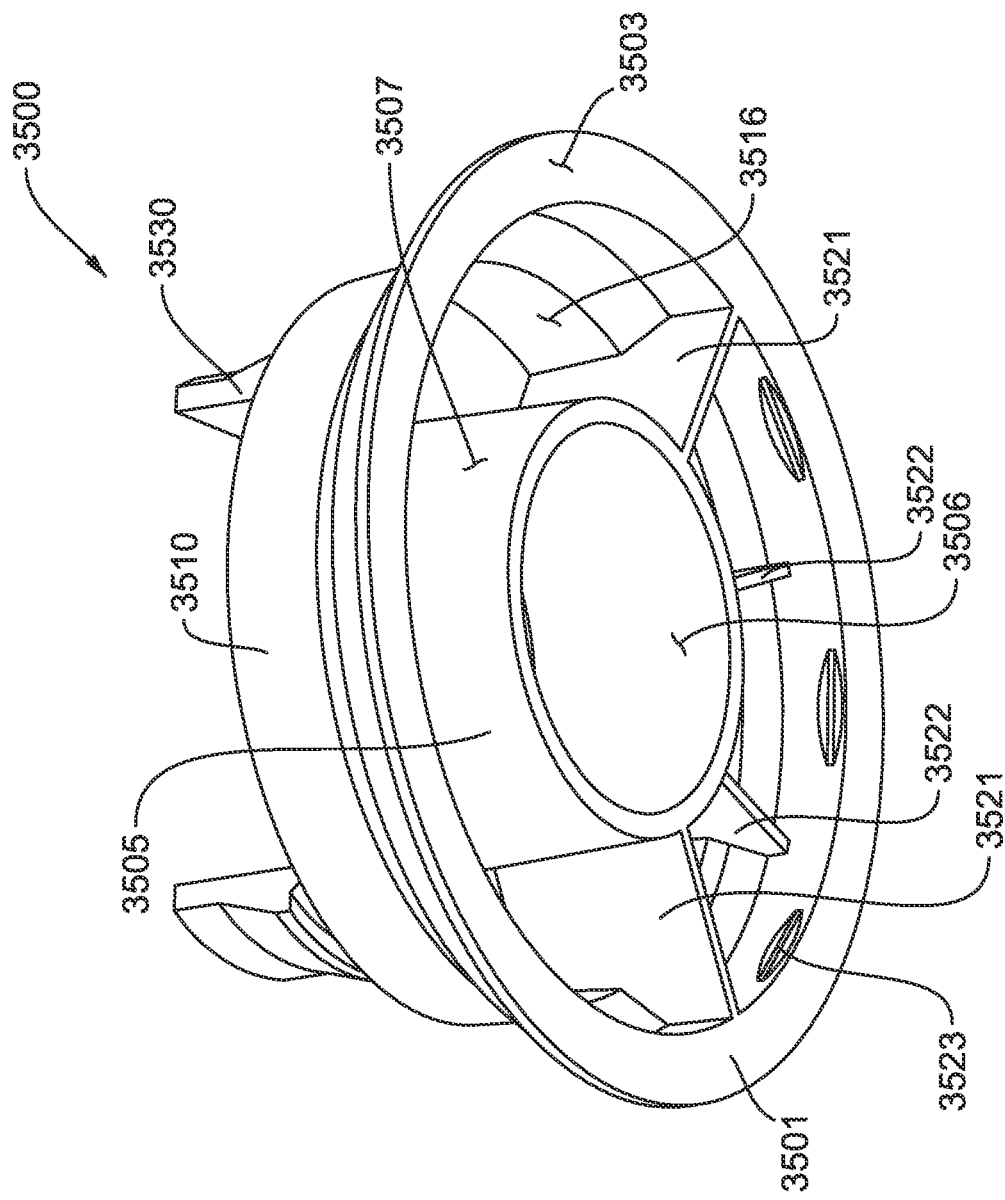
FIG. 69 is an isometric view of the gland of FIG. 68, shown from below.
Figure 70:
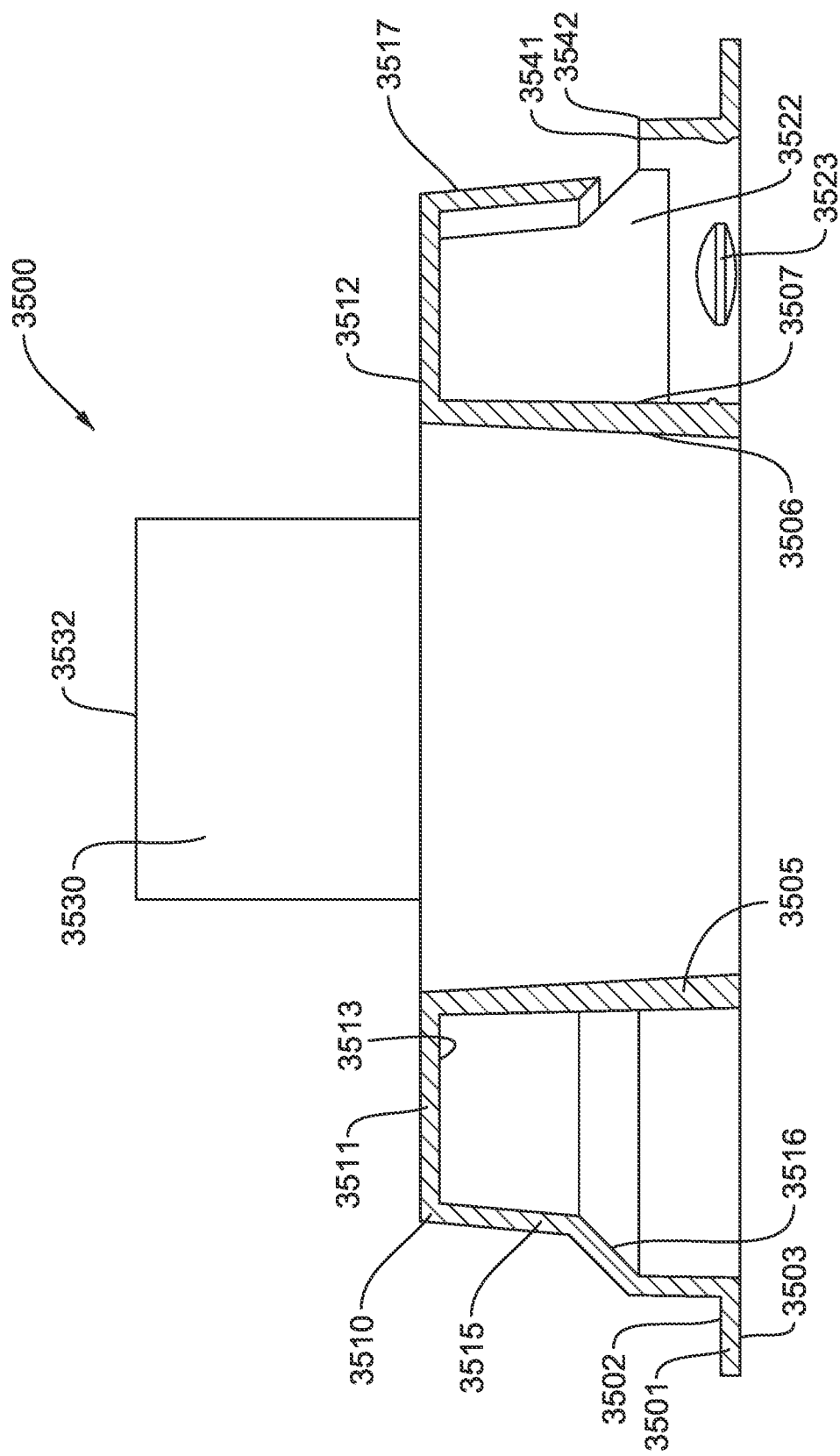
FIG. 70 is a cross-sectional view of the gland of FIG. 68, taken along line 70, shown from the side.

The gland 3500 is shown in FIGS. 68-70. The gland 3500 has a base 3501 shaped like a disc. The base 3501 has a first surface 3502 and a second surface 3503. A protrusion 3510 extends from the first surface 3502 of the base 3501. The protrusion 3510 has an upper wall 3511 with an upper surface 3512 and a lower surface 3513, and a side wall 3515 with an interior surface 3516 and an exterior surface 3517. The side wall 3515 of the protrusion 3510 is shown as having a series of steps, but could also be one continuous wall extending from the base 3501 to the upper wall 3511 of the protrusion 3510.

An opening 3514 extends between the upper surface 3512 and the lower surface 3513 of the upper wall 3511 of the gland 3500. A rib 3505 extends from the lower surface 3513 of the upper wall 3511 and surrounds the opening 3514. The rib 3505 has an inner surface 3506 on the inner diameter of the rib 3505, and an outer surface 3507 on the outer diameter of the rib 3505.

In the third embodiment, the gland 3500 includes the fluid chamber vacuum port 3540 which may allow a vacuum in the interstitial chamber 3001 to be transmitted to the fluid chamber 3002. The fluid chamber vacuum port 3540 is an opening in the side wall 3515 of the protrusion 3510 of the gland 3500 that may allow gas to move between the fluid chamber 3002 and the interstitial chamber 3001. The fluid chamber vacuum port 3540 has a fluid chamber end 3541 on an interior surface 3516 of the side wall 3515, and an interstitial chamber end 3542 on an exterior surface 3517 of the side wall 3515.

The gland 3500 may also include a filter guard that protects the filter 3560 from accidental splashing, as discussed with the first embodiment. In addition, the filter guard of the third embodiment also holds the filter 3560 in place within the gland 3500. The filter guard is formed by a portion of the side wall 3515 of the protrusion 3510, a portion of the rib 3505, and two filter sealing ribs 3521. The filter sealing ribs 3521 and extend between the side wall 3515 of the protrusion 3510 and the rib 3505, and extend from the lower surface 3513 of the upper wall 3511 of the protrusion 3510 toward the base 3501 of the gland 3500.

The filter guard includes features to hold the filter 3560 in place. Filter support ribs 3522 are positioned within the filter guard. The filter support ribs 3522, like the filter sealing ribs 3521, extend between the side wall 3515 of the protrusion 3510 and the rib 3505, and extend from the lower surface 3513 of the upper wall 3511 of the protrusion 3510 toward the base 3501 of the gland 3500. However, the filter sealing ribs 3521 extend closer to the base 3501 of the gland 3500 than the filter support ribs 3522 do. Filter retaining ribs 3523 are positioned on the interior surface 3516 of the side wall 3515 near the base 3501.

The filter sealing ribs 3521 may extend from the from the lower surface 3513 of the upper wall 3511 of the protrusion 3510 to the filter retaining ribs 3523, or may even extend beyond the filter retaining ribs 3523. The filter support ribs 3522 may extend from the lower surface 3513 of the upper wall 3511 of the protrusion 3510, although they may not extend to the filter retaining ribs 3523. One filter sealing rib 3521 may be on one side of the fluid chamber vacuum port 3540, and another filter sealing rib 3521 may be at the opposite side of the fluid chamber vacuum port 3540. The fluid chamber end 3541 of the fluid chamber vacuum port 3540 is contained within the filter guard. The filter 3560 is positioned below the fluid ports 3450 on the fitment 3410 which eliminates the need for a fluid port check valve for the same reasons discussed in the first embodiment.

Two or more latches 3530 extend from the upper surface 3512 of the upper wall 3511 of the protrusion 3510. Two latches 3530 are shown in FIG. 68, but any number of latches may be used. Each latch 3530 has a lower end 3531, an upper end 3532, an inner surface 3533 and an outer surface 3534. The lower end 3531 of each latch 3530 is connected to the upper wall 3511 of the protrusion 3510. The inner surface 3533 of each latch 3530 faces the opening 3514, and the outer surface 3534 of each latch 3530 faces away from the opening 3514. Each latch 3530 has a ramp 3536 extending from the upper end 3532 of the latch 3530 toward the lower end 3531. A ledge 3535 is positioned at the bottom of the ramp 3536, the ledge 3535 being substantially parallel to the upper wall 3511 of the protrusion 3510. Latches also may be included on the lid in place of, or in addition to, the latches 3530 on the fitment assembly 3400.

The vacuum source 3700 is connected to the interstitial chamber 3001, resulting in a reduced pressure in the interstitial chamber 3001. The reduced pressure in the interstitial chamber 3001 may cause air from the fluid chamber 3002 to pass through the fluid chamber vacuum port 3540 and into the interstitial chamber 3001, thereby creating a vacuum in the fluid chamber 3002. In this pass-through configuration, the fluid chamber 3002 is upstream of the interstitial chamber 3001. The pass-through configuration may be preferred to other configurations where the fluid chamber vacuum port 3540 is independently connected to the vacuum source 3700 because the user does not need to connect a vacuum tube to the fluid chamber 3002 during each procedure. However, either configuration of fluid chamber vacuum ports 3540 may be used.

A filter 3560 shown in FIG. 66 is coupled to the fluid chamber vacuum port 3540. Similar to the filter of the first embodiment, the filter 3560 of the third embodiment has two purposes: removing bacteria, particulates and other solid matter from air flowing toward the vacuum source 3700, and acting as a vacuum shut-off. The materials used to make the filter in the first embodiment may also be used for the filter of the third embodiment. However, the filter 3560 of the third embodiment is arc shaped, and substantially planar having two opposing surfaces: an upstream surface 3561 and a downstream surface 3562.

The filter 3560 is inserted into the filter guard of the gland 3500. The downstream surface 3562 of the filter 3560 may be in communication with the interstitial chamber 3001 and the vacuum source 3700, and rests on the filter support ribs 3522 within the filter guard. The upstream surface 3561 of the filter 3560 is in communication with the fluid chamber 3002 and is held in place by the filter retaining ribs 3523. The periphery of the filter 3560 is in sealing engagement with the side wall 3515 of the protrusion 3510, the rib 3505, and the filter sealing ribs 3521. During use, air may move through the filter 3560 in a downstream direction, from the fluid chamber 3002, through the filter 3560, and toward the fluid chamber vacuum port 3540, the interstitial chamber 3001, and the vacuum source 3700.

The gland 3500 and the liner 3310 are in sealing engagement with one another. The gland 3500 and the liner 3310 are coupled by inserting the protrusion 3510 of the gland 3500 into the opening 3320 in the body 3311 of the liner 3310. The first surface 3502 of the base 3501 of the gland 3500 is in sealing engagement with the fluid chamber surface 3313 of the liner 3310 at the third periphery 3321 surrounding the opening 3320 of the liner 3310.

Figure 71:
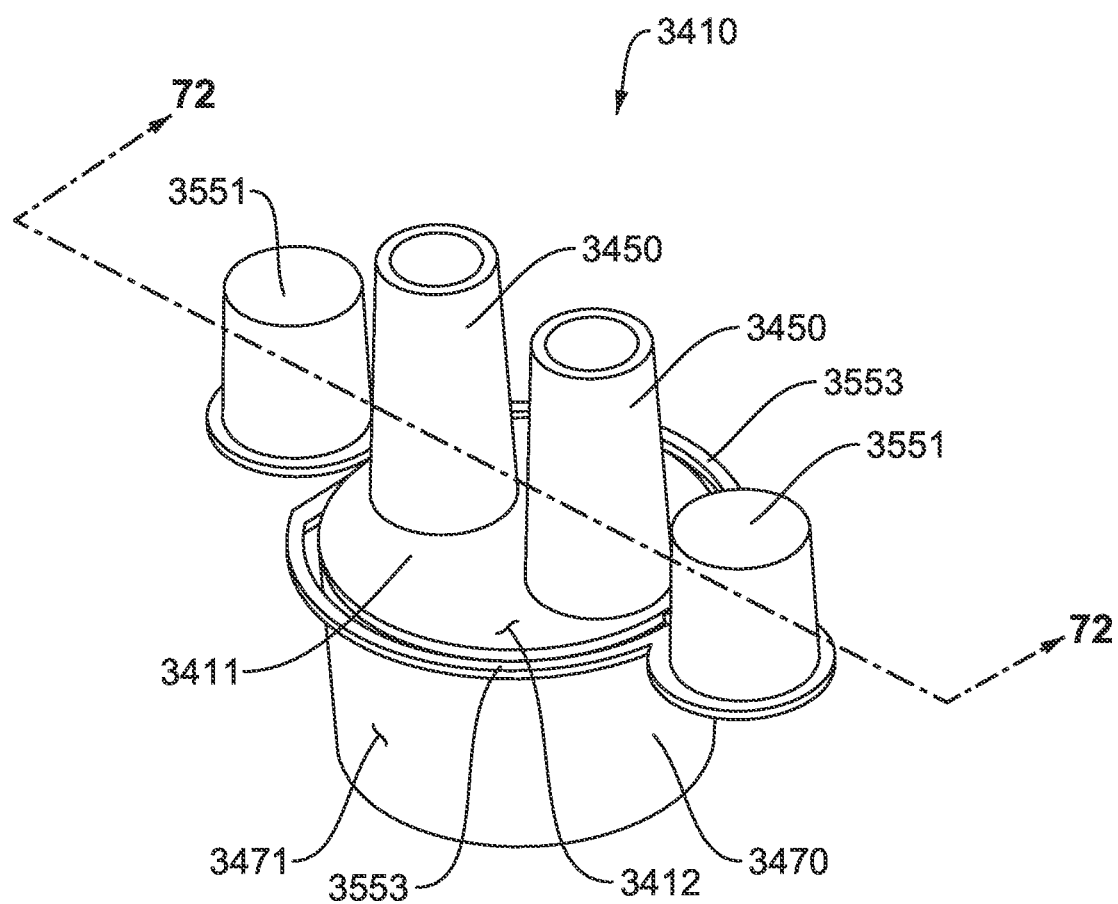
FIG. 71 is an isometric view of a fitment of the fitment assembly of FIG. 65, shown from above.
Figure 72:
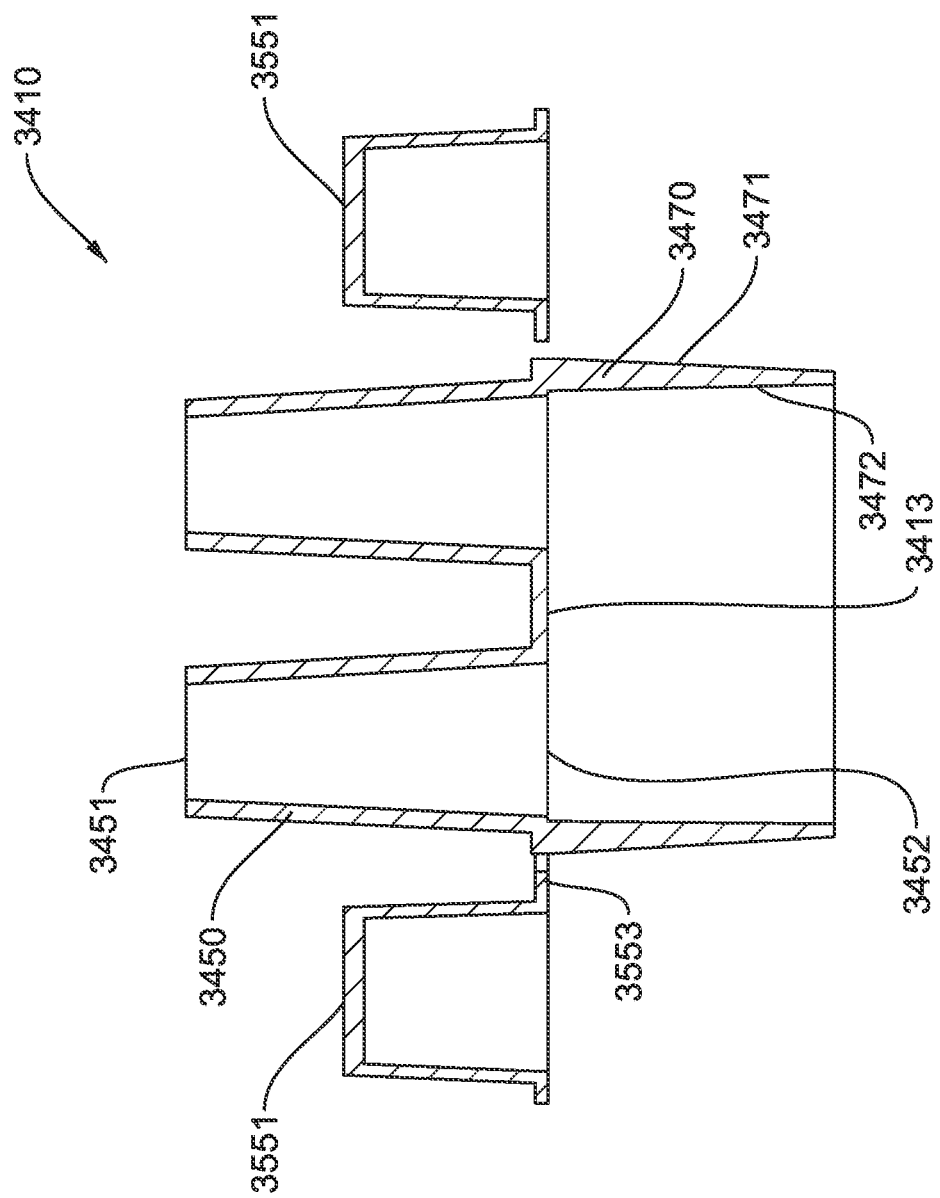
FIG. 72 is a cross-sectional view of the fitment of FIG. 71 taken along line 72, shown from the side.

The fitment 3410 is shown in FIGS. 71-72. The fitment has a base 3411 having an upper surface 3412 and a lower surface 3413. When the fitment 3410 is positioned as shown in FIG. 50, the lower surface 3413 of the fitment 3410 faces the bottom wall 3110 of the canister 3100, and the upper surface 3412 of the fitment 3410 is exposed to the environment.

A first rib 3470 protrudes from the lower surface 3413 of the base 3411 of the fitment 3410 and surrounds at least a portion of the lower surface 3413 of the base 3411. The first rib 3470 has an inner surface 3472 and an outer surface 3471.

The fitment 3410 includes a fluid port 3450 that allows fluid to enter the fluid chamber 3002. The fluid port 3450 is an opening that extends from the upper surface 3412 of the base 3411 to the lower surface 3413 of the base 3411. The patient end 3451 of the fluid port 3450 protrudes from the upper surface 3412 of the base 3411, such that a patient tube may be connected to the patient end 3451 of the fluid port 3450. A fluid chamber end 3452 of the fluid port 3450 opens proximate the lower surface 3413 of the base 3411. The fluid chamber end 3452 of the fluid port 3450 may be an opening in the base 3411, or it may protrude from the lower surface 3413 of the base 3411. Fluid flows from the patient tube and through the fluid port 3450 on the fitment 3410 before entering the fluid chamber 3002.

As discussed in the first embodiment, the third embodiment may optionally include a fluid port check valve (not shown) coupled to the fluid port 3450 to allow one-directional flow of fluid through the fluid port 3450.

The fitment 3410 and the gland 3500 are coupled by mating the rib 3470 of the fitment 3410 with the rib 3505 of the gland 3500, such that the inner surface 3506 of the rib 3505 of the gland 3500 may have an interference fit with the outer surface 3471 of the first rib 3470 of the fitment 3410.

When moving the fluid collection system 3000 to the closed position, the latches 3530 on the gland 3500 are inserted into the opening 3213 in the lid 3200. The ledge 3535 of each latch 3530 rests on the exterior surface 3212 of the upper wall 3210 of the lid 3200, thereby connecting the fitment assembly 3400 to the lid 3200. An interference fit between the inner surface 3214 of the opening 3213 of the lid 3200 and the exterior surface 3517 of the side wall 3515 of the protrusion 3510 on the gland 3500 may create sealing engagement between the lid 3200 and the gland 3500. Therefore, the fitment assembly 3400 may have a sealing surface that seals to the lid 3200. In some embodiments, the exterior surface 3517 of the side wall 3515 of the protrusion 3510 on the gland 3500 may form the sealing surface of the fitment assembly 3400 that allows the fitment assembly 3400 to seal to the lid 3200.

The canister 3100, the lid 3200 and the gland 3500 of the fitment assembly 3400 are in sealing engagement when the fluid collection system 3000 is in the closed position. As discussed above, the lid 3200 is sealingly engaged with the canister 3100. The gland 3500 of the fitment assembly 3400 is sealingly engaged with the lid 3200. Together, the fitment assembly 3400 and the lid 3200 cooperate to substantially close the opening 3131 in the canister 3100.

For the same reasons discussed in the first embodiment, any unused fluid ports in the third embodiment should be capped during the procedure. In the third embodiment, the fluid port caps 3551 are connected to or integrally molded with the fitment 3410. Each fluid port cap 3551 is connected to the base 3411 of the fitment 3410 by a bridge 3553.

An interstitial chamber 3001 is formed when the fluid collection system 3000 is in the closed position, as shown in 50. The interstitial chamber 3001 is the space substantially enclosed by the canister 3100, the liner 3310, the lid 3200 and the fitment assembly 3400. In order to enable the interstitial chamber 3001 to maintain vacuum pressure, the canister 3100 may be in sealing engagement with the lid 3200, the lid 3200 may be in sealing engagement with the gland 3500, and the gland 3500 may be in sealing engagement with the liner 3310. Preferably, the liner 3310 may be sealingly engaged with the gland 3500 during the manufacturing process. If the fluid chamber vacuum port 3540 uses a pass-through design, the filter 3560 may also be in sealing engagement with the gland 3500 to substantially enclose the interstitial chamber 3001, and the filter 3560 may separate the interstitial chamber 3001 and the fluid chamber 3002.

When a vacuum is applied to the interstitial chamber 3001, the liner 3310 expands in the cavity 3130 of the canister 3100. The canister-facing surface 3312 of the liner 3310 may at least partially conform to the bottom wall 3110 and the side walls 3121, 3122, 3123, 3124 of the canister 3100. A vacuum source 3700, such as a vacuum pump, is used to provide a vacuum. The vacuum is communicated to the interstitial chamber 3001 by coupling the vacuum source 3700 to the vacuum source end 3172 of the interstitial vacuum port 3170.

The open position of the fluid collection system 3000 is shown in FIG. 52. The lid 3200 is in the open position, and is not sealingly engaged with the canister 3100. The liner 3310 is not shown in FIG. 52.

The closed position of the fluid collection system 3000 is shown in FIGS. 49-50. The lid 3200 is in the closed position. The liner assembly 3300 may be inserted into the canister 3100, such that the liner 3310 is positioned within the cavity 3130 of the canister 3100 and the gland 3500 is inserted into the opening 3213 on the lid 3200. The canister 3100 and the lid 3200 may be in sealing engagement with one another. The lid 3200 and the gland 3500 may be in sealing engagement with one another. The gland 3500 may be in sealing engagement with the liner 3310, the fitment 3410, and the filter 3560. Thus, the interstitial chamber 3001 is formed.

When using the fluid collection system 3000, the lid 3200 begins in the open position as shown in FIG. 52. The user then inserts the liner assembly 3300 into the canister 3100. The fitment assembly 3400 is inserted into the opening 3213 on the lid 3200, such that the latches 3530 on the gland 3500 couple the fitment assembly 3400 to the lid 3200. At the same time, the liner 3310 is positioned within the cavity 3130 of the canister 3100.

Next, the fluid collection system 3000 is moved to a closed position as shown in FIGS. 49-50. The lid 3200 is moved to a closed position and the interstitial chamber 3001 is formed. A patient tube is connected to the patient end 3451 of the fluid port 3450 on the fitment 3410. Any unused ports are capped.

Vacuum is applied to the interstitial chamber 3001. A first method for applying the vacuum to the interstitial chamber 3001 is by physically connecting the vacuum source 3700 to the interstitial vacuum port 3170 (e.g., connecting a tube or other conduit). A second method for applying the vacuum to the interstitial chamber 3001 is by adjusting a regulator or on/off valve associated with the vacuum source 3700, such that the tube or other conduit between the vacuum source 3700 and the interstitial vacuum port 3170 may remain connected between procedures. Air is drawn out of the interstitial chamber 3001 through the interstitial vacuum port 3170 and toward the vacuum source 3700. The vacuum in the interstitial chamber 3001 may cause the liner 3310 to expand and at least partially conform to the interior surface 3112 of the bottom wall 3110 and the interior surface 3128 of the side wall 3120 of the canister 3100. The vacuum in the interstitial chamber 3001 may also draw air out of the fluid chamber 3002 through the fluid chamber vacuum port 3540. Therefore, a vacuum may be applied to both the interstitial chamber 3001 and the fluid chamber 3002.

The reduced pressure in the fluid chamber 3002 creates a vacuum in the fluid chamber 3002. Fluid from the patient flows along the patient tube, through the fluid port 3450, and into the fluid chamber 3002 where the fluid is collected. If the fluid chamber 3002 reaches its capacity (the fluid level in the fluid chamber 3002 rises high enough to saturate the upstream surface 3561 of the filter 3560), the vacuum to the fluid chamber 3002 is shut off, even though vacuum may still be applied to the interstitial chamber 3001 by the interstitial vacuum port 3170.

When the user is ready to remove the liner assembly 3300 from the canister 3100 (for example, at the end of a procedure or when the fluid chamber 3002 reaches its capacity), the vacuum source 3700 is physically disconnected from the interstitial vacuum port 3170, or the vacuum source 3700 is turned off using the regulator or on/off switch. The vacuum is no longer applied to the interstitial chamber 3001, and therefore the vacuum is also no longer applied through the fluid chamber vacuum port 3540 to the fluid chamber 3002. The lid 3200 is moved to the open position. The liner assembly 3300 is removed from the canister 3100 by pressing on the outer surface 3534 of the latches 3530 near the upper end 3532 to release the gland 3500 from the lid 3200, and removing the liner 3310 from the cavity 3130 of the canister 3100.

The fluid may then be removed from the fluid chamber 3002. The fitment 3410 may be removed from the gland 3500, at which point, the gland 3500 becomes a pour spout. The gland 3500 has a dual functionality by both connecting the fitment 3410 to the liner 3310, and acting as a pour spout to allow fluid to be removed from the fluid chamber 3002. Fluid is poured out of the fluid chamber 3002 through the gland 3500. The liner assembly 3300 may then be disposed using standard medical waste disposal techniques.

Figure 73:
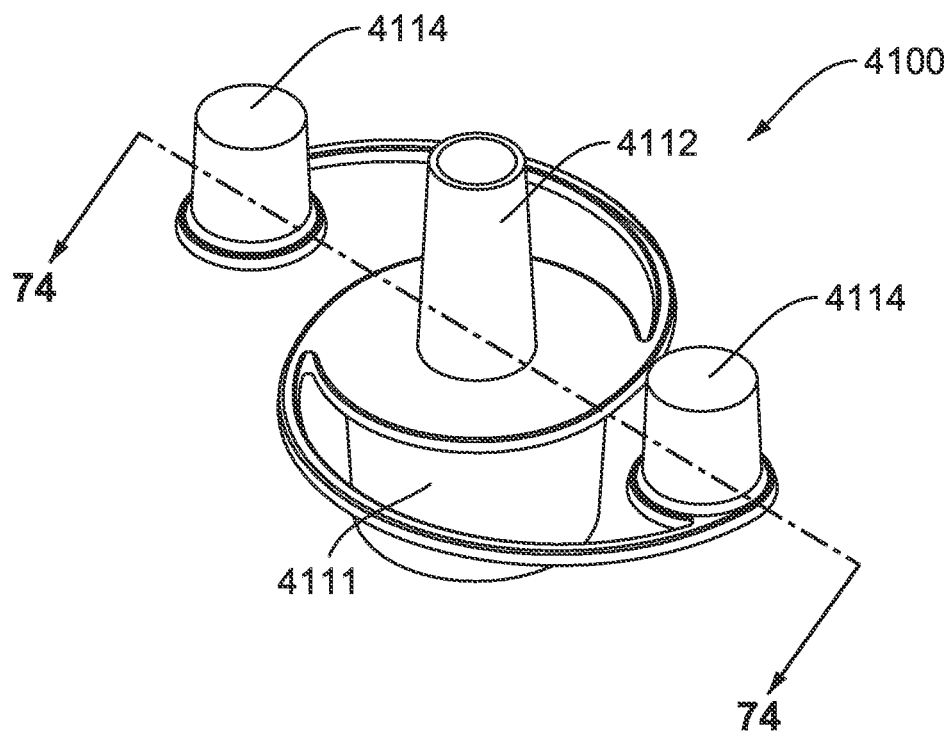
FIG. 73 is an isometric view of a pour spout adapter, shown from above.
Figure 74:
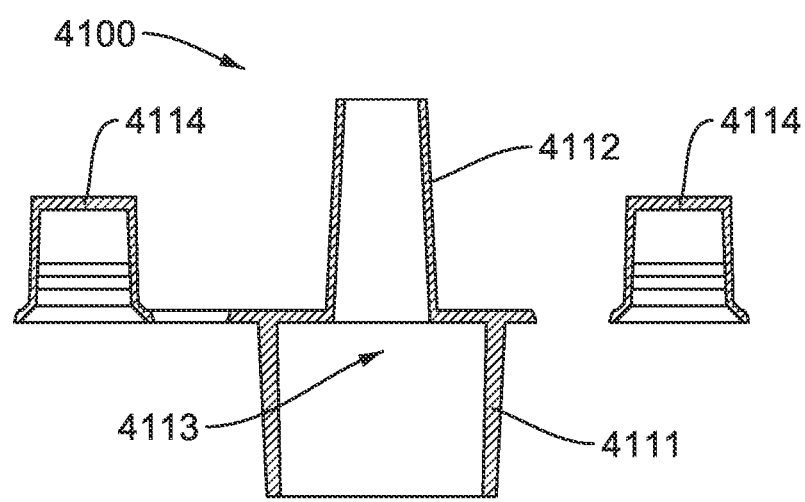
FIG. 74 is a cross-sectional view of the adapter of FIG. 73 taken along line 74, shown from the side.

A pour spout adapter 4100, shown in FIGS. 73-74, may be provided with the fluid collection systems described in this disclosure. The adapter 4100 is intended to be coupled to a pour spout, such that the pour spout can be converted into an additional fluid port. For illustrative purposes, FIG. 75 shows the adapter 4100 coupled to the fitment 1410 of the first embodiment, but the adapter 4100 could be coupled to a pour spout according to any of the embodiments of a fluid collection system. There are at least two reasons that a user would want to convert a pour spout into a fluid port: the user could connect additional suction devices to the canister, or the user could create a tandem canister setup by which fluid can be collected in a second (or third, fourth, etc.) canister after the first canister reaches its capacity.

The adapter 4100 has a pour spout end 4111 designed to connect to the pour spout on the fitment, and a patient end 4112 designed to connect to a patient tube. A channel 4113 connects the pour spout end 4111 and the patient end 4112. During use, fluid will flow from the patient tube through the adapter 4100, through the pour spout on the fitment and into the fluid chamber. The adapter 4100 may be removed at the end of the procedure such that fluid can be emptied from the fluid chamber using the pour spout.

The caps for the fluid port and the pour spout of the fitment assembly may be incorporated into the adapter 4100, thereby eliminating the need for a separate cap assembly. The adapter 4100 in FIGS. 73-74 has two caps 4114. One cap 4114 may be used to close a fluid port on the fitment, as shown in FIG. 75. The other cap 4114 may be used to close the patient end 4112 of the adapter 4100. If the adapter is positioned in a pour spout, placing cap 4114 over the patient end 4112 of the adapter 4100 will effectively close the pour spout as well. In FIG. 75, the cap 4114 is not placed over the patient end 4112 of the adapter 4100, so the patient end 4112 of the adapter 4100 is open, and therefore fluid can flow in and out of the pour spout.

The canisters 1100, 2100 and lids 1200, 2100 of the first and second embodiments are shown as having a rectangular shape, while the canister 3100 and lid 3200 of the third embodiment is shown as having a circular shape. However, any of the canisters discussed in this disclosure could have a rectangular, circular, or elliptical shape. For example, if canisters 1100 and 2100 were circular, the first side wall 1121, 2121 could be a first portion of circular cross-section, and the second side wall 1122, 2122 could be a second portion of the circular cross-section that is on an opposite side from the first portion. Likewise, the third side wall 1123, 2123 and the fourth side wall 1124, 2124 could be a third portion and a fourth portion of the circular cross section, respectively, wherein the first portion is adjacent to the third portion and the fourth portion, and the second portion is adjacent to the third portion and the fourth portion. Additionally, while various features are shown having sharp corners, these corners could also be rounded.

In general, interference fits may be preferred because they reduce the complexity and cost of the finished product. However, one or more gaskets may optionally be provided to ensure sealing engagement between two or more of the lid, canister, gland and fitment of the any of the embodiments. If gaskets are used, it is preferable that the gaskets be positioned on the lid or the canister instead of on the gland or fitment.

Seals created by an interference fit are more reliable if the seals are continuous. Therefore, one advantage of the first and third embodiments is that the seals between the canister and the lid and between the lid and the fitment are continuous (i.e., there is no break in the seal). The first embodiment and the third embodiment are therefore less likely to require a gasket in order to achieve the seals required to form the interstitial chamber.

Various features for attaching the lid and the canister are described here in. Although the first embodiment describe a hinge, the second embodiment describes a tether, and the third embodiment describes sliding connectors, any of the features for attaching the lid and canister could be used in any of the embodiments.

The fluid collection systems have caps to close any fluid port(s) and the pour spout(s) as needed. A separate cap assembly is included in the first embodiment, while the caps are integrally molded with the fitment of the second and third embodiment. However, a separate cap assembly could be provided with any of the embodiments. The bridge of the cap assembly may have a feature that enables the cap assembly to be connected to the fitment (e.g., a pin on the fitment is inserted into a hole on the bridge of the cap assembly). Likewise, the caps could be integrally molded with the fitment in any of the embodiments.

Because vacuum in the fluid chamber is supplied from the interstitial chamber through the fluid chamber vacuum port, it may be desirable to design the fluid collection system to ensure that air is able to flow between the interstitial vacuum port and the fluid chamber vacuum port. Vacuum is supplied to the interstitial chamber through an interstitial vacuum port. Therefore, the vacuum at the interstitial vacuum port could cause the liner to seal around the interstitial vacuum port, and stop the application of vacuum to the interstitial cavity. In embodiments where the fluid chamber vacuum port has a pass-through design, the application of vacuum in the fluid chamber may stop if the liner sealed around the interstitial vacuum port, and ultimately prevent the user from suctioning fluids.

The fluid collection systems could be designed to reduce the possibility of the liner sealing over the interstitial vacuum port. The interstitial vacuum port could be positioned such that the liner would be unlikely to stop communication between the interstitial vacuum port and the fluid chamber vacuum port (e.g., the interstitial vacuum port could be positioned proximate to the fluid chamber vacuum port). Ribs could also be included proximate the interstitial vacuum port to prevent the liner from conforming to the interior surface of the side wall in the area surrounding the cavity end of the interstitial vacuum port. The ribs could extend across the cavity end of the interstitial vacuum port, or could protrude from the interior surface of the side wall in an area adjacent the cavity end of the interstitial vacuum port.

The liners have been described in this disclosure as being made from a single piece of a thin-walled material folded in half to create a first panel having four ends and a second panel having four ends. The fold joins one end on the first panel to one end on the second panel. Seals join the remaining three ends on the first panel to the remaining three ends on the second panel.

However, the liner may be created in other ways. The first panel and the second panel could be formed from two separate sheets of the thin-walled material. In this case, the first panel and the second panel would be joined by seals extending along at least a portion of all four ends. The liner could also be formed from a tube of the thin-walled material. In this case, the tube could be flattened to create the first panel and the second panel. In this case, two opposing ends of the first panel and the second panel are joined folds, while the remaining two ends are joined by seals extending along at least a portion of the ends.

Although the liners are discussed as being made from a first panel and a second panel that each have four ends, it is possible that the first panel and the second panel could be made in a triangular shape with only three ends, or in other shapes having five or more ends. Alternatively, the liner could have circular or elliptical panels. Further, the liners do not need to have only two panels. Additional panels may be included and used as gussets, which may improve the ability of the liner to expand in the cavity of the canister.

The liner of the first embodiment is discussed as forming the seal at the periphery of the liner while leaving an opening in the seal of the liner, and then inserting the fitment into the opening. However, these two steps could be incorporated into a single process wherein the seal between the two panels of the liner and the seal between each panel of the liner and the fitment are made in a single pass.

In some embodiments, a gland is used to couple the fitment to the liner. A gland can be used (or eliminated) in any embodiments of the fluid collection system. If a gland is not included, any features on described as being included in the gland may instead be incorporated into another component (for example, these features may be incorporated into the fitment instead). However, the use of a gland may be preferable when the opening in the liner is on a side of the bag rather than at the top.

Furthermore, a handle may be formed at a periphery of the liner to enable the user to easily lift the liner from the canister. The handle may be formed from the body of the liner, or may be formed from a separate piece of material.

It is believed that the vacuum in the interstitial space will be sufficient to secure the lid in place, and prevent a user from accidentally moving the lid from the closed position to the open position during a procedure. However, a latch or other locking feature may also be provided on the lid and/or canister of any of the embodiments of the fluid collection system to secure the lid in the closed position.

The foregoing description is provided to enable any person skilled in the art to practice the various example implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

The invention claimed is:

1. A fluid collection system comprising:
   a canister having a cavity and an open end;
   a lid, the lid forming a seal with a portion of the open end of the canister when the fluid collection system is in a closed position; and
   a fluid receptacle comprising a liner and a fitment assembly, the liner and fitment assembly together defining a fluid chamber,
   wherein the canister, the lid, and the fluid receptacle define an interstitial chamber,
   wherein the fitment assembly comprises a fluid chamber vacuum port which allows communication between the fluid chamber and the interstitial chamber,
   wherein the lid and the open end of the canister define an aperture therebetween when the fluid collection system is in the closed position, and
   wherein at least a portion of the fitment assembly seals around the aperture when the fluid collection system is in the closed position.

2. The fluid collection system of claim 1, wherein the aperture between the lid and the open end of the canister when the fluid collection system is in the closed position is formed at a notch in the open end of the canister.

3. The fluid collection system of claim 1, wherein at least a portion of the aperture is formed in a notch proximate the open end of the canister.

4. The fluid collection system of claim 3, wherein at least a portion of the aperture is formed in the canister, the lid, or both the lid and the canister.

5. The fluid collection system of claim 4, wherein at least a portion of the notch is formed in a sidewall portion of the canister.

6. The fluid collection system of claim 1, wherein an interstitial vacuum port is positioned on the canister.

7. The fluid collection system of claim 6, wherein the interstitial vacuum port is positioned on a sidewall portion of the canister.

8. The fluid collection system of claim 6, wherein the interstitial vacuum port is connected to a vacuum source, wherein the interstitial chamber is in fluid communication with both the vacuum source and the fluid chamber, and wherein the interstitial chamber is positioned between the vacuum source and the fluid chamber.

9. The fluid collection system of claim 6, wherein the interstitial vacuum port is connected to a vacuum source and wherein the fluid chamber is in fluid communication with the vacuum source through the interstitial chamber.

10. The fluid collection system of claim 1, wherein the lid and the canister form a sealing arrangement around the fitment assembly when the fitment assembly is positioned within the aperture and when the lid and the canister are in the closed position.

11. The fluid collection system of claim 10, wherein at least a portion of the lid forms a sealing arrangement with at least a portion of the fitment assembly when the fitment assembly is positioned within the aperture and when the lid and the canister are in a closed position.

12. The fluid collection system of claim 1, wherein the fluid chamber vacuum port is formed in a fitment of the fitment assembly.

13. The fluid collection system of claim 12, wherein the fitment includes at least one fluid port that is in fluid communication with the fluid chamber.

14. The fluid collection system of claim 13, wherein the at least one fluid port is in fluid communication with a vacuum source, sequentially, through the fluid chamber, through the fluid chamber vacuum port and through the interstitial chamber.

15. The fluid collection system of claim 1, wherein the fitment assembly includes a filter positioned adjacent to the fluid chamber vacuum port.

16. The fluid collection system of claim 1, wherein a fitment of the fitment assembly includes a protrusion around which the aperture forms a sealing arrangement when the fitment assembly is positioned within the aperture and when the fluid collection system is in the closed position.

* * * * *